(12) United States Patent
Gimzewski et al.

(10) Patent No.: US 10,802,012 B2
(45) Date of Patent: *Oct. 13, 2020

(54) OPTICAL CYTOMETRY TO DETERMINE CELL MASS CHANGES IN RESPONSE TO A BIOLOGICALLY ACTIVE AGENT

(71) Applicant: The Regents of the University of California, Oakland, CA (US)

(72) Inventors: James K. Gimzewski, Topanga, CA (US); Jason C. Reed, Los Angeles, CA (US); Michael A. Teitell, Tarzana, CA (US)

(73) Assignee: The Regents of the University of California, Oakland, CA (US)

(*) Notice: Subject to any disclaimer, the term of this patent is extended or adjusted under 35 U.S.C. 154(b) by 28 days.

This patent is subject to a terminal disclaimer.

(21) Appl. No.: 15/726,285

(22) Filed: Oct. 5, 2017

(65) Prior Publication Data
US 2018/0156779 A1    Jun. 7, 2018

Related U.S. Application Data

(60) Division of application No. 14/088,992, filed on Nov. 25, 2013, now Pat. No. 9,810,683, which is a (Continued)

(51) Int. Cl.
*G01N 33/50* (2006.01)
*G01J 3/453* (2006.01)
(Continued)

(52) U.S. Cl.
CPC .......... *G01N 33/5008* (2013.01); *G01J 3/453* (2013.01); *G02B 5/126* (2013.01); *G02B 21/0056* (2013.01); *G02B 21/32* (2013.01)

(58) Field of Classification Search
CPC ................ G01N 33/5008; G02B 21/32; G02B 21/0056; G01J 3/453
See application file for complete search history.

(56) References Cited

U.S. PATENT DOCUMENTS 5,133,601 A    7/1992    Cohen et al.
5,471,303 A    11/1995    Ai et al.
(Continued)

FOREIGN PATENT DOCUMENTS

CN    1415067 A     4/2003
CN    101313196 A    11/2008
(Continued)

OTHER PUBLICATIONS

U.S. Final Office Action dated Jun. 4, 2018 issued in U.S. Appl. No. 14/890,578.
(Continued)

*Primary Examiner* — Hwa Andrew Lee
(74) *Attorney, Agent, or Firm* — Tom Hunter; Weaver Austin Villeneuve & Sampson LLP

(57) ABSTRACT

The present invention provides optical systems and methods for determining a characteristic of a cell, such as cell type, cellular response to a biochemical event, biological state and the like. The methods typically involve using interferometry to observe membrane properties in a cell and then use this information to determine one or more characteristics of a cell. The methods of the invention are useful for applications such as drug screening as well as diagnostic techniques.

9 Claims, 34 Drawing Sheets

Related U.S. Application Data continuation of application No. 12/436,702, filed on May 6, 2009, now Pat. No. 8,599,383.

(51) Int. Cl.
*G02B 5/126* (2006.01)
*G02B 21/00* (2006.01)
*G02B 21/32* (2006.01)

(56) References Cited

U.S. PATENT DOCUMENTS

| | | | |
|---|---|---|---|
| 6,377,721 | B1 | 4/2002 | Walt et al. |
| 6,449,048 | B1 | 9/2002 | Olszak |
| 6,858,184 | B2 | 2/2005 | Pelrine et al. |
| 7,610,074 | B2 | 10/2009 | Boppart et al. |
| 8,343,497 | B2 | 1/2013 | Shi et al. |
| 8,524,488 | B2 | 9/2013 | Gimzewski et al. |
| 8,599,383 | B2 | 12/2013 | Teitell et al. |
| 8,994,864 | B2 | 3/2015 | Yamamoto et al. |
| 9,810,683 | B2 | 11/2017 | Gimzewski et al. |
| 9,873,870 | B2 | 1/2018 | Flenchtner et al. |
| 10,203,331 | B2 | 2/2019 | Reed et al. |
| 2002/0196450 | A1 | 12/2002 | Olszak et al. |
| 2003/0234936 | A1 | 12/2003 | Marron |
| 2004/0058458 | A1 | 3/2004 | Anker et al. |
| 2004/0066520 | A1 | 4/2004 | Marron |
| 2004/0210289 | A1 | 10/2004 | Wang et al. |
| 2004/0218189 | A1 | 11/2004 | Izatt et al. |
| 2004/0252310 | A1 | 12/2004 | De Lega et al. |
| 2004/0258759 | A1 | 12/2004 | Suslick et al. |
| 2005/0057756 | A1 | 3/2005 | Fang-Yen et al. |
| 2005/0058990 | A1 | 3/2005 | Guia et al. |
| 2005/0088663 | A1 | 4/2005 | De Groot et al. |
| 2005/0117165 | A1 | 6/2005 | Holbrook et al. |
| 2005/0122527 | A1 | 6/2005 | Boccara et al. |
| 2005/0167578 | A1 | 8/2005 | Riza et al. |
| 2005/0195405 | A1 | 9/2005 | Ina et al. |
| 2005/0200856 | A1 | 9/2005 | Groot |
| 2005/0225769 | A1 | 10/2005 | Bankhead et al. |
| 2005/0239047 | A1 | 10/2005 | Gimzewski et al. |
| 2005/0248770 | A1 | 11/2005 | Lin |
| 2006/0291712 | A1 | 12/2006 | Popescu et al. |
| 2007/0279638 | A1 | 12/2007 | Choo et al. |
| 2008/0018966 | A1 | 1/2008 | Dubois et al. |
| 2009/0125242 | A1 | 5/2009 | Choi et al. |
| 2009/0163564 | A1 | 6/2009 | Borden et al. |
| 2009/0238817 | A1 | 9/2009 | Kozlowski |
| 2009/0325211 | A1 | 12/2009 | Fang et al. |
| 2010/0079763 | A1 | 4/2010 | Arvidson et al. |
| 2010/0284016 | A1 | 11/2010 | Teitell et al. |
| 2012/0107840 | A1 | 5/2012 | Wagner et al. |
| 2014/0080171 | A1 | 3/2014 | Gimzewski et al. |
| 2014/0178865 | A1 | 6/2014 | Reed et al. |
| 2016/0103118 | A1 | 4/2016 | Teitell et al. |

FOREIGN PATENT DOCUMENTS

| | | |
|---|---|---|
| CN | 101346673 A | 1/2009 |
| EP | 1971690 | 9/2008 |
| EP | 2224946 | 9/2010 |
| JP | 2007-524075 | 8/2007 |
| JP | 2009-276327 A | 11/2009 |
| JP | 2010-505123 A | 2/2010 |
| JP | 2011-509248 A | 3/2011 |
| WO | WO 01/31286 A2 | 5/2001 |
| WO | WO 2005/001445 A2 | 1/2005 |
| WO | WO 2007/123579 A2 | 11/2007 |
| WO | WO 2008/060369 A2 | 5/2008 |
| WO | WO 2009/086516 A1 | 7/2009 |
| WO | WO 2013/019984 A1 | 2/2013 |
| WO | WO 2014/190303 A1 | 11/2014 |

OTHER PUBLICATIONS

U.S. Notice of Allowance dated Sep. 20, 2018 issued in U.S. Appl. No. 14/235,547.
Extended European Search Report dated Jun. 19, 2018 issued in EP 18155863.6.
Japanese Notice of Allowance dated Jun. 4, 2018 issued in JP 2016-515128.
Canadian First Office Action dated Jun. 5, 2018 issued in CA 2,843,445.
European Office Action dated Jan. 15, 2019 issued in EP 12 819 806.6.
Japanese Decision to Grant Patent dated May 9, 2018 issued in JP 2017-094485.
Korean First Office Action dated Jul. 10, 2018 issued in KR 10-2014-7005381.
U.S. Office Action dated Oct. 12, 2017 issued in U.S. Appl. No. 14/890,578.
U.S. Office Action dated Oct. 7, 2011 issued in U.S. Appl. No. 12/436,702.
U.S. Office Action dated Jul. 20, 2012 issued in U.S. Appl. No. 12/436,702.
U.S. Final Office Action dated Jan. 22, 2013 issued in U.S. Appl. No. 12/436,702.
U.S. Notice of Allowance dated Jul. 30, 2013 issued in U.S. Appl. No. 12/436,702.
U.S. Office Action dated Mar. 29, 2016 issued in U.S. Appl. No. 14/088,992.
U.S. Notice of Allowance dated Jan. 17, 2017 issued in U.S. Appl. No. 14/088,992.
U.S. Notice of Allowance dated May 18, 2017 issued in U.S. Appl. No. 14/088,992.
U.S. Notice of Allowance dated Sep. 11, 2017 issued in U.S. Appl. No. 14/088,992.
U.S. Restriction Requirement dated Jun. 6, 2016 issued in U.S. Appl. No. 14/235,547.
U.S. Office Action dated Nov. 18, 2016 issued in U.S. Appl. No. 14/235,547.
U.S. Final Office Action dated Aug. 24, 2017 issued in U.S. Appl. No. 14/235,547.
PCT International Search Report and Written Opinion dated Sep. 25, 2014 issued in PCT/US2014/039418.
PCT International Preliminary Report on Patentability dated Dec. 3, 2015 issued in PCT/US2014/039418.
Canadian First Office Action dated Oct. 18, 2017 issued in CA 2,912,842.
Chinese First Office Action dated Jun. 30, 2017 issued in CN 201480029374.4.
Chinese Second Office Action [No translation] dated Mar. 13, 2018 issued in CN 201480029374.4.
European Communication pursuant to Rules 161(2) and 162 EPC dated Jan. 13, 2016 issued in EP 14801181.0.
European Extended Search Report dated Nov. 18, 2016 issued in EP 14801181.0.
Japanese Notice of Reasons for Rejection dated Nov. 20, 2017 issued in JP 2016-515128.
Korean Notice of Grounds for Rejection dated Mar. 15, 2018 issued in KR 102015-7033208.
PCT International Search Report and Written Opinion dated Dec. 12, 2012 issued in PCT/US2012/049388.
PCT International Preliminary Report on Patentability dated Feb. 13, 2014 issued in PCT/US2012/049388.
Australian Patent Examination Report No. 1 dated Feb. 12, 2015 issued in AU 2012290024.
Australian Patent Examination Report No. 1 dated Jun. 6, 2017 issued in AU 2016200629.
Chinese First Office Action dated Nov. 24, 2015 issued in CN 201280048126.5.
Chinese Second Office Action dated Jul. 25, 2016 issued in CN 201280048126.5.
Chinese Third Office Action dated Mar. 24, 2017 issued in CN 201280048126.5.
European Communication pursuant to Rules 161(2) and 162 EPC dated Mar. 12, 2014 issued in EP 12 819 806.6.

(56) References Cited

OTHER PUBLICATIONS

European Extended Search Report dated Mar. 16, 2015 issued in EP 12 819 806.6.
Japanese Office Action dated May 25, 2016 issued in JP 2014-524086.
Japanese Decision to Grant Patent dated Apr. 12, 2017 issued in JP 2014-524086.
Balagopalan et al. (Jan. 2011) "Imaging techniques for assaying lymphocyte activation in action," *Nat Rev Immunol*, 11:21-33.
Barer, R. (Mar. 1, 1952) "Interference microscopy and mass determination," *Nature*, 169:366-367.
Burnes, D (2012) "Quantifying biomass changes of single cells during antigen-specific CD8+ T cell mediated cytotoxicity" *Electronic Thesis and Dissertations UCLA* 33 pages.
Davies et al. (Mar. 29, 1952) "Interference microscopy and mass determination," *Nature*, 169:541.
Davies et al. (Sep. 1954) "The Use of the Interference Microscope to Determine Dry Mass in Living Cells and as a Quantitative Cytochemical Method," *Quarterly Journal of Microscopical Science*, 95(part 3):271-304.
Edwards et al. (2011) "T cell recognition of weak ligands: roles of signaling, receptor number, and affinity," *Immunol Res*, 50(1):39-48 [NIH Public Access—Author Manuscript 17pp].
Erskine et al. (2012) "Determining Optimal Cytotoxic Activity of Human Her2neu Specific CD8 T cells by Comparing the Cr51 Release Assay to the xCELLigence System," *Journal of Visualized Experiments and ACEA Biosciences*, 66:e3683 (1-6).
Gamble et al. (Jan. 7, 1960) "Studies in Histochemistry: LVIL. Determination of the Total Dry Mass of Human Erythrocyes by Interference Microscopy and X-ray Microradiography," *The Journal of Biophysics and Biochemical Cytology*, 8:53-60.
Gohring et al. (2010) "Label free detection of CD4+ and CD8+ T cells using the optofluidic ring resonator," *Sensors*, 10(6):5798-5808.
Hobeika et al. (Jan. 1, 2005) "Enumerating Antigen-Specific T-Cell Responses in Peripheral Blood," *Journal of Immunotherapy*, 28(1):63-72.
Kwong et al. (2009) "Modular nucleic acid assembled p/MHC microarrays for multiplexed sorting of antigen-specific T cells," *J Am Chem Soc*, 131(28):9695-9703.
Ma et al. (Jun. 2011) "A clinical microchip for evaluation of single immune cells reveals high functional heterogeneity in phenotypically similar T cells," *Nature Medicine*, 17(6):738-743.
Mir et al. (2011) "Optical measurement of cycle-dependent cell growth," *Proceedings of the National Academy of Sciences*, 108(32):13124-13129.
Moore et al. (2004) "Tracking the Recruitment of Diabetogenic CD8+T-Cells to the Pancreas in Real Time," *Diabetes*, 53:1459-1466.
Pittet et al. (2007) "In vivo imaging of T cell delivery to tumors after adoptive transfer therapy," *PNAS*, 104(30):12457-12461.
Rathmell et al. (Sep. 1, 2000) "In the Absence of Extrinsic Signals, Nutrient Utilization by Lymphocytes Is Insufficient to Maintain Either Cell Size or Viability,"*Molecular Cell.*, 6(3): 683-692.
Reed et al. (2006) "Applications of Imaging Interferometry," *Proceedings of SPIE, The International Society for Optical Engineering*, 0277-786X, 6293:629301-1-629301-8.
Reed et al. (Aug. 14, 2006) "Observation of nanoscale dynamics in cantilever sensor arrays," *Nanotechnology*, 17(15):3873-3879.
Reed et al. (Jun. 11, 2008) "High throughput cell nanomechanics with mechanical imaging interferometry,"*Nanotechnology*, 19(23):pp. 1-8.
Reed et al. (2008) "Live Cell Interferometry Reveals Cellular Dynamism During Force Propagation," *ACS NANO*,2(5): 841-846.
Reed et al. (Sep. 2011) "Rapid, massively parallel single-cell drug response measurements via live cell interferometry," *Biophysical Journal*, 101:1025-1031.
Rosenberg et al. (Apr. 2008) "Adoptive cell transfer: a clinical path to effective cancer immunotherapy," *Nat Rev Cancer*, 8(4): 299-308 [NIH Public Access—Author Manuscript—22 pages.].
Stone et al. (2009) "T-cell receptor binding affinities and kinetics: impact on T-cell activity and specificity," *Immunology*, 126(2):165-176.
Tian et al. (2007) "$CD8^+T$ cell activation is governed by TCR-peptide/MHC affinity, not dissociation rate," *Journal of Immunology*, 179:2952-2960.
Tzur et al. (2011) "Optimizing optical flow cytometry for cell volume-based sorting and analysis," *PLoS One*, 6(1):e16053 (1-9).
Whiteside, T.L. (2004) "Methods to monitor immune response and quality control," *Dev Biol (Basel)* 116:219-228; discussion 229-236 [Abstract available, 2 pages].
Wooldridge et al. (2009) "Tricks with tetramers: how to get the most from multimeric peptide-MHC," *Immunology*, 126:147-164.
Zangle et al. (Jul. 2013) "Quantifying Biomass Changes of Single CD8+ T Cells during Antigen Specific Cytotoxicity," *PLoS One* 8(7):e68916 (1-8).
Zangle et al. (Feb. 19, 2014) "High-Throughput Screening off Cell Cytotoxic Events by Biomass Profiling," *Biophysical Journal 4095-Pos Board B823*, 106(2):811a (1 page).
U.S. Final Office Action dated Dec. 10, 2019 issued in U.S. Appl. No. 14/890,578.
European 2nd Office Action dated Nov. 25, 2019 issued in EP 12 819 806.6.
Popescu et al. (2008) "Optical imaging of cell mass and growth dynamics," *Am J Physiol*, 295: C538-0544, DOI: 10.1152/AJPCELL. 00121.2008.
Rappaz, Benjamin et al. (May/Jun. 2009) "Noninvasive characterization of the fission yeast cell cycle by monitoring dry mass with digital holographic microscopy", *Journal of Biomedical Optics* 14(3): 034049(1-5) (5 pages), DOI:10.1117/1.3147385.
Z. El-Schish et al. (2010) "Digital holographic microscopy—innovative and nondestructive analysis of living cells", XP055643679, (8 pages), Retrieved from the Internet: URL: http://muep.mau.se/bitstream/handle/2043/11217/Article%20EISchish%20et%20a1%202010%20final%20version.pdf?sequence=l&isAllowed=y.
U.S. Office Action dated Jul. 15, 2019 issued in U.S. Appl. No. 14/890,578.
Australian Patent Examination Report No. 1 dated Jun. 7, 2019 issued in AU 2014268394.
Australian Patent Examination Report No. 1 dated Jun. 27, 2019 issued in AU 2018232924.

Active response from cell : applies upward force on reflector

Uniform Cell Packing for Analysis

Which cells matter most?

2,500 nm

OPTICAL CYTOMETRY TO DETERMINE CELL MASS CHANGES IN RESPONSE TO A BIOLOGICALLY ACTIVE AGENT

CROSS REFERENCE TO RELATED APPLICATIONS

This application is a divisional of U.S. patent application Ser. No. 14/088,992, filed Nov. 25, 2013, which is a continuation application that claims the benefit under 35 U.S.C. § 120 of U.S. patent application Ser. No. 12/436,702, filed May 6, 2009, the contents of all of which are incorporated herein by reference. This application is related to U.S. patent application Ser. No. 11/077,266 filed Mar. 9, 2005, the contents of which is incorporated herein by reference.

STATEMENT OF GOVERNMENT SUPPORT

This invention was made with Government support under Grant No. CA090571, CA107300, and GM074509, awarded by the National Institutes of Health. The Government has certain rights in the invention.

BACKGROUND OF THE INVENTION

1. Field of the Invention

This invention relates to interferometric systems, materials and techniques that can used to examine one or more cells.

2. Description of Related Art

Cells are capable of many complex functions such as motility, cell-cell communication and the synthesis of a wide variety of biologically active molecules. Cell membranes play a crucial role in many of these functions in part due to their ability to adopt a wide variety of morphological configurations, configurations which depend on factors such as cellular physiology as well as cell type and lineage specific functions.

Cell membranes and other physical structures of cells are complex and dynamic, with cytoskeletal elements oriented in many directions, and thus their mechanical properties are highly anisotropic, and vary widely among individual cells within a population (see, e.g. Smith et al., (2003) American Journal of Physiology-Lung Cellular and Molecular Physiology 285, L456-L463; Hu et al., (2003) American Journal of Physiology-Cell Physiology 285, C1082-C1090; Fabry et al., (2001) Physical Review Letters 8714; and Fabry et al., (2001) Journal of Applied Physiology 91, 986-994). The degree and significance of this mechanical anisotropy and its population variances is poorly characterized, however, due to methodological limitations of existing nano-mechanical probing techniques.

Existing cytometric approaches, such as those using AFM (see, e.g. Mahaffy et al., (2004) Biophysical Journal 86, 1777-1793), and high-magnification particle tracking microrheology (see, e.g. Weihs et al., (2006) Biophysical Journal 91, 4296-4305), are simply too slow to adequately measure the number of individual cells required for population comparisons. On the other hand, wide-field magnetic/optical bead tracking methods, which rely on beads fixed to the cell surface, can only track the probe with sufficient accuracy (tens of nanometers (see, e.g. Mijailovich et al., (2002) Journal of Applied Physiology 93, 1429-1436; and Cheezum et al., (2001) Biophysical Journal 81, 2378-2388) in two dimensions (the x-y plane perpendicular to the objective).

In view of the limitations with existing cytometric technologies, there is a specific need to extend probe-based mechanical measurements into all three dimensions, while retaining measurement accuracy and high throughput. In addition, there is a general need in the art for optimized methods of observing and/or determining one or more characteristics of a cell (e.g., determining the physiological status or biological state of a cell; determining the cell type of a cell; determining the response of a cell to a biochemical event; etc.). The instant invention addresses these needs.

SUMMARY OF THE INVENTION

Embodiments of the invention include, for example, systems, methods and materials that can be used to determine one or more characteristics of a deformable material such as the membrane of a cell. Illustrative embodiments of the invention involve observing one or more properties of a cell with an interferometer and then using these observations to characterize one or more aspects of cellular physiology. Such properties include for example: observations of cell and/or cell membrane motion by observing membranes coated with micromirrors; observations cell and/or cell membrane motion in the absence of micromirrors via real-time phase measurements; as well as observations of optical cell thickness (cell density), cell volume, and the like. The systems and methods of the invention can be used for example to obtain information useful for a wide variety of biomedical applications such as diagnostic procedures (e.g. to identify a pathological condition in an individual from which a cell is obtained) as well as drug screening assays (e.g. to test and identify agents capable of modulating a cell's physiology). The systems and methods of the invention can also be used, for example, to measure cell responses to any physical change in the local environment, such as change in temperature, pH, force application, and cell density and neighboring cell effects, such as touching, cytokine related signaling, vibration sensing, and others.

The invention disclosed herein has a number of embodiments. Embodiments of the invention include, for example, systems and/or methods for observing a property of a deformable material comprising: a microscope capable of measuring a feature of interest in a sample; a detector operatively coupled to the microscope; a sample assembly comprising an observation chamber adapted to contain the deformable material; and a plurality of reflective microparticles capable of adhering to the deformable material, wherein the average diameter of the reflective microparticles is between 0.5 μm and 30 μm. In certain embodiments, the microscope is a confocal microscope. In other embodiments, the microscope is an interference microscope capable of observing interference fringes through a fluid medium. The systems and/or methods of the invention can be used to obtain a variety of types of information, for example information relating to an axial position of a magnetic reflective microparticle disposed on or proximal to a deformable material; and/or information relating to a z motion of a magnetic reflective microparticle disposed on or proximal to the deformable material. Certain embodiments of systems and/or methods disclosed herein comprise optical profiling techniques such as confocal or digital holography, spectrally resolved interferometry, wavelength scanning interferometry, digital holography and the like.

A general embodiment of the invention is a system for observing a property of a deformable material comprising: a microscope having a Michelson interference objective; a detector such as a camera (e.g. a still camera, a video camera, charge coupled devices (CCD) and the like) operatively coupled to the microscope; a sample assembly comprising an observation chamber adapted to contain the deformable material; a reference assembly comprising a reference chamber; a plurality of reflective magnetic microparticles capable of adhering to the deformable material; and a magnet disposed below the observation chamber and oriented coaxially with an optical axis; wherein the magnet is operatively coupled to a motorized micrometer and adapted to exert a magnetic force on a magnetic reflective microparticle adhered to the surface of the deformable material. Such general embodiments are non-limiting as the systems disclosed herein can adopt a variety of configurations. Embodiments of the invention further include methods for observing a property of a deformable material using the systems disclosed herein. While cellular membranes are the focus of the following disclosure relating to these systems and methods, those of skill in the art understand that a wide variety of other deformable materials can be observed and/or characterized using embodiments of the invention disclosed herein.

One typical embodiment of the invention is a system for obtaining an image of a cell (and/or cells within a population simultaneously) comprising: a microscope having a Michelson interference objective; a camera operatively coupled to the microscope; a sample assembly comprising an observation chamber adapted to contain the cell; a reference assembly comprising a reference chamber adapted to contain a fluid; and a plurality of reflective microparticles capable of adhering to the cell, wherein the average diameter of the reflective microparticles is between 0.5 µm and 30 µm (e.g. spherical magnetic microparticles having an average diameter of between 1 µm and 15 µm or 5 µm and 10 µm etc.). Optionally the reflective microparticles comprise a gradient index (GRIN) spherical lens. In certain embodiment of the invention, the reference assembly further comprises: a first optical window; a first housing element adapted to hold the first optical window; a second optical window; a second housing element adapted to hold the second optical window; and a plurality of spherical spacer elements disposable between the first optical window and the second optical window and adapted to separate the first and second optical windows to a defined distance. In embodiments of the invention, the sample assembly can further comprise: a viewing window and a first housing element adapted to hold the viewing window, wherein the thickness of the viewing window is equivalent to the combined thickness of the first and second optical windows in the reference assembly. Moreover, in such embodiments of the invention the sample assembly can also comprise a plurality of spherical spacer elements disposable between the viewing window and a top portion of the observation chamber and adapted to separate the viewing window and the top portion of the observation chamber to a defined distance that is equivalent to the defined distance between the first and second optical windows in the reference assembly. In typical embodiments of the invention, a surface of the observation chamber (e.g. the surface that is farthest away from the detection camera lens) is reflective.

Embodiments of the invention include a variety of permutations of these systems. For example, in certain embodiments, the observation chamber comprises at least one perfusion conduit adapted to circulate a cell media within the chamber. Optionally the observation chamber is operatively coupled to other elements adapted to control the environment in which the cell is disposed such as heating elements and the like. Some embodiments of the invention also include a magnet disposed below the observation chamber and oriented coaxially with an optical axis. Typically in such embodiments, the magnet is operatively coupled to a motorized micrometer and adapted to exert a magnetic force of between 0 Newtons and 5 nanoNewtons on a magnetic reflective microparticle adhered to the surface of a cell. In some embodiments of the invention, the magnet is typically adapted to generate a magnetic field of between 200 Gauss and 3 kiloGauss. In embodiments of the invention, the magnet is typically adapted to generate a magnetic field gradient range of between 300,000 to 800,000 Gauss/meter. Typical embodiments of the invention further comprise a processor element and a memory storage element adapted to process and store one or more images of the cell.

Related embodiments of the invention include methods of using the systems disclosed herein. One such embodiment of the invention is a method for observing a property of a cell, the method comprising: adhering a reflective magnetic microparticle to the cell; placing the cell in a cell observation chamber of an optical microscope having a Michelson interference objective; exposing the cell coated with the microparticle to a magnetic field; and then using the Michelson interference objective to observe the movement of the microparticle adhered to the cell in response to the applied magnetic field, wherein the movement of the reflective microparticle adhered to the cell correlates to a property of the cell, so that a property of the cell is observed.

A variety of methodological embodiments are contemplated. For example, certain methodological embodiments of the invention are performed using a system comprising: a camera operatively coupled to the microscope; a sample assembly comprising an observation chamber adapted to contain the cell; a reference assembly comprising a reference chamber adapted to contain a fluid; a memory storage element adapted to store one or more images of the cell; and a processor element adapted to process one or more images of the cell.

The methods of the invention can be used to obtain a wide variety of information relating to one or more cellular properties. For example, in certain embodiments of the invention, the method can be used to observe an optical thickness of a live cell in an aqueous medium. Alternatively, the method can be used to observe a cell mass property of a live cell in an aqueous medium. In some embodiments of the invention, the method is used to observe a viscoelastic property of a live cell in an aqueous medium. Optionally, the method is used to observe a population of live cells, for example to observe resting and dynamic responses to stimuli in a population of live cells. Typically in these methods, the property is observed in response to the cell's exposure to a stimulus such as the magnetic field applied to the cell and/or a composition introduced into the cell's media. Optionally the methods further comprise removing the cell from the observation chamber and manipulating the cell for a further analysis. In certain embodiments of the invention, the method is used to obtain information comprising a cell specific profile of a live cell in an aqueous medium and to then store this information in the memory storage element.

Embodiments of the invention also include a reflective microparticle comprising a gradient index (GRIN) spherical lens. Those of skill in the art will further understand that other types of particles can be used in embodiments of the invention. For example, relatively uniform and flat cylindrical 8-10 micron nickel beads (e.g. ones made by photoresist/electroplating methods) can be used in various embodiments of the invention. Optionally such microparticles are coupled to a flexible tether and/or an optical fiber and/or is operatively coupled to an endoscope. In certain embodiments of the invention, this microparticle comprises a plurality of material layers, wherein refractive indices of the material layers decrease from the center of the microparticle.

Other objects, features and advantages of the present invention will become apparent to those skilled in the art from the following detailed description. It is to be understood, however, that the detailed description and specific examples, while indicating some embodiments of the present invention are given by way of illustration and not limitation. Many changes and modifications within the scope of the present invention may be made without departing from the spirit thereof, and the invention includes all such modifications.

DETAILED DESCRIPTION

Figure 1A:
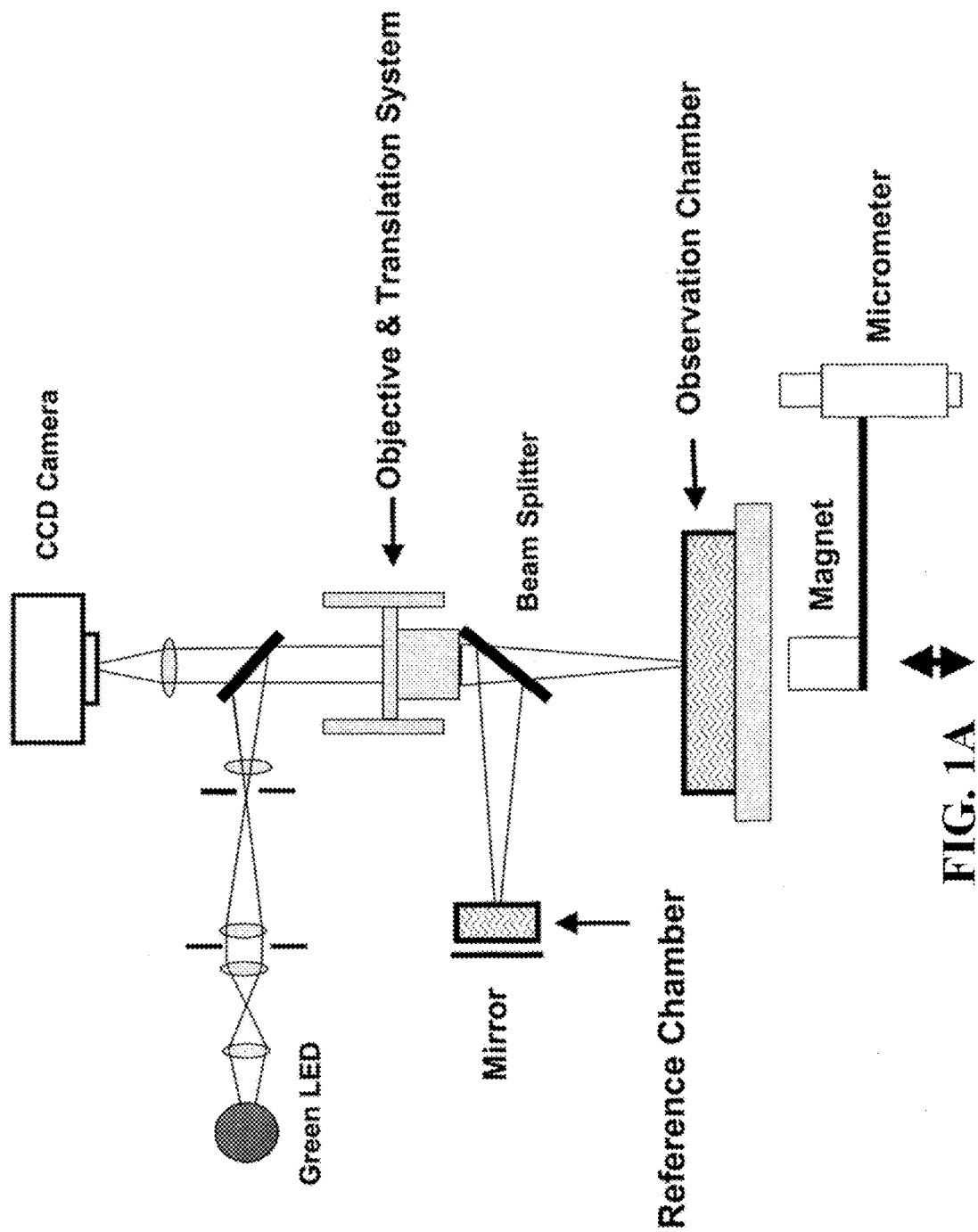
FIG. 1A shows a schematic of an embodiment of an interferometric microscope. This microscope embodiment can typically accommodate a 5× and 20× long-working distance microscope objective. Embodiments of the invention can use other objective lenses known in the art, for example those used for higher and lower magnification (e.g. 50× etc.). Below the objective is the Michelson interferometer with an adjustable mirror in the reference arm. A fluid compensation cell is positioned in the interferometer's reference arm to permit measurements inside the media-filled cell chamber. In embodiments of the invention, the dimensions of the compensation cell can be adjusted to exactly match the optical path length between the test and reference arms. With this system, cells can be evaluated in a sealed environmental chamber maintained at 5%$CO_2$, 37° C., with infusion ports for exchanging media and the introduction of drugs and other chemicals. Typically this embodiment, a cylindrical rare-earth magnet mounted on a micrometer is typically positioned below the cell chamber. The magnitude of the magnetic force applied to the nickel microreflectors inside the cell chamber is then adjusted by varying the distance between the magnet pole face and the sample.
Figure 1B:
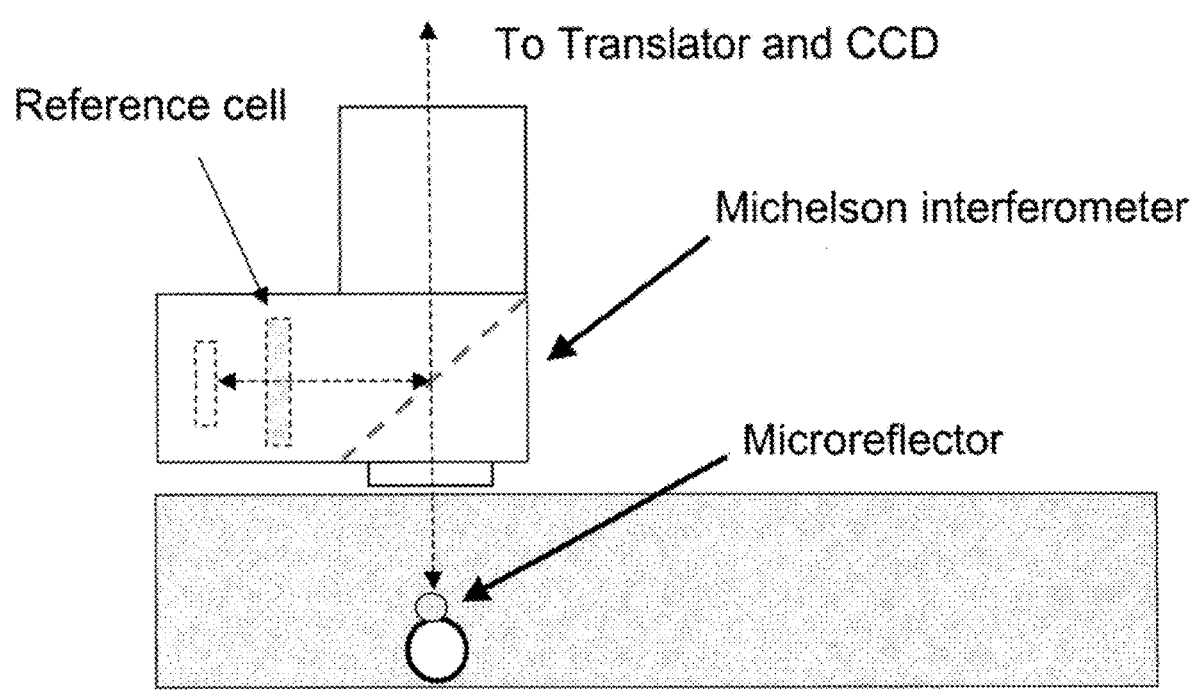
FIG. 1B shows a side view schematic of interferometric microscope system elements that can be used with embodiments of the invention.
Figure 1C:
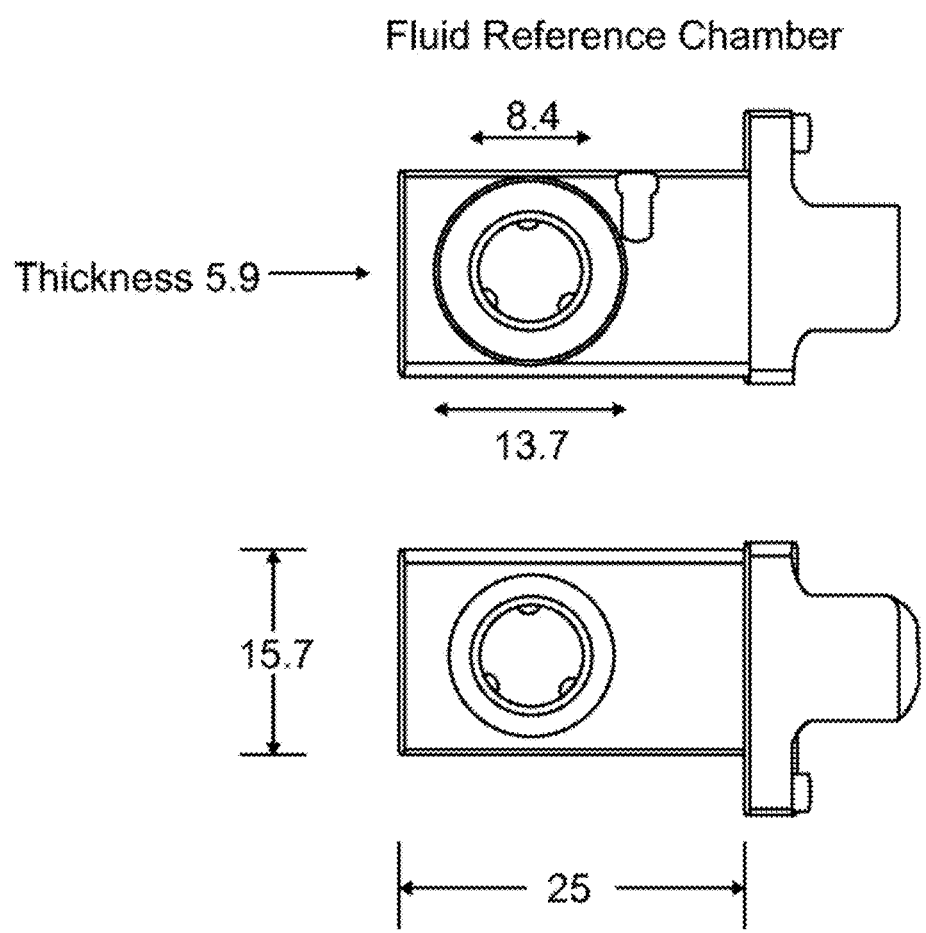
FIG. 1C shows photographs of non-magnetic stainless steel reference and sample assembly elements that can be used with embodiments of the invention.
Figure 1D:
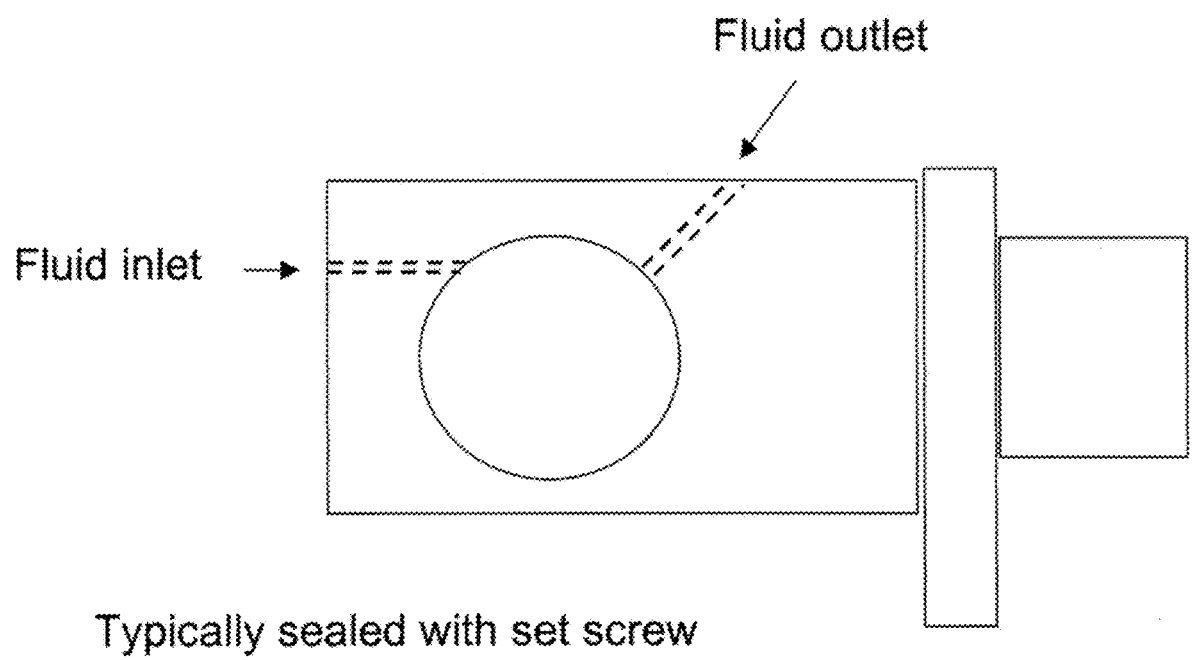
FIG. 1D shows a schematic of sample assembly elements (e.g. the arrangement of windows in the assembly that can be used with embodiments of the invention.
Figure 1E:
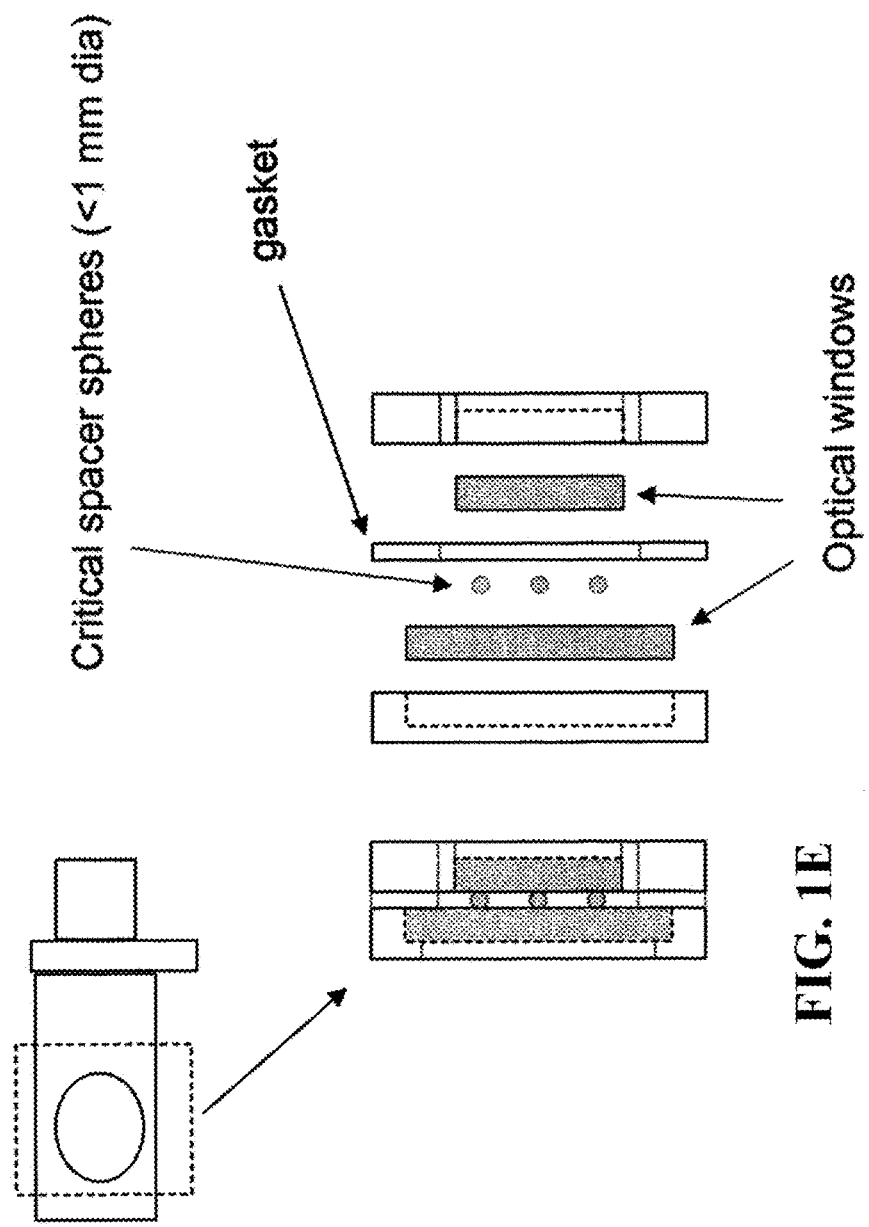
FIG. 1E shows a schematic of reference assembly elements that can be used with embodiments of the invention.
Figure 1F:
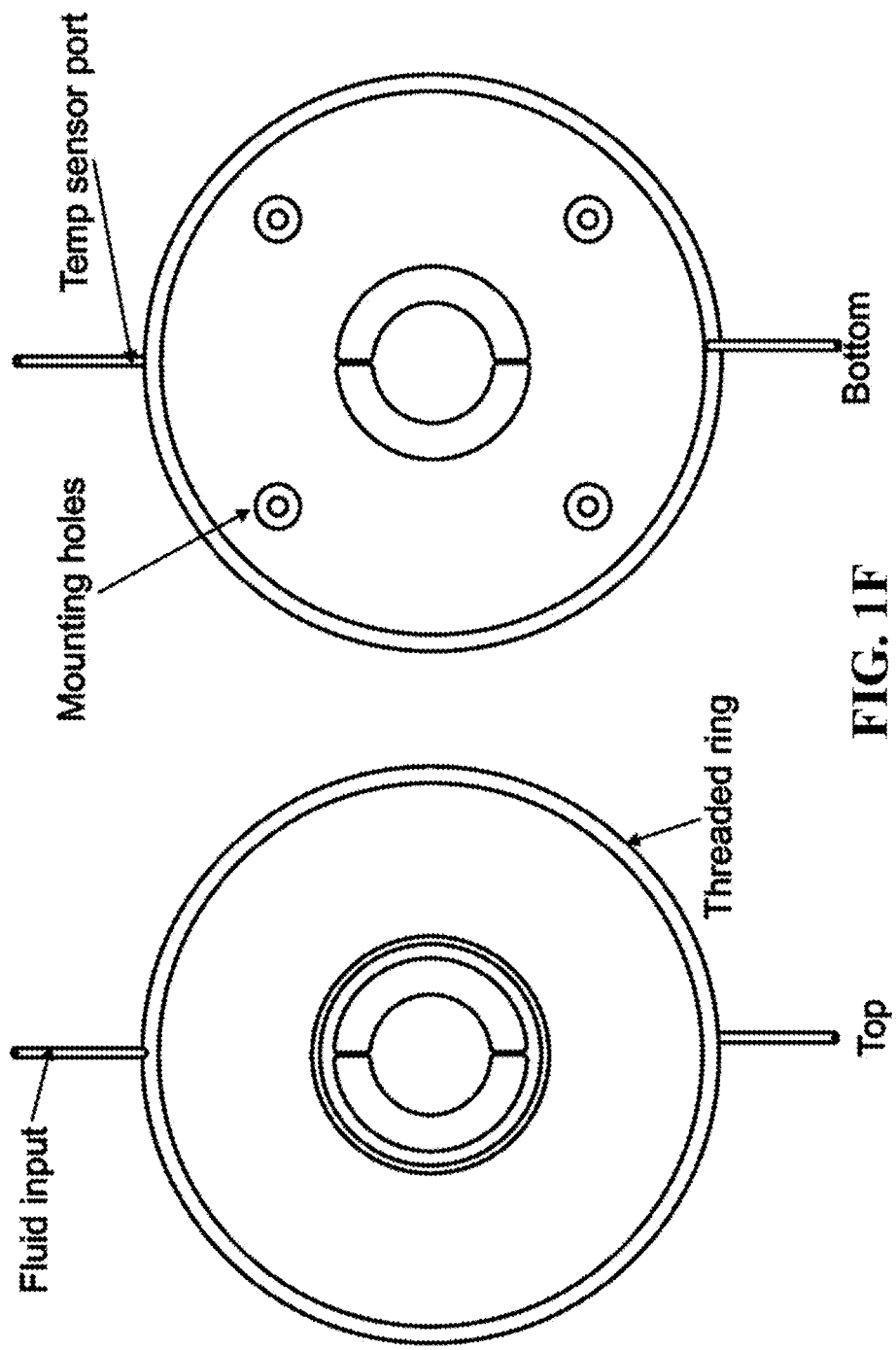
FIG. 1F shows photographs of non-magnetic steel sample assembly elements that can be used with embodiments of the invention.
Figure 1G:
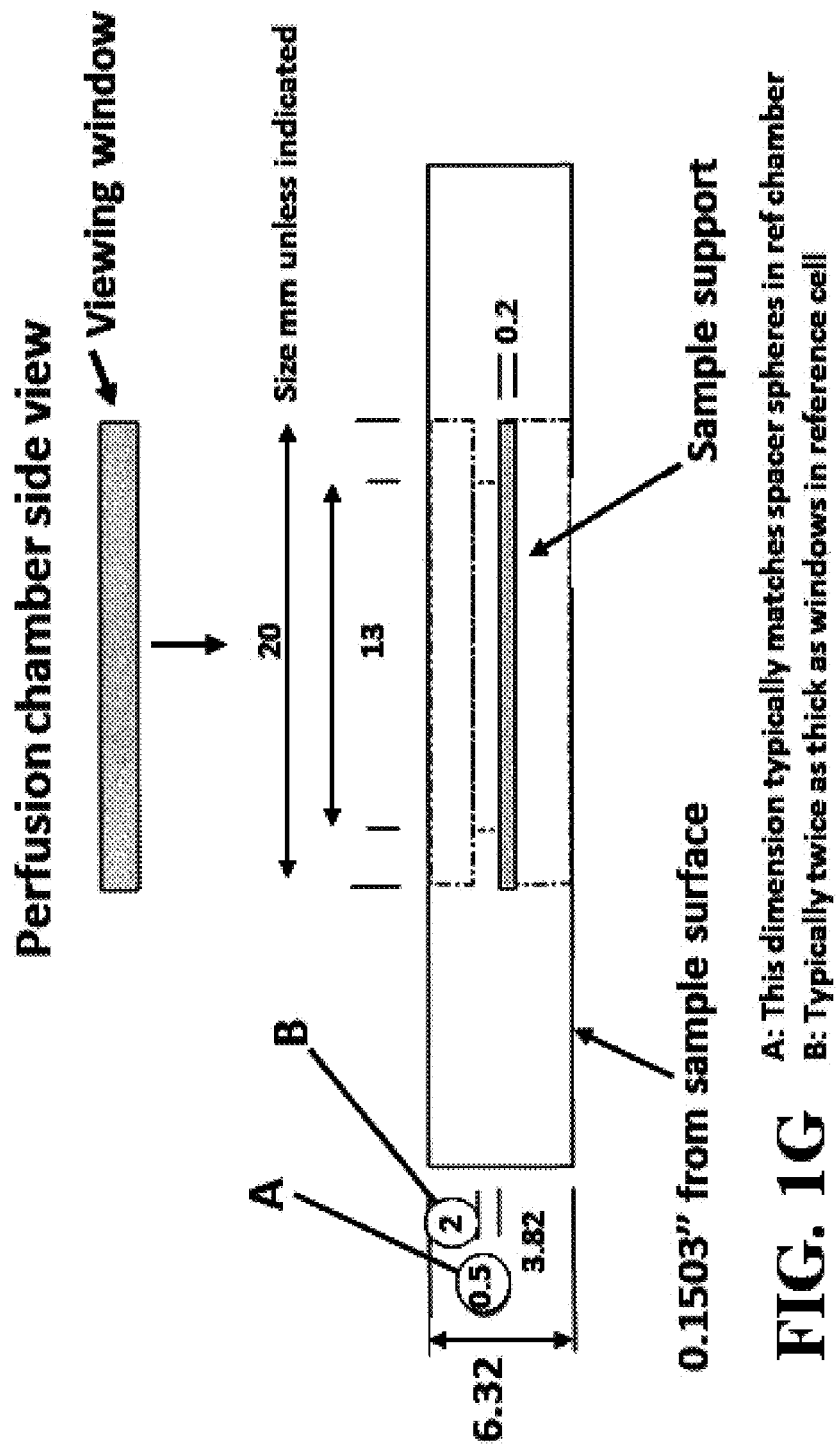
FIG. 1G shows a schematic of sample assembly elements that can be used with embodiments of the invention.
Figure 2A:
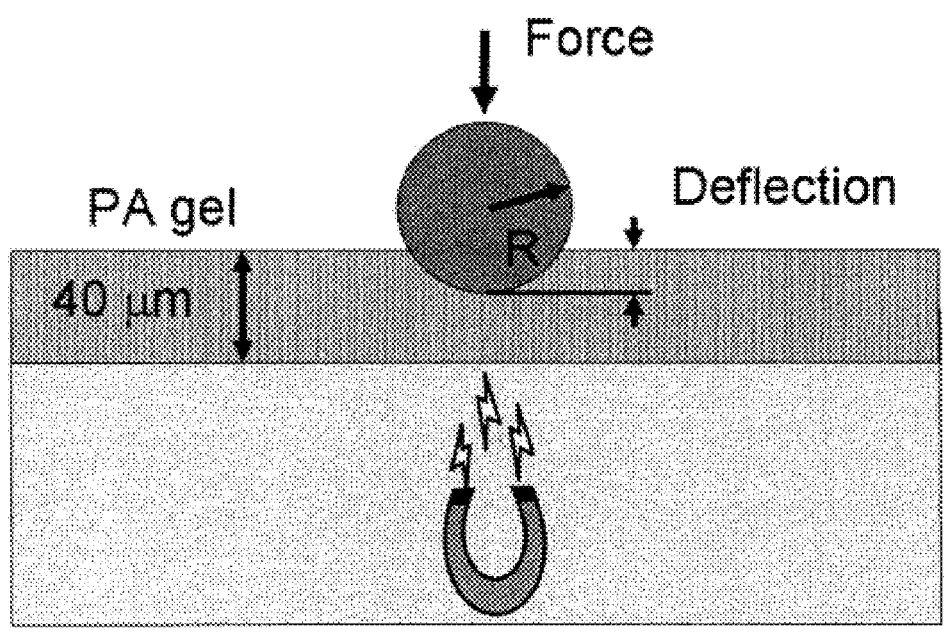
FIG. 2A shows a schematic of the geometry of the force-indentation tests using a 40 μm thick polyacrylamide (PA) gel to simulate the cell body.
Figure 2B:
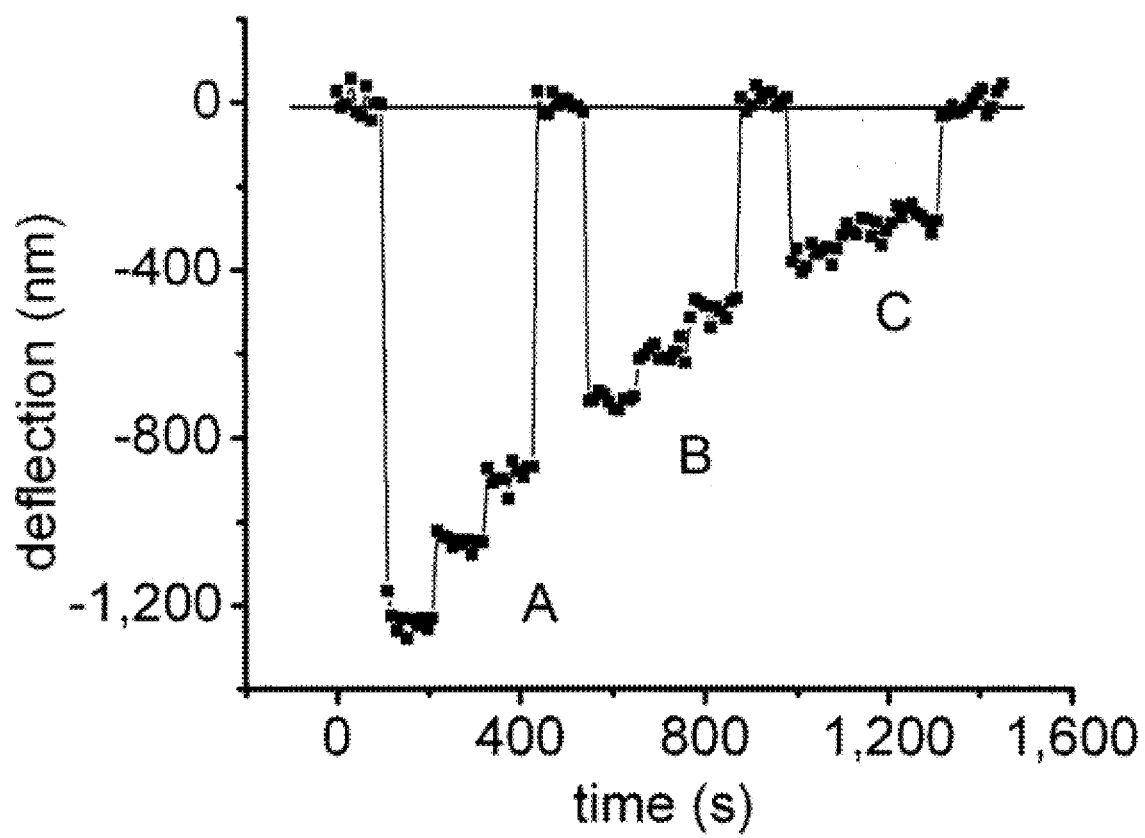
FIG. 2B provides a graph of a showing the deflection of a 7 μm nickel microreflector into a 0.05% crosslinker PA gel, under a series of decreasing forces; A- 6.6, 5.3 and 4.2 nN; B- 4.2, 3.3, 2.8 nN; C- 2.4, 1.9 and 1.6 nN. Force-distance measurement can be fitted to the Hertz contact model for a spherical indenter, from which the gel's elastic modulus is calculated.
Figure 2C:
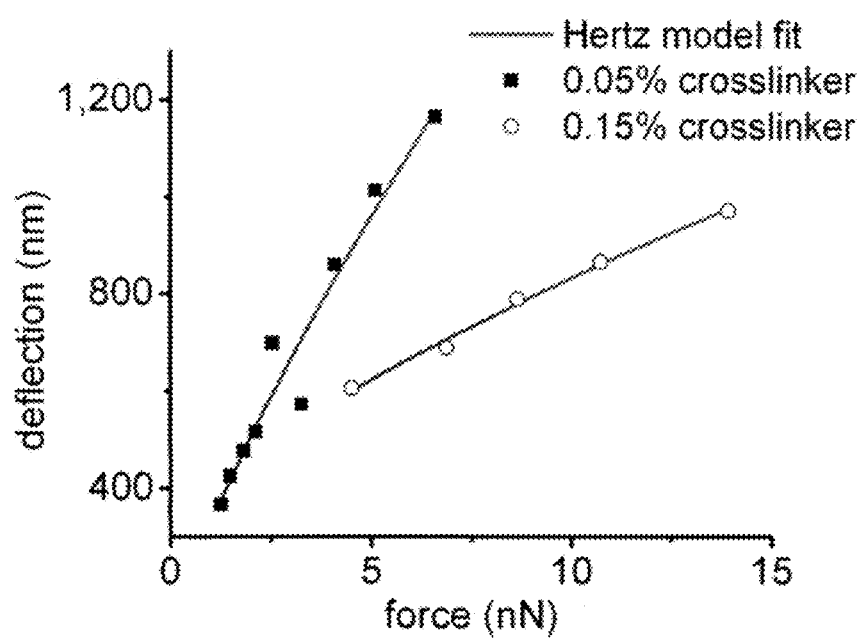
FIG. 2C provides individual measurements on a 0.05% and a 0.15% crosslinker gel show the correspondence between the force-deflection behavior of the microreflectors and that predicted by the Hertz model.
Figure 2D:
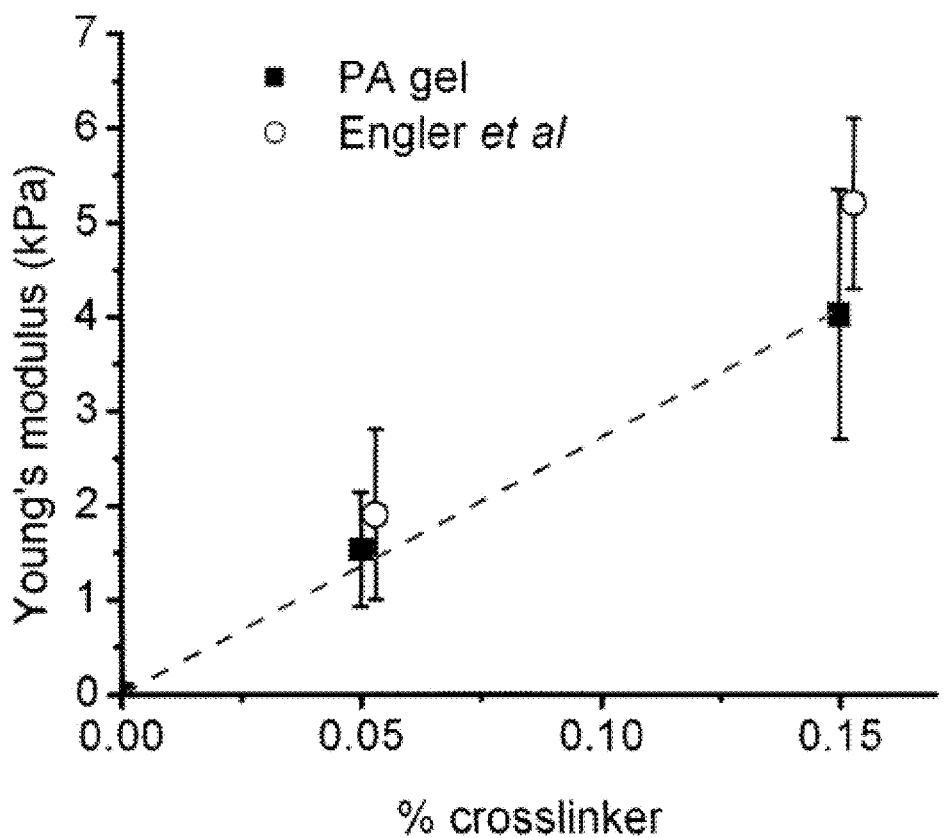
FIG. 2D provides a graph showing that the measured values for Young's modulus were linearly proportional to the crosslinker concentration, as expected, and the range of absolute values (1,530+/−600 Pa and 4,020+/−1,300 Pa) agree well with similar measurements by others using AFM and bulk techniques (see, e.g. Mahaffy et al., (2004) Biophysical Journal 86, 1777-1793; Mahaffy et al., (2000) Physical Review Letters 85, 880-883; Engler et al., (2004) Biophysical Journal 86, 617-628).

Unless otherwise defined, all terms of art, notations and other scientific terms or terminology used herein are intended to have the meanings commonly understood by those of skill in the art to which this invention pertains. In some cases, terms with commonly understood meanings may be defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art. As appropriate, procedures involving the use of commercially available kits and reagents are generally carried out in accordance with manufacturer defined protocols and/or parameters unless otherwise noted. A number of terms are defined below.

As used herein, the term "membrane" refers to a barrier between the cytoplasm of a cell and the extracellular environment, or between the interior of a subcellular organelle and the cytoplasm of a cell. A "membrane" includes a eukaryotic animal, fungal, or yeast cell membrane or cell wall, which generally comprises a lipid bilayer and may include other components such as polypeptides, glycoproteins, lipoproteins, and polysaccharides; a plant cell wall, which generally comprises cellulose, and other components such as lignin, pectins, and hemi-celluloses; a bacterial cell wall (including cell walls of archaebacteria and eubacteria); and the like. Membranes include artificial as well as naturally-occurring membranes, such as external cell membranes, nuclear membranes, mitochondrial membranes, and the membranes of other organelles. In embodiments of the invention, many structures can be imaged in isolation and/or within a live cell by changing plane of focus (e.g. because membranes are not completely opaque compared with surrounding liquid environments).

The term, "cell characteristic" is used according to its art accepted meaning and includes for example the biological state of a cell and/or the cell type of a cell and/or a cell's response to a biochemical event. Typically such characteristics can be correlated with one or more physiological phenomena such as oncogenic transformation. Membrane movement of the cell is one cellular characteristic that can be observed and then correlated with physiological phenomena. "Biological state" (or "physiological status") includes, but is not limited to, the status of a cell in response to one or more stimuli, controlled cell division (e.g., mitosis); uncontrolled cell division (e.g., cancerous state); active protein synthesis; quiescence; apoptosis; adhesion to a surface; metastasis; and the like.

"Cell type" refers to the role that a cell plays under normal physiological conditions. Non-limiting examples of cells are cells of multicellular organisms, e.g., cells of invertebrates and vertebrates, such as myoblasts, neutrophils, erythrocytes, osteoblasts, chondrocytes, basophils, eosinophils, adipocytes, invertebrate neurons (e.g., *Helix aspera*), vertebrate neurons, mammalian neurons, adrenomedullary cells, melanocytes, epithelial cells, and endothelial cells; tumor cells of all types (e.g., melanoma, myeloid leukemia, carcinomas of the lung, breast, ovaries, colon, kidney, prostate, pancreas and testes); cardiomyocytes, endothelial cells, lymphocytes (e.g. T-cells and B cells), mast cells, vascular intimal cells, hepatocytes, leukocytes including mononuclear leukocytes; stem cells such as hematopoietic stem cells, neural, skin, lung, kidney, liver and myocyte stem cells; osteoclasts, connective tissue cells, keratinocytes, melanocytes, hepatocytes, and kidney cells. Suitable cells also include known cell lines, including, but not limited to, Jurkat T cells, NIH3T3 cells, CHO, COS, etc. Cell lines include those found in ATCC Cell Lines and Hybridomas (8th ed, 1994, or latest edition, or on the world wide web at www.atcc.org), Bacteria and Bacteriophages (19th ed., 1996), Yeast (1995), Mycology and Botany (19th ed., 1996), and Protists: Algae and Protozoa (18th ed., 1993), available from American Type Culture Co. (Manassas, Va.). In certain embodiments, a specific lineage of cells noted above such as muscle cells are specifically excluded from an analysis, e.g., the cell is not a muscle cell. In certain embodiments, transformed eukaryotic cell lines, such as HEK293 cells, are specifically excluded from an analysis.

The term "biological sample" is used according to its art accepted meaning and encompasses for example biological materials (typically containing cells) that are examined in a wide variety of diagnostic and/or monitoring assays known in the art. The definition encompasses in vitro samples such as cell cultures and related samples as well as in vivo samples such as those obtained from blood and other liquid samples of biological origin, solid tissue samples such as biopsy specimens or cells derived therefrom and the progeny thereof. The definition also includes samples that have been manipulated in any way after their procurement, such as by treatment with reagents, solubilization, or enrichment for certain components, such as polynucleotides or polypeptides. The term "biological sample" encompasses a clinical sample, and also includes cells in culture, cell supernatants, cell lysates, serum, plasma, biological fluid, and tissue samples.

The terms "cancer," "neoplasm," and "tumor" are used interchangeably herein to refer to cells which exhibit relatively autonomous growth, so that they exhibit an aberrant growth phenotype characterized by a significant loss of control of cell proliferation and/or extended survival. Cancerous cells are malignant, whereas a tumor or neoplasm can be benign or malignant.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims. It must also be noted that as used herein and in the appended claims, the singular forms "a", "and", and "the" include plural referents unless the context clearly dictates otherwise. Thus, for example, reference to "a micromirror" includes a plurality of such micromirrors and equivalents thereof known to those skilled in the art, and so forth. All numbers recited in the specification and associated claims that refer to values that can be numerically characterized with a value other than a whole number (e.g. the concentration of a compound in a solution) are understood to be modified by the term "about". Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

All publications mentioned herein are incorporated herein by reference to disclose and describe the methods and/or materials in connection with which the publications are cited. Publications cited herein are cited for their disclosure prior to the filing date of the present application. Nothing here is to be construed as an admission that the inventors are not entitled to antedate the publications by virtue of an earlier priority date or prior date of invention. Further the actual publication dates may be different from those shown and require independent verification.

The invention disclosed herein has a number of embodiments. Embodiments of the invention provide methods, materials and systems for observing and/or characterizing one or more properties of a deformable composition such as the membrane of a cell. Illustrative embodiments of the invention comprise using interferometry to detect a movement of a membrane of the cell in order to obtain information on and/or characterize one or more cellular properties. Illustrative cellular properties that can be observed by embodiments of the invention can include for example cytoskeletal remodeling behavior in response to a stimulus, for example a stimulus comprising exposure to a drug or other biologically active agent as well as a variety of other factors. In some embodiments of the invention, the phenomena that is observed is one corresponding to, or associated with, a pathological condition such as aberrant cell division, such as occurs in precancerous and cancerous cells. In some embodiments of the invention, the cell membrane in which movement is observed is a membrane of a single cell. In other embodiments of the invention, the membrane properties of a plurality of cells are observed. In certain embodiments, the membrane is a membrane of a cell in a tissue. In other embodiments, the membrane is a membrane of a cell within a colony of cells (e.g. an in vitro cell culture of primary cells taken from a patient or an established cell line). In typical embodiments of the invention, the cell is a eukaryotic (e.g. mammalian) cell.

Embodiments of the invention can use a variety of optical profiling methods to observe and/or characterize one or more properties of a deformable composition. Such methods can comprise for example comparing information derived from a scanning interferometry signal for a first surface location of a test object (e.g. a mammalian cell) to information corresponding to multiple models of the test object. The multiple models can then be parameterized by a series of characteristics for the test object. The derivable information compared in such systems can relate to a shape of the scanning interferometry signal for the first surface location of the test object (e.g. the height of a cell or a population of cells above a matrix). Such optical profiling methods are typically interferometric, however non-interferometric optical profiling methods can also be used in embodiments of the invention.

In typical interferometric embodiments of the invention, an interferometer uses, for example, a Mirau, Michelson or Linnik configuration. Certain embodiments of the invention can use objectives with specific characteristics such as a transmissive media (TTM) interference objective. In addition, methods and elements associated with interferometric technologies including spectrally resolved interferometry, wavelength scanning interferometry, digital holography and the like can be used in embodiments of the invention. While many interferometric microscopy systems and methods can be adapted for use with embodiments of the invention, other embodiments of the invention can use scanning optical microscopes, confocal microscopes and the like. An illustrative and non-limiting list of publications that describe optical profiling methods and materials that can be adapted for use with embodiments of the invention are disclosed for example in U.S. Patent Application Nos. 20050248770; 20050225769; 20050200856; 20050195405; 20050122527; 20050088663; 20040252310; 20050117165; 20030234936; 20040066520; 20080018966 and 20050167578, the contents of which are incorporated by reference.

Embodiments of the invention use optical profilometry techniques to provide for example methods of height measurement, shape measurement, as well as measures of other modulations in the shapes of cell membranes and other deformable materials. Depending on the shape, size and material of a test object such as a cell or a population off cells, these techniques typically use structured light, focusing properties of optics, interference of light, etc., to optimize results in an economical and practical way. Moire' techniques, ESPI (electronic speckle-pattern interferometry), laser scanning, photogrammetry, and interferometry are illustrative techniques developed for conducting three-dimensional shape measurements. The technique of white-light vertical scanning interferometry (VSI) is used to provide data shown in FIG. 3A. VSI, also commonly referred to as white-light interferometry or coherence radar, is used for imaging small objects, typically those with roughness that does not exceed a few micrometers. VSI methodology is based on detection of the coherence peak created by two interfering, polychromatic wavefronts. It has many advantages such as absolute depth discrimination, fast measurement cycle, and high vertical resolution. One advantage of VSI is the ease with which it can be combined with other measurement techniques, such as phase-shifting interferometry (PSI), which are superior in accuracy but may lack the scanning depth of VSI. PSI is typically used for measurements of smooth surfaces with small changes in profile (see K. Creath, "Temporal Phase Measurement Methods," Interferogram Analysis, Institute of Physics Publishing Ltd., Bristol, 1993, pp. 94-140). VSI is generally used to measure smooth and/or rough surfaces with large interpixel height ranges (K. G. Larkin, "Efficient Nonlinear Algorithm for Envelope Detection in White Light Interferometry," J. Opt. Soc. Am., A/Vol. 13, 832-843 (1996). The combination of VSI and PSI has been used, for example, to measure large steps with PSI precision (C. Ai, U.S. Pat. No. 5,471,303). The PSIOTF technique, which is a particular case of VSI and PSI combination, improves measurements of smooth surfaces in the larger height range (see, e.g. Harasaki et al., "Improved Vertical Scanning Interferometry," Appl. Opt. 39, 2107-2115, 2000). Typical VSI and PSI systems and methods are disclosed for example in U.S. Pat. Nos. 5,133,601, 5,471,303 and U.S. Pat. No. 6,449,048, and U.S. Patent Application No. 20020196450, the contents of which are incorporated by reference.

Embodiments of the invention include systems and/or methods for observing a property of a deformable material comprising: a microscope capable of measuring a feature of interest in a sample; a detector operatively coupled to the microscope; a sample assembly comprising an observation chamber adapted to contain the deformable material; and a plurality of reflective microparticles capable of adhering to the deformable material, wherein the average diameter of the reflective microparticles is between 0.5 µm and 30 µm. In certain embodiments, the microscope is a confocal microscope. In other embodiments, the microscope is an interference microscope capable of observing interference fringes and the system further comprises a reference assembly adapted to substantially match an optical path length of the sample assembly. The systems and/or methods of the invention can be used to obtain a variety of types of information, for example information relating to an axial position of a magnetic reflective microparticle coating or proximal to a deformable material; and/or information relating to a z motion of a magnetic reflective microparticle coating or proximal to the deformable material. In addition, certain embodiments of systems and/or methods disclosed herein comprise optical profiling techniques such as confocal or digital holography, spectrally resolved interferometry, wavelength scanning interferometry, digital holography and the like.

One embodiment of the invention is a system for observing a property of a deformable material comprising: a microscope; a detector such as a point detector, a line detector, a microbolometer or a camera (e.g. a still camera, a video camera, charge coupled devices (CCD) other image capture devices used microscopy and/or the observation of deformable compositions such as cell membranes) operatively coupled to the microscope; a sample assembly comprising an observation chamber adapted to contain the deformable material; a reference assembly comprising a reference chamber; a plurality of reflective magnetic microparticles capable of adhering to the deformable material; and a magnet disposed below the observation chamber and oriented coaxially with an optical axis; wherein the magnet is operatively coupled to a motorized micrometer and adapted to exert a magnetic force on a magnetic reflective microparticle adhered to the surface of the deformable material. Embodiments of the invention further include methods for observing a property of a deformable material using the systems disclosed herein. While cellular membranes are the focus of the disclosure provided herein, those of skill in the art understand that a wide variety of other deformable materials can be observed and/or characterized using embodiments of the invention disclosed herein (e.g. the polymeric acrylamide materials observed in the Examples below). In addition, while many embodiments of the invention use cells coated with micromirrors (e.g. spherical magnetic micromirrors), others do not. Such embodiments include for example observations of membranes that are not coated with micromirrors where membrane motion is observed with real-time phase measurements of factors such as optical cell thickness (cell density), cell volume and the like. These embodiments of the invention use the system and methodological elements disclosed simply in the absence of the micromirrors. One such method is a method for observing a property of a cell (and/or a population of cells), the method comprising placing the cell in a cell observation chamber of an optical microscope having a Michelson interference objective; and using this Michelson interference objective to observe the movement of the cell. Other embodiments of the invention can use a Mirau and/or Linnik interferometric objective system. Typically in such embodiments, the movement the cell correlates to a property of the cell such as cell density and/or cell volume and the like, and in this way the methods allow a property of the cell to be observed.

Embodiments of the invention include a system for obtaining an image of a cell comprising: an interference microscope capable of extracting information from interferometric fringes; a detector operatively coupled to the interference microscope; a sample assembly comprising an observation chamber adapted to contain the cell, a reference assembly adapted to substantially match an optical path length of the sample assembly, and a plurality of reflective microparticles capable of adhering to the cell, wherein the average diameter of the reflective microparticles is between 0.5 mm and 30 mm. One typical embodiment of the invention is a system for obtaining an image of a cell comprising: a microscope having a Michelson interference objective; a camera operatively coupled to the microscope; a sample assembly comprising an observation chamber adapted to contain the cell; a reference assembly comprising a reference chamber adapted to contain a fluid (e.g. the media disposed in the observation chamber, RPMI, PBS, water or the like); and a plurality of reflective microparticles capable of adhering to the cell, wherein the average diameter of the reflective microparticles is between 0.5 μm and 30 μm (e.g. spherical magnetic microparticles having an average diameter of between 1 μm and 15 μm, between 5 μm and 10 μm etc.). Optionally the reflective microparticles comprise a gradient index (GRIN) spherical lens.

Embodiments of the system are adapted to use a variety elements and methods known in the art and/or described herein. For example, while he sample and/or reference chambers typically include a fluid, other embodiments such that do not need a fluid cell, e.g. a transmissive media (TTM) objective (e.g. by using a salt) can also be used in embodiments of the invention. Moreover, in certain embodiments of the invention, the sample chamber hold the cell is closed while in other embodiments the cell chamber can be open on top (i.e. does not need a lid). Embodiments of the invention typically include matching the optical path difference between the arms of an interferometric system, typically by controlling the sizes and architecture of the elements that make up the sample and reference assemblies. For example, in certain embodiments of the invention, the reference assembly further comprises: a first optical window; a first housing element adapted to hold the first optical window; a second optical window; a second housing element adapted to hold the second optical window; and a plurality of spherical spacer elements disposable between the first optical window and the second optical window and adapted to separate the first and second optical windows to a defined distance. This is merely an illustrative and non-limiting example of one way of accomplishing this goal, and there are a variety of other ways to match the optical path difference between the arms etc. (e.g. in an embodiment where just one plate that matches the cell chamber, two wedges can shifted with respect to each other so that the optical path is varied, different types of spacers can be used instead of spherical spacer elements etc.).

In embodiments of the invention the sample assembly can further comprise: a viewing window and a first housing element adapted to hold the viewing window, wherein the thickness of the viewing window is equivalent to the combined thickness of the first and second optical windows in the reference assembly. Moreover, in such embodiments of the invention the sample assembly can also comprise a plurality of spherical spacer elements disposable between the viewing window and a top portion of the observation chamber and adapted to separate the viewing window and the top portion of the observation chamber to a defined distance that is equivalent to the defined distance between the first and second optical windows in the reference assembly (see, e.g. the schematic representations of such assemblies shown in FIGS. 1A-1F). In typical embodiments of the invention, a surface of the observation chamber is reflective.

Embodiments of the invention include a variety of permutations of these systems. For example, in certain embodiments, the observation chamber comprises at least one perfusion conduit adapted to circulate a cell media within the chamber. Some embodiments of the invention also include a magnet disposed below the observation chamber and oriented coaxially with an optical axis. Typically in such embodiments, the magnet is operatively coupled to a motorized micrometer and adapted to exert a magnetic force of between 0 Newtons and 5 nanoNewtons (e.g. 0 to 250 pN, 250 pN to 1 nanoN, etc.) on a magnetic reflective microparticle adhered to the surface of the cell. In some embodiments of the invention, the magnet can be adapted to generate a magnetic field of between 200 Gauss and 3 kiloGauss. In embodiments of the invention, the magnet can also be adapted to generate a magnetic field gradient range of between 300,000 to 800,000 Gauss/meter. Typical embodiments of the invention further comprise a processor element and a memory storage element adapted to process and store one or more images of the cell. In certain embodiments of the invention, the cell is labelled with another marker/probe known in the art such as a fluorescent marker (e.g. green fluorescent protein) and the system includes optical elements adapted to image these labelled cells. Some embodiments of the invention include additional elements used to observe cellular properties such as devices and processes (e.g. software based processes) used in FT infrared spectroscopy, Raman spectroscopy and the like.

Related embodiments of the invention include methods of using the systems disclosed herein. One such embodiment of the invention is method for observing a property of a cell, the method comprising: adhering a reflective magnetic microparticle to the cell; placing the cell in a cell observation chamber of an optical microscope having a Michelson interference objective; exposing the cell coated with the microparticle to a magnetic field; and then using the Michelson interference objective to observe the movement of the microparticle adhered to the cell in response to the applied magnetic field, wherein the movement of the reflective microparticle adhered to the cell correlates to a property of the cell, so that a property of the cell is observed.

A variety of methodological embodiments are contemplated. For example, certain methodological embodiments of the invention are performed using a system comprising: a camera operatively coupled to the microscope; a sample assembly comprising an observation chamber adapted to contain the cell; a reference assembly comprising a reference chamber adapted to contain a fluid; a memory storage element adapted to store one or more images of the cell; and a processor element adapted to process one or more images of the cell.

The methods of the invention can be used to obtain a wide variety of information relating to one or more cellular properties. For example, in certain embodiments of the invention, the method can be used for example to observe an optical thickness of a live cell in an aqueous medium. Embodiments of the invention can be used to measure the optical thickness of a live cell in liquid (i.e. culture medium) to 1 nm vertical resolution with an image capture rate of 1 every 11 secs (can be increased to 1 in $1/1000$th of a second with modifications) for all cells in the field of view. This observation provides useful information and comprises, for example, a measure of the proteins, nucleic acids and other molecules in the cell that retard the return of the interferometer light back to the CCD detector camera on a pixel-by-pixel basis across the horizontal axis of a cell body within the field of view.

Alternatively, the method can be used to observe a cell mass property of a live cell in an aqueous medium. For example, cell mass in liquid can be calculated for each cell from observations obtained from embodiments of the systems disclosed herein. By collecting such calculations over a period of time, adaptive and/or maladaptive changes in cell optical thickness (mass) can be evaluated in response to environmental (i.e. drugs, cytokines) or cell internal (i.e. genetic manipulations by RNAi, gene knockout, over-expression technologies) alterations. For example, one can use measurements of the motion(s) of one or more optically reflective object(s) (i.e. beads, mirrors) on the surface of a cell and for all cells within the field of view in a resting state, to observe response to drugs, genetic alterations, and/or in response to magnetic force application. From this information, one can then, for example, derive biophysical parameters for each cell in the field, such as viscoelasticity (typically using certain calculations known in the art and/or disclosed in the Examples below). In this way, artisans can observe cell properties under changing conditions over time.

In yet another embodiment of the invention cell motion "signatures" can be derived for each individual cell in a population at rest or in response to a perturbation. Motion can be parameterized across a cell body, or almost instantaneous measurements of strain across a cell can be made. Transient versus permanent alterations in cell appearance and optical thickness can be determined from perturbations. Cell exhaustion (no more responses) and death (by incorporating immunofluorescence-detecting objectives and vital stains such as AnnexinV and/or propidium iodide and others) can be evaluated by repeat or extreme stimulations. The cell cycle can (in concept) be visualized and biophysical properties evaluated (i.e. by force required to indent the cell membrane with a reflector during cell division).

In yet another embodiment of the invention, individual live cells with unique properties can be isolated and recovered from the field of view because their position(s) are identified in the interferometer field of view. Further manipulations such as recovering an observed cell for additional analyses are contemplated. Recovery can be with a suction pipette, for example, to allow further studies (i.e. adoptive transfer into small animals, further testing in a variety of settings, such as single cell microarray gene expression profiling etc.).

As noted above, in some embodiments of the invention, the method is used to observe a viscoelastic property of a live cell in an aqueous medium. Optionally, the method is used to observe a population of live cells, for example to observe resting and dynamic responses to stimuli in a population of live cells. In certain embodiments of the invention, resting and/or dynamic responses of a plurality of cells in a population of live cells can be measured simultaneously. Typically in these methods, the property is observed in response to the cell's exposure to a stimulus such as the magnetic field applied to the cell and/or a composition introduced into the cell's media. Optionally the methods further comprise removing the cell from the observation chamber and manipulating the cell for a further analysis. In certain embodiments of the invention, the method is used to obtain information comprising a cell specific profile of a live cell in an aqueous medium and to then store this information in the memory storage element.

Figure 13A:
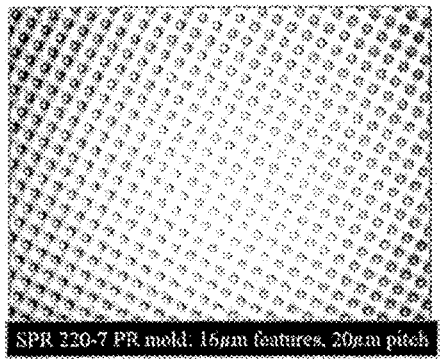
FIGS. 13A and 13B show photographs of cellular environments that can be used with embodiments of the invention and can be made for example by photoresist deposition processes known in the art. Such environments (with "holes" (e.g. nanowells or microwells) of an appropriate size) can create structures that facilitate uniform cell packing analysis. In these FIG. 13B, cells labeled 1, 2, 3 are in 10 micron-sized wells.
Figure 13B:
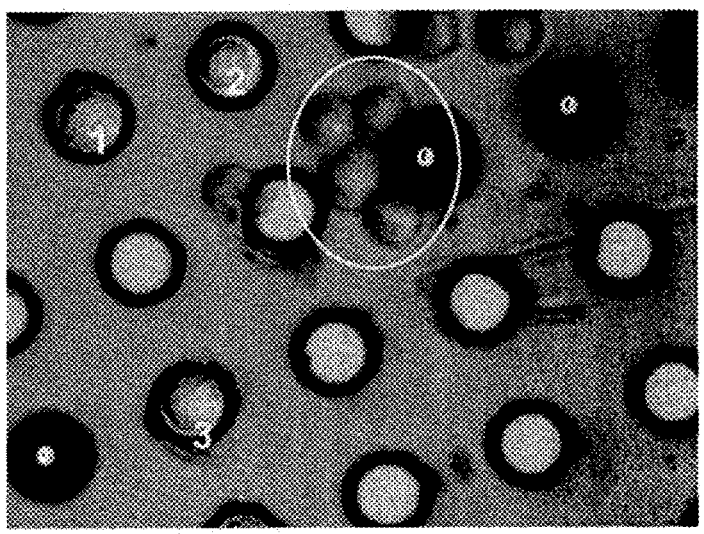
Figure 14A:
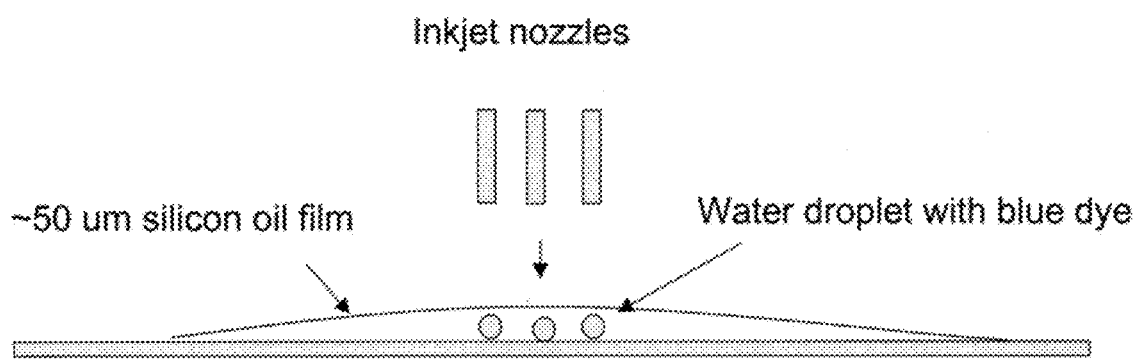
FIG. 14A shows a schematic of one illustrative way to fabricate micromirrors/reflectors from curable polymers.
Figure 14B:
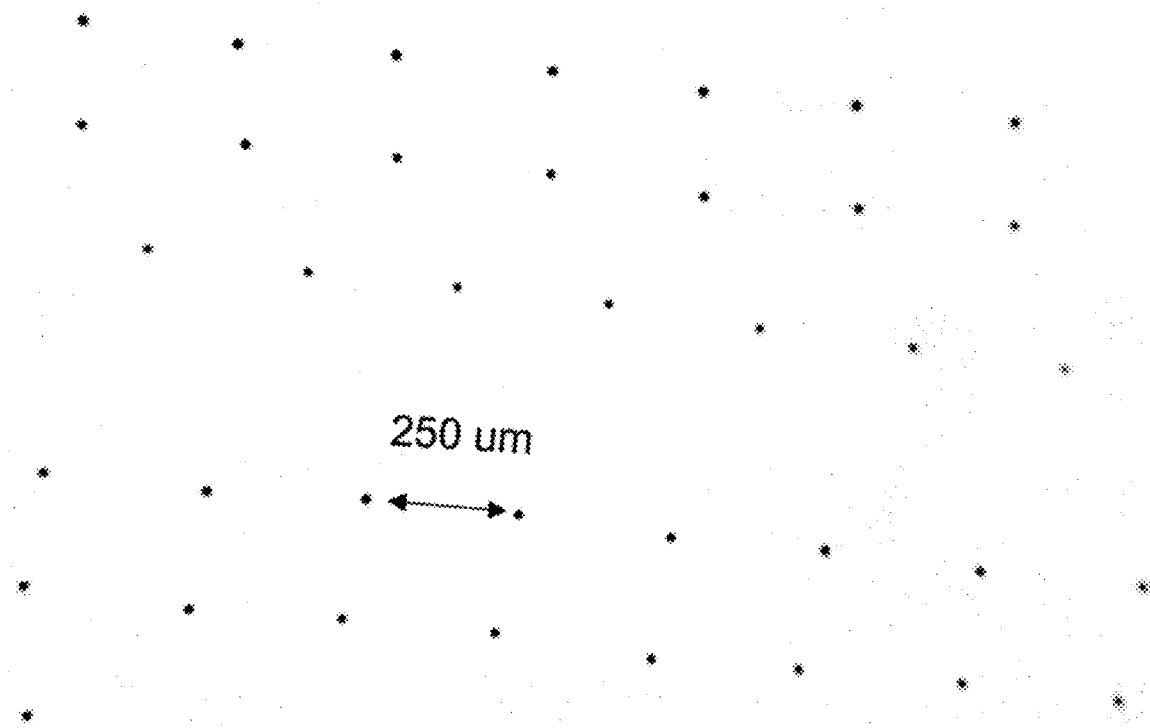
FIG. 14B shows a photograph of reflectors fabricated in this manner.
Figure 14C:
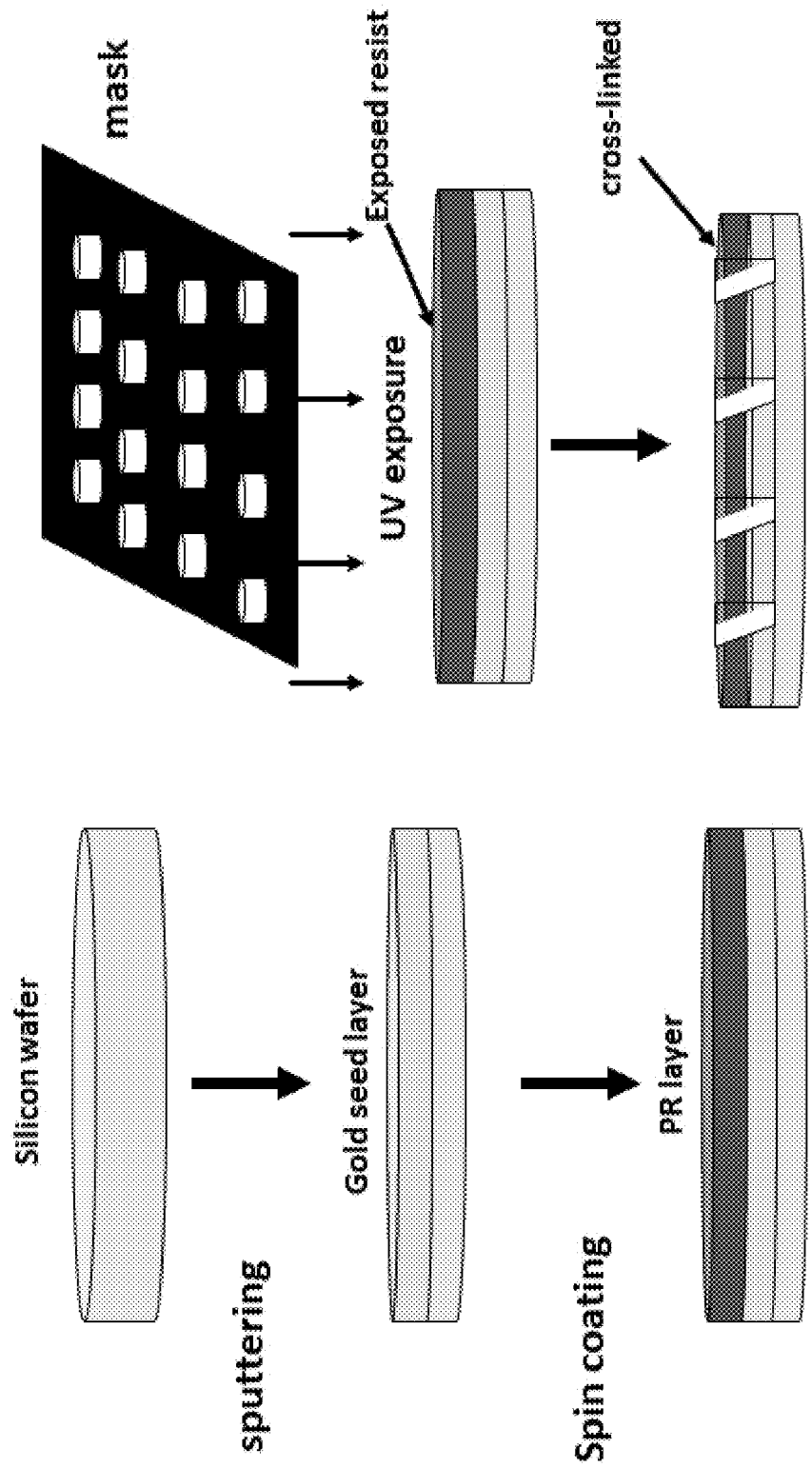
FIGS. 14C-14E show schematics of other processes known in the art (e.g. sputtering, spin coating, photoresist and electroplating technologies etc.) that can be used to generate micromirrors/reflector embodiments of the invention.
Figure 14D:
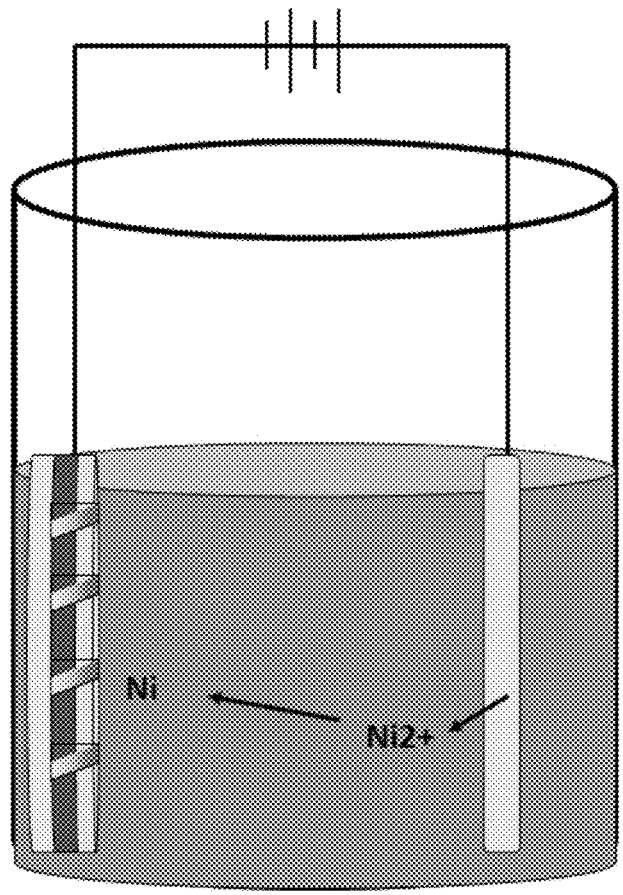
Figure 14E:
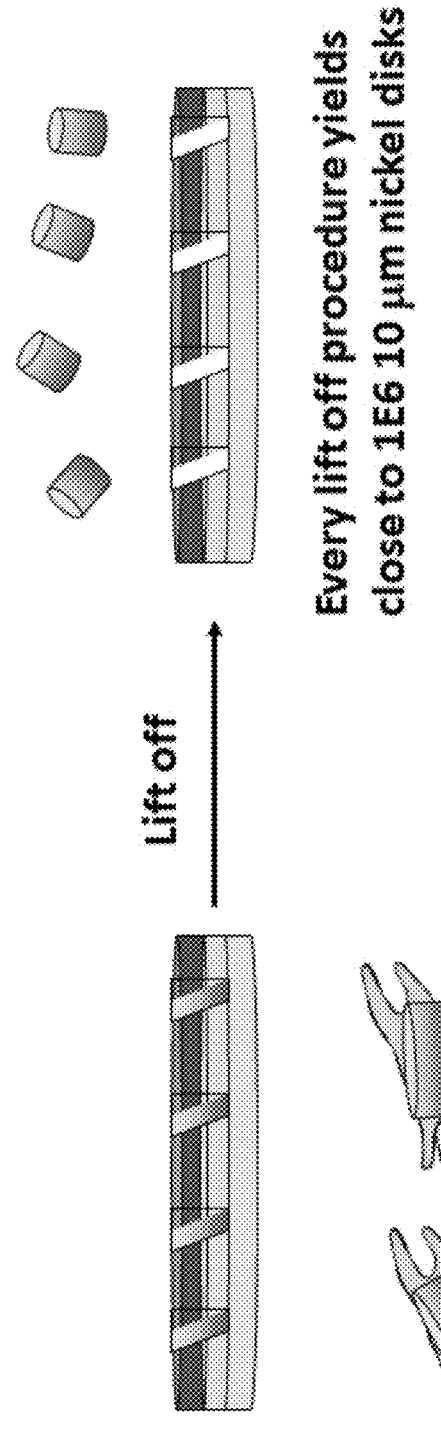

In some embodiments of the invention, cells can be arrayed for more uniform, higher density, and higher throughput analysis (e.g. by photoresist deposition processes known in the art) with "holes" (e.g. nanowells or microwells) of an appropriate size (see, e.g. FIGS. 13A and 13B). In this context, microreflector placement on the surface of cells can be guided/enhanced by manufacture that is less than the size of a well, creating a sort of "piston-like" action that eliminates many issues related to exact reflector placement on the surface of each individual cell.

Embodiments of the invention also include a reflective microparticle comprising a gradient index (GRIN) spherical lens. Typically this microparticle is coupled to a flexible tether and/or an optical fiber and/or is operatively coupled to an endoscope. In certain embodiments of the invention, this microparticle comprises a plurality of material layers, wherein refractive indices of the material layers decrease from the center of the microparticle.

Further aspects, elements, and processes associated with embodiments of the invention are disclosed below.

ILLUSTRATIVE METHODOLOGICAL EMBODIMENTS OF THE INVENTION

The invention disclosed herein has a number of methodological embodiments. Typical embodiments of the invention comprise a method for determining one or more characteristics of one or more cells including the steps of directing an incident beam of light on the cell, wherein the cell comprises a subject micromirror positioned on the cell surface; and then detecting a beam of light reflected from the micromirror, to detect a movement of the membrane of the cell. In some embodiments, the membrane movement detected is in response to an external stimulus (e.g. a factor delivered into the liquid medium environment in which the cell is disposed). In other embodiments, the membrane movement is in response to an internal stimulus.

Embodiments of the invention further include a method for determining a cell characteristic by detecting membrane movement in a plurality of cells. The method comprises contacting each cell of a plurality of cells with a micromirror probe and then detecting movement of the probes (e.g. in response to various forces and/or stimuli). In some of these embodiments, a plurality of tests (e.g. in the form of an array) is performed. In some embodiments of the invention, the method further comprises allowing a signal resulting from membrane movement of a first cell in a plurality of cells in response to a stimulus to be transmitted to a second cell in the plurality of cells; and then detecting movement of a membrane in the second cell in response to the transmitted signal.

In embodiments of the invention where a cell is in a liquid medium, an external stimulus can added to the medium, and the response of the cell, as detected by membrane movement, to the external stimulus is monitored. In other embodiments, where the external stimulus is a condition such as heat, cold, radiation, etc., the condition of the cell's environment is adjusted. The methods are useful for detecting changes in a cell even before the change is detectable visually. For example, a cancerous cell is detected even before the cell undergoes characteristic morphological changes that are visible when viewed under a microscope (e.g., by a clinician). In these embodiments, a cancerous state in a cell is detected in vitro in a biological sample (e.g., a cervical swab, or other tissue biopsy sample) by detecting cell membrane movement, and comparing the movement of the cell membrane with the cell membrane movement characteristic of a normal cell of the same cell type. In this manner, cancerous cells can be detected at a much earlier stage than with means currently available to the clinician.

Another embodiment of the invention is a method of identifying an agent that affects a biological activity of a cell, the method generally involving contacting a cell with a test agent, and determining the effect, if any, of the agent on the biological activity of the cell, wherein the determining comprises detecting cell membrane movement. Another embodiment of the invention is a method of identifying a characteristic of a test cell, the method generally involving: determining a cell characteristic profile of the test cell to generate a test profile, wherein the cell characteristic profile comprises cell membrane movement data and at least one additional cell parameter; and comparing the test profile with a reference profile in a database of profiles, wherein this comparison can be used to identify a reference profile that is similar or substantially identical to the test profile, and wherein the reference profile identifies the cell characteristic. In certain embodiments of the invention, the reference profile indicates that the test cell is abnormal (e.g. a cell in a tissue biopsy from a patient suspected of having a cancer). Another embodiment of the invention is a method for screening for the presence of a biologically active agent in a sample (e.g. a ligand that binds to a receptor expressed on the surface of a cell), the method generally involving: contacting a cell with a test sample suspected of containing an agent; and determining the effect, if any, of the test sample on the cell membrane movement of the cell.

As noted above, in typical embodiments of the invention, membrane movement is detected using an Michelson interferometer. This membrane movement is used as a read-out for a cell's response to a biochemical event and/or the physiological status of a cell and/or the cell type. Embodiments of this method allow for real-time monitoring of a cell's response to an internal or external stimulus. Embodiments of the invention include methods for determining a characteristic of a cell, such as cell type, cellular response to a biochemical event, and biological state. These methods typically involve detecting membrane movement in a cell and then using the movement detected by this method to obtain information on a cell characteristic. The methods of the invention are useful for applications such as the screening of biologically active (e.g. therapeutic) agents as well as diagnostic applications such as identifying a cell having one or more characteristics associated with a pathological condition such as cancer. Certain embodiments of the invention include methodological steps that employ one or more databases of cell characteristics, as known in the art and/or as determined using the disclosed methods and systems.

As noted above, embodiments of the invention provide methods of determining a characteristic of a cell, typically a living cell. The method generally involves detecting movement of a cell membrane, and relating the movement to a cell characteristic. Membrane movement is detected using a system that includes at least a membrane movement responsive element (e.g. a microsphere) and a detection element for detecting a signal generated by the responsive element (e.g. an interferometer). The system may further include other elements known in the art, such as a data storage means for storing the signal; and a data processing means, for converting the signal to various formats, for comparing the signal to other stored signals, etc.

A typical method for observing membrane movement includes contacting the membrane with a micromirror element that responds to membrane movement and provides a detectable signal in response to-membrane movement. The signal is then transmitted or detected by a detection element. The signal detected by the detection element is transmitted to a data processing and storage means, e.g. a computer system. The system may also include an element for transmitting a signal to a cell membrane. Membrane movement includes, but is not limited to, lateral movement, stretching, contracting, and the like.

Embodiments of the invention can be used to detect membrane movement in a variety of cells (including naturally-occurring cells and artificial cells) as well as subcellular organelles. Cells that can be examined by embodiments of the invention include eukaryotic cells; prokaryotic cells; and artificial cells. Eukaryotic cells include mammalian cells, reptilian cells, amphibian cells, yeast cells, plant cells, protozoan cells, algae, and the like. Subcellular organelles include the nucleus, mitochondria, Golgi apparatus, vacuoles, and the like. Prokaryotic cells include bacterial cells (e.g., eubacteria), and archaebacterial cells. Cells and cellular environments that can be examined by embodiments of the invention include cells in vitro and in vivo, e.g., isolated cells in vitro; cells in colonies in vitro; cells in tissues in vitro; single cells in vivo; cells in tissues in vivo; unicellular organisms; cells of multicellular organisms; and the like.

Embodiments of the invention can be used to detect membrane movement associated with biochemical events. Biochemical events include internal stimuli; external stimuli; gene expression; and the like. Movement of the membrane is detected in response to a change in physiological conditions in the cell or organelle. Changes in physiological status are generally in response to an internal or an external signal. External and internal signals (stimuli) include, but are not limited to, infection of a cell by a microorganism, including, but not limited to, a bacterium (e.g., *Mycobacterium* spp., *Shigella*, *Chlamydia*, and the like), a protozoan (e.g., *Trypanosoma* spp., *Plasmodium* spp., *Toxoplasma* spp., and the like), a fungus, a yeast (e.g., *Candida* spp.), or a virus (including viruses that infect mammalian cells, such as human immunodeficiency virus, foot and mouth disease virus, Epstein-Barr virus, and the like; viruses that infect plant cells; etc.); change in pH of the medium in which a cell is maintained or a change in internal pH; excessive heat relative to the normal range for the cell or the multicellular organism; excessive cold relative to the normal range for the cell or the multicellular organism; an effector molecule such as a hormone, a cytokine, a chemokine, a neurotransmitter; an ingested or applied drug; a ligand for a cell-surface receptor; a ligand for a receptor that exists internally in a cell, e.g., a nuclear receptor; hypoxia; a change in cyoskeleton structure; light; dark; mitogens, including, but not limited to, lipopolysaccharide (LPS), pokeweed mitogen; stress; antigens; sleep pattern (e.g., sleep deprivation, alteration in sleep pattern, and the like); an apoptosis-inducing signal; electrical charge (e.g., a voltage signal); ion concentration of the medium in which a cell is maintained, or an internal ion concentration, exemplary ions including sodium ions, potassium ions, chloride ions, calcium ions, and the like; presence or absence of a nutrient; metal ions; a transcription factor; a tumor suppressor; cell-cell contact; adhesion to a surface; peptide aptamers; RNA aptamers; intrabodies; and the like.

Responses to internal stimuli that can be observed using embodiments of the method can include the expression of a gene, and/or production of a gene product. Production of a gene product includes expression of an endogenous gene, as well as the expression of an introduced nucleic acid. In some embodiments, a nucleic acid comprising a nucleotide sequence encoding a protein of interest is introduced into a cell, generating a genetically modified cell, the nucleic acid is expressed, the protein is produced in the genetically modified cell, and the response of the genetically modified cell to the protein is detected. In one embodiment, the nucleic acid encodes a nucleic acid that affects transcription of a gene. Such nucleic acids include antisense nucleic acids, ribozymes, and inhibitory RNA (RNAi) (including double stranded RNAi).

Embodiments of the invention can be used to detect the presence and/or level of one or more proteins of interest. In some embodiments, the protein of interest is an exogenous protein, e.g., a protein that the cell does not normally produce because the cell does not possess a nucleic acid encoding such a protein (or possesses a nucleic acid that does not express that protein). In other embodiments, the protein of interest is one that a normal cell of the same cell type would normally produce, but that the cell cannot produce because of some defect in the cell. For example, the cell's genome may contain a mutation in the coding region and/or regulatory region of a gene such that a given protein is not produced. Alternatively, the cell's genome may contain a defect in a coding region and/or regulatory region in a gene other than the gene encoding the protein of interest, and introduction of the nucleic acid encoding the protein of interest circumvents the defect. For example, the cell may contain a mutation in a gene encoding a transcription factor necessary for production of the protein of interest, such that the transcription factor is either not produced or is produced in an inactive form, and a nucleic acid is introduced which encodes the protein of interest under control of a promoter not regulated by the absent or defective transcription factor. In other embodiments, the protein of interest is a dominant negative mutant, e.g., a protein that, when produced, prevents a counterpart normal protein that is produced by the cell from functioning, or reduces the function of the normal protein. In other embodiments, the protein is an endogenous protein that the cell produces at low levels, and introduction of a nucleic acid encoding the protein results in overproduction of the protein. In these embodiments, the coding region of the protein of interest is operably linked to a promoter element. Constitutive promoters that are active in most eukaryotic cell are well known in the art, and include, but are not limited to, human cytomegalovirus immediate early promoter, adenovirus major late promoter, an SV40 virus promoter, a Rous sarcoma virus promoter, and a murine 3-phosphoglycerate kinase promoter. The nucleotide sequence encoding the protein of interest can also be under transcriptional control of an inducible promoter, e.g., a promoter that can be activated by an inducer; a repressible promoter, or a developmentally regulated promoter. For example, where the nucleotide sequence encoding the protein of interest can be under transcriptional control of an inducible promoter, an external signal includes an inducer of an inducible promoter. Inducible promoters, and their inducers, are well known in the art, and include, but are not limited to, cold-inducible promoters; heat-inducible promoters; metal ion inducible promoters; a tetracycline-inducible promoter; a radiation-inducible promoter; a drug-inducible promoter; a hormone-inducible promoter; and the like. In these embodiments, the nucleic acid is introduced into the cell, and the inducing agent is added to the medium, or the cell is exposed to the inducing condition which results in expression of that gene (e.g., a chemical inducer, heat, cold, radiation, etc.).

The methods of the invention find use in a variety of applications, including drug screening, detection assays, and diagnostic assays. The invention provides screening assays for identifying agents that affect a cell process and/or physiological status. The invention further provides assays for detecting the presence of an analyte in a test sample. The methods generally involve contacting a cell with a test agent; and detecting any change in cell membrane movement in response to the test agent. For example, an agent that inhibits mitosis, and which therefore may be of use in treating cancer, is identified by monitoring cell membrane movement that is characteristic of a cell undergoing mitosis.

The terms "candidate agent," "agent," "substance," and "compound" are used interchangeably herein. Test agents encompass numerous chemical classes, typically synthetic, semi-synthetic, or naturally-occurring inorganic or organic molecules. Test agents may be small organic compounds having a molecular weight of more than 50 and less than about 2,500 daltons. Test agents may comprise functional groups necessary for structural interaction with proteins, particularly hydrogen bonding, and may include at least an amine, carbonyl, hydroxyl or carboxyl group, and may contain at least two of the functional chemical groups. The test agents may comprise cyclical carbon or heterocyclic structures and/or aromatic or polyaromatic structures substituted with one or more of the above functional groups. Test agents are also found among biomolecules including peptides, saccharides, fatty acids, steroids, purines, pyrimidines, derivatives, structural analogs or combinations thereof.

Test agents include those found in large libraries of synthetic or natural compounds. For example, synthetic compound libraries are commercially available from Maybridge Chemical Co. (Trevillet, Cornwall, UK), ComGenex (South San Francisco, Calif.), and MicroSource (New Milford, Conn.). A chemical library is available from Aldrich (Milwaukee, Wis.). Alternatively, libraries of natural compounds in the form of bacterial, fungal, plant and animal extracts are available from Pan Labs (Bothell, Wash.) or are readily producible. Additionally, natural or synthetically produced libraries and compounds are readily modified through conventional chemical, physical and biochemical means, and may be used to produce combinatorial libraries. Libraries of test agents also include cDNA libraries, e.g., expression libraries from a given cell type, from a cell in response to an agent, from a cell of a given physiological status (e.g., a cancerous cell), and the like. In addition, known pharmacological agents may be subjected to directed or random chemical modifications, such as acylation, alkylation, esterification, amidification, etc. to produce structural analogs. New potential therapeutic agents may also be created using methods such as rational drug design or computer modeling.

Assays of the invention include controls, where suitable controls include a sample (e.g., a cell sample) in the absence of the test agent or other condition. Generally, a plurality of assay mixtures is run in parallel with different agent concentrations to obtain a differential response to the various concentrations. Typically, one of these concentrations serves as a negative control, i.e. at zero concentration or below the level of detection.

Agents that have an effect in an assay method of the invention may be further tested for cytotoxicity, bioavailability, and the like, using well known assays. Agents that have an effect in an assay method of the invention may be subjected to directed or random and/or directed chemical modifications, such as acylation, alkylation, esterification, amidification, etc. to produce structural analogs. Such structural analogs include those that increase bioavailability, and/or reduced cytotoxicity. Those skilled in the art can readily envision and generate a wide variety of structural analogs, and test them for desired properties such as increased bioavailability and/or reduced cytotoxicity and/or ability to cross the blood-brain barrier. The components of the assay mixture are typically added in any order that provides for the requisite binding or other activity. Incubations are performed at any suitable temperature, typically between 4° C. and 40° C. Incubation periods are selected for optimum activity, but may also be optimized to facilitate rapid high-throughput screening. Typically between 0.1 and 1 hour will be sufficient.

In many embodiments, an array of isolated cells or colonies of cells is used, wherein each isolated cell or colony of cells is contacted with a test agent, and the effect on the cells is determined by contacting the cells or cell colony with a micromirror and examining one or more characteristics of the cell(s) via interferometry. In some embodiments, a cellular array is addressable, such that the identity of each isolated cell/cell colony is known and can be matched to the cell's reaction to the test agent. For example, cells are deposited on discrete regions (e.g., microwells) of a solid substrate, and each microwell contains a unique identifier that corresponds to the identity of the cells in the microwell. Alternatively, the cells themselves are coated with at least one optically interrogatable material, such as a bioluminescent compound, a chemiluminescent compound, a chromophore, a fluorophore, etc. (see, e.g., U.S. Pat. No. 6,377,721, the contents of which are incorporated by reference).

The invention further provides assays for detecting the presence of an analyte in a test sample. The methods generally involve contacting a cell with a test sample; and detecting any change in cell membrane movement in response to the test sample. Such a screening assay is useful to detect the presence in a sample of an biologically active agent suspected to exist in the sample, e.g., a subject screening assay can be used to detect the presence in a sample of a toxin or a toxic bacterium, e.g., an environmental agent (e.g., a pesticide, an herbicide, an environmental toxin, and the like), an agent of chemical or biological warfare (e.g., nerve gas, anthrax, etc.). Assays of the invention include controls, where suitable controls include a sample (e.g., a cell sample) in the absence of the test sample. Generally a plurality of assay mixtures is run in parallel with different known concentrations of the agent being detected to obtain a differential response to the various concentrations. Typically, one of these concentrations serves as a negative control, i.e. at zero concentration or below the level of detection. The assay methods provide for qualitative (e.g., presence or absence), semi-quantitative, and quantitative detection of analyte. Where the methods are quantitative, the response of a cell membrane to a test sample is compared to a standard curve obtained using known concentrations of the analyte, and the presence and concentration of the analyte are determined.

As an example, the methods of the invention are useful for detecting the presence in a tissue or a biological sample of a cell that is abnormal. Because the cell membrane movement is characteristic for a given cell type, and also for cancerous cells of a given cell type, determination of the cell membrane movement of a given cell provides information as to whether the cell is undergoing mitosis at a rate characteristic for the cell type, or is dividing in an uncontrolled manner, e.g., is cancerous. The methods are also useful for providing the cell type of the cancerous cell. The methods are further useful for staging the cancer. In this context, the invention further provides a method of treating a disease or disorder. The methods generally involve identifying a characteristic of a cell, which characteristic indicates that the cell is abnormal; and recommending and/or selecting a treatment regimen appropriate to the abnormality. For example, where a cell in a tissue biopsy is determined to be a cancerous cell, a treatment regimen appropriate to the particular type of cancer is recommended. In some embodiments, as discussed above, the methods provide for staging of the cancer. A course of chemotherapy or radiation therapy appropriate to the stage of the cancer is then recommended.

Embodiments of the invention useful for identifying a characteristic of a test cell can be coupled to computer systems and databases. Methods for identifying a characteristic of a test cell generally involve determining a cell characteristic profile of the test cell to generate a test profile, and comparing the test profile with a reference profile in a subject database. Such methods further include the generation of a library of profiles (e.g. one grouped according to specific physiological conditions associated with various profiles) as well as comparisons of a test profile to profiles in a library of profiles. Such comparisons can use software processes known in the art to provide the best match, e.g., to identify a reference profile that is substantially identical to the test profile. The reference profile can then be used to correlate one or more characteristics of the test cell (e.g. disregulated cell growth).

The cell characteristic profiles can be compiled in a database, as described above, and the information in the database is used to compare the profile of a test cell to a reference profile in the database. The comparison can be made by trained personnel (e.g., a clinician, a technician, etc.), or can be made by a computer or other machine. The subject diagnostic assays are useful for identifying any type of abnormal cell, for example, diagnostic assays of the invention are useful for identifying cancerous cells in a biological sample, e.g., a biopsy, as well as in an individual in vivo.

The data obtained from analysis of various cell types under various physiological conditions and in various physiological states can be compiled in a database in order to, for example, train neural networks for independent detection of cell types and physiological status of cells. The cell characteristic profiles are obtained as described above, and the neural network is trained to recognize cells of various cell types, cells in various physiological states, and cells responding to various stimuli. The neural network is useful for identifying cancerous cells, pre-cancerous cells, and cells in other pathological conditions.

Illustrative Systems and Materials Used with Embodiments of the Invention

Embodiments of the invention include systems for determining a characteristic of a cell. A typical system generally includes at least a membrane movement responsive element (e.g. a micromirror); and a detection element for detecting a signal generated by the responsive element (e.g. an interferometer) as well as a data storage and processing means, for storing the signal, for converting the signal to various formats, for comparing the signal to other stored signals, etc. Data storage and processing means are computer-based systems, as described below. In some embodiments, where the detection system involves use of a micromirror attached to a cell surface, a subject system includes a light source (e.g., a LED), a sensor, such as a CCD, and data storage and processing means.

Interferometry Systems

Interferometry is the technique of diagnosing the properties of two or more optical waves by studying the pattern of interference created by their superposition. The Michelson interferometer is a common configuration for optical interferometric device. In such devices, an interference pattern is produced by splitting a beam of light into two paths, bouncing the beams back and recombining them. Art in the field of interferometry teaches that different paths may be of different lengths or be composed of different materials to create alternating interference fringes on a detector. A variety of interferometers and interferometry systems known in the art can be used and/or adapted for use with embodiments of the invention. Typical interferometers and interferometry systems include those disclosed in Basics of Interferometry, Second Edition by P. Hariharan (2006); Optical Interferometry, Second Edition by P. Hariharan (2003); Two-Dimensional Phase Unwrapping: Theory, Algorithms, and Software by Dennis C. Ghiglia and Mark D. Pritt; U.S. Pat. Nos. 7,505,863; 7,212,356; 6,624,893; 6,459,489; 7,522,282; and 7,492,462 and U.S. Patent Application Nos. 20070076208; 20080218999; 20030004412; and 20050190372, the contents of each of which is incorporated by reference herein.

Probes

Embodiments of the invention include a probe that is operatively coupled to the membrane of one or more cells (e.g. a micromirror such as the micrometer sized elemental nickel microspheres disclosed in the Examples below). The probe typically is of a radius such that movement of a membrane of a cell that correlates with one or more physiological phenomena can be readily detected (e.g. spherical magnetic microparticles having an average diameter of between 1 μm and 15 μm).

As noted above, typical embodiments of the invention provide a method for determining a cell characteristic, involving monitoring the movement of a mirror attached to the cell surface. Use of a mirror attached to a cell surface is particularly useful for analyzing soft cells, such as mammalian cells. For example, where the cell characteristic is determined by monitoring cell membrane movement, cell membrane movement is analyzed by detecting movement of a mirror (also referred to herein as a "reflector," a "micromirror") attached to the surface of the cell. As used herein, the term "reflector" is used to denote a body which reflects a portion of the electromagnetic radiation incident on the body. An incident beam of light is reflected by the mirror. Movement of the mirror is detected by a sensor which detects the reflected beam of light.

Optionally such micromirrors further comprise a cell attachment surface, wherein the surface area of the micromirror is in a range of from about 25 nm$^2$ to about 75μ$^2$. In some embodiments, the reflector surface can comprise a diffraction grating. In some embodiments, the cell attachment surface of the micromirror comprises a cell attachment moiety immobilized on the cell attachment surface. Typical cell moieties include, e.g., an antibody, a polypeptide, an integrin, a virus attachment protein, a carbohydrate, and a ligand for a cell surface receptor.

Embodiments of the invention can be used to detect vertical or lateral movement of a cell membrane of from about 0.1 nm to about 500 nm, e.g., from about 0.1 nm to about 1 nm, from about 1 nm to about 5 nm, e.g., from about 5 nm to about 10 nm, from about 10 nm to about 50 nm, from about 50 nm to about 100 nm, from about 100 nm to about 250 nm, or from about 250 nm to about 500 nm. Embodiments of the invention can detect movement at a frequency of from about 1 Hz to about 10 KHz, e.g., from about 1 Hz to about 10 Hz, from about 10 Hz to about 50 Hz, from about 50 Hz to about 100 Hz, from about 100 Hz to about 500 Hz, from about 500 Hz to about 1 kHz, or from about 1 kHz to about 10 kHz. The data can be expressed as vertical (or lateral) displacement versus time. In certain embodiments, the data are treated with a Fourier Transform (FT) to generate an amplitude spectrum. In embodiments of the invention, measurements of membrane movement can made at regular intervals (e.g., every 1, 5, 10, 30 seconds, or 60 seconds, and/or 2, 3, 4, 5, 6, 7, 8, 9 or 10 minutes, 15 minutes, etc.); or continuously. Alternatively, measurements of membrane movement are made at a single time point (e.g. a predetermined or random time point).

Where the response of a cell to an external stimulus is analyzed in vitro, the external stimulus is added to the cell medium, as described above. In some embodiments, an external stimulus is added to the medium in which a cell is being analyzed (e.g., cell culture medium, bodily fluid, etc.). In other embodiments, the external stimulus is delivered by the probe itself (e.g. a probe coated with an agent of interest such as a biologically active agent). In these embodiments, the probe can be functionalized or adapted to deliver the signal. In these embodiments, a stimulus is attached to the probe. For example, a drug, a hormone, a nucleic acid, or other signal is attached to the probe, and when the probe contacts the membrane, the stimulus is delivered to the cell. The stimulus can be linked to the probe either covalently or non-covalently.

Alternatively, the probe is fitted with an element that delivers the stimulus. For example, a single or multiwall carbon nanotube is attached to the probe, and an external stimulus (e.g., an agent in a liquid formulation) is delivered into the cell (e.g., into the cytoplasm or into the nucleus) by the nanotube. In these embodiments, the stimulus is linked (covalently or non-covalently) to the nanotube. In some embodiments, the stimulus is attached to the nanotube via a linker which is proteolytically cleaved by an intracellular enzyme. In some embodiments, an element for delivering an electrical signal will be attached to the probe, or is positioned adjacent to the probe, such that an electrical signal is delivered to the membrane. In some embodiments, a stimulus that is delivered to the cell membrane is a programmable or pre-recorded pattern that is stored in a data storage medium. For example, a stimulus is delivered to the cell at regular intervals (e.g., to mimic a Circadian rhythm). As another example, a stimulus is delivered to a cell to stimulate entry into the cell cycle at a particular time point, which is pre-recorded.

In some embodiments, movement of a membrane of a first cell is converted into a signal, and transmitted to the membrane of a second cell. In some of these embodiments, the first cell is physically separated from the second cell, e.g., the first cell and the second cell are in separate wells of a multi-well plate. In other embodiments, the first cell and the second cell are in the same tissue or colony, but are separated from one another by other cells and/or extracellular matrices. In other embodiments, the first cell and the second cell are in direct contact with one another. Any movement in a membrane of the second cell in response to the signal transmitted from the first cell can be transmitted to a third cell, and so on.

In some embodiments of the invention, a single probe is in contact with a cell. In other embodiments, two, three, four, or more, individual probes are in contact with a membrane of a cell. For example, individual probes are in contact with different areas of a cell membrane. An example of a situation in which use of multiple probes is useful is in analyzing cells in which different areas of the cell respond differentially to a given stimulus. Non-limiting examples of such cells are polarized cells (e.g., columnar epithelial cells lining the gastrointestinal tract); and cells that have processes that extend from the cell body (e.g., neuron, axons, dendritic cells, etc.).

Embodiments of the invention include the steps of processing data obtained by a detecting device. For example, data transmitted by the position-sensitive detector to the data processor can be formatted in several different ways. In one embodiment, the data can be processed using a Fourier Transformation analysis such as Fourier Transformation Filtering (FTF). The data can also be converted into audio or color format. Conversion into audio format is accomplished using standard audio conversion software, and allows a qualitative measure of the physiological status of a cell. In addition, rather than representing the amplitudes as peaks, color intensities can be used to represent peak intensities, and a plot of each short FTF versus time can be made, resulting in a sonogram. For example, the data can be converted into a usable format in real time using Fourier Transformation Filtering, Audio Files, Color Spectra, and the like.

In embodiments of the invention, the movement of an entire cell can be monitored in vitro. Movement of a cell includes lateral movement and vertical movement. The movement of a cell is in some embodiments monitored in an in vitro culture, wherein the cells are detached from one another. In some embodiments, movement of a cell in an in vitro culture system involves monitoring movement of a cell across a monolayer of adherent cells. In other embodiments, movement of a cell in an in vitro culture system involves monitoring movement of a cell in a tissue. In still other embodiments, movement of a cell in an in vitro culture system involves monitoring adhesion of a first cell to a second cell that comprises on its cell surface a receptor for a ligand present on the surface of the first cell, or that comprises a co-receptor for a receptor present on the surface of the first cell. As one non-limiting example, metastasis of a tumor cell can be monitored in in vitro cell culture assay. As another non-limiting example, leukocyte homing and extravasation can be monitored in an in vitro assay.

In typical embodiments of the invention, light, e.g., light from a LED, a laser beam or any one of the wide variety of optical sources known in the art, is directed onto a mirror attached to the surface of a cell, and a position of reflected light is detected by a sensor. For example, a first position of optical radiation reflected by a mirror attached to a cell surface is detected at a first time (e.g. by a first photograph or the like); and a second position of optical radiation reflected by the mirror is detected at a second time (e.g. by a second photograph or the like). Where the second position differs substantially from the first position indicates movement of the cell membrane (including movement of the entire cell).

Mirrors suitable for attachment to the cell surface are any of a variety of shapes, e.g., circular, oval, flat cylindrical, square, ellipsoid, rectangular, an irregular shape, etc. In many embodiments, a subject micromirror is generally disc shaped. Typically, the surface area of the mirror is less than about 50%, less than about 40%, less than about 30%, less than about 20%, less than about 10%, less than about 5%, less than about 2%, or less than about 1% of the surface area of the cell. For example, in general, the surface area of one group of micromirror embodiments is in a range of from about 75 $nm^2$ to about 25 $\mu m^2$, e.g., from about 75 $nm^2$ to about 100 $nm^2$, from about 100 $nm^2$ to about 150 $nm^2$, from about 150 $nm^2$ to about 200 $nm^2$, from about 200 $nm^2$ to about 500 $nm^2$, from about 500 $nm^2$ to about 750 $nm^2$, from about 750 $nm^2$ to about 1 $\mu m^2$, from about 1 $\mu m^2$ to about 2 $\mu m^2$, from about 2 $\mu m^2$ to about 5 $\mu m^2$, from about 5 $\mu m^2$ to about 10 $\mu m^2$, from about 10 $\mu m^2$ to about 15 $\mu m^2$ from about 15 $\mu m^2$ to about 20 $\mu m^2$, or from about 20 $\mu m^2$ to about 25 $\mu m^2$.

The diameter of a typical mammalian cell ranges from about 3 $\mu m$ to about 11 $\mu m$. In certain embodiments of the invention where the mirror is spherical, and the cell is a mammalian cell, the mirror can have a diameter in the range of from about 10 nm to 30 $\mu m$, e.g., from about 10 nm to about 50 nm, from about 50 nm to about 100 nm, from about 100 nm to about 250 nm, from about 250 nm to about 500 nm, from about 500 nm to about 750 nm, from about 750 nm to about 1 $\mu m$, from about 1 $\mu m$ to about 2 $\mu m$, from about 2 $\mu m$ to about 5 $\mu m$, from about 5 $\mu m$ to about 10 $\mu m$, from about 10 $\mu m$ to about 15 $\mu m$, from about 15 $\mu m$ to about 20 $\mu m$, from about 20 $\mu m$ to about 25 $\mu m$, or from about 25 $\mu m$ to about 30 $\mu m$ etc. The instant disclosure provides evidence that micromirrors used to study live mammalian cells disposed within a observation chamber of an interferometer sample assembly optimally have a diameter in the range within about 0.5 $\mu m$ to 30 $\mu m$ (e.g. 5 $\mu m$ to 15 $\mu m$).

The reflector surface of a subject mirror comprises any of a variety of materials. Suitable materials for the reflector surface include, but are not limited to nickel and other reflective metals and metal alloys, silicon dioxide, polydimethylsiloxane (PDMS), silicon nitride (SiNx), and the like. In some embodiments, a subject mirror comprises biodegradable materials. The reflector surface of a subject mirror will in some embodiments comprise an optical grating texture (a "diffraction grating") that diffracts light. The diffraction grating is in any of a variety of patterns, e.g., a linear array, a radial array, a spiral array, and the like. In addition, the pitch of the grating can vary. See, e.g., "Diffraction Grating" 5th edition, C. Palmer (2004) Spectra-Physics, Inc. For example, the pitch can vary from about 0.1 $\mu m$ to about 10 nm, e.g., from about 0.1 $\mu m$ to about 0.5 $\mu m$, from about 0.5 $\mu m$ to about 1 $\mu m$, from about 1 $\mu m$ to about 10 $\mu m$, from about 10 $\mu m$ to about 50 $\mu m$, from about 50 $\mu m$ to about 100 $\mu m$, from about 100 $\mu m$ to about 500 $\mu m$, from about 500 $\mu m$ to about 1 nm, from about 1 nm to about 5 nm, or from about 5 nm to about 10 nm. In some embodiments, the grating pattern provides information as to the identity of the attachment molecule(s) on the attachment surface of the mirror. Thus, in these embodiments, the diffraction grating pattern provides a code as to the identity of the attachment molecule or combination of attachment molecules on the attachment surface.

Attachment Moieties

The mirror can be attached to the surface of a deformable composition such as a cell membrane by any of a number of interactions, including electrostatic interactions, steric stabilization, van der Waals forces, gravitational forces, frictional forces, covalent linkage, and the like. In some embodiments, an attachment moiety is attached to (immobilized on) an attachment surface of the mirror, where the attachment moiety provides for attachment of the mirror to the cell surface. In some embodiments, an attachment moiety is synthesized directly on the attachment surface of the mirror. See, e.g., U.S. Pat. No. 6,630,308. In other embodiments, a preformed attachment moiety is attached to (immobilized on) the attachment surface by chemical coupling, adsorption or other means. A large number of immobilization techniques have been used and are well known in the fields of solid phase immunoassays, nucleic acid hybridization assays and immobilized enzymes. See, for example, Hermanson, Greg, T. Bioconjugate Techniques. Academic Press, New York. 1995, 785 pp; Hermanson, G. T., Mallia, A. K. & Smith, P. K. Immobilized Affinity Ligand Techniques. Academic Press, New York, (1992) (Chapter 5); and Avidin-Biotin Chemistry: A Handbook. D. Savage, G. Mattson, S. Desai, G. Nielander, S. Morgansen & E. Conklin, Pierce Chemical Company, Rockford Ill., 1992, 467 pp; Protein Immobilization, Fundamentals & Applications, R. F. Taylor, ed. (1991) (chapter 8).

Attachment moieties include a wide variety of biomolecules, including, but not limited to, nucleic acids, including DNA, RNA, oligonucleotides; proteins (including phosphoproteins, lipoproteins, glycoproteins, and the like), peptides, lipids, fatty acids; polysaccharides, oligosaccharides; organic polymers; any of a wide variety of organic molecules which include one or more moieties for binding to a cell surface biomolecule; antibodies; ligands (e.g., agonists for a cell surface receptor, an antagonist for a cell surface receptor); microorganisms; receptors; antibiotics; test compounds (e.g., compounds produced by combinatorial chemistry); bacteria; viruses; and plant and animal cells and organelles or fractions thereof.

An attachment moiety is bound to (immobilized onto) the attachment surface of the mirror. The mirror is bound to the cell surface. The term "bind" includes any physical attachment or close association, which may be permanent or temporary. Generally, an interaction of hydrogen bonding, hydrophobic forces, van der Waals forces, covalent bonding, etc. facilitates physical attachment between the attachment moiety and the attachment surface. Generally, an interaction of hydrogen bonding, hydrophobic forces, van der Waals forces, etc. facilitates physical association between an attachment moiety and a cell surface molecule.

The attachment surface of the mirror comprises any material onto which an attachment moiety can be immobilized, or that can be derivatized or otherwise processed such that an attachment moiety can be immobilized onto the attachment surface. Suitable attachment surface materials include, but are not limited to, polymers, plastics, resins, polysaccharides, silica or silica-based materials, carbon, metals, inorganic glasses, membranes, particles, gels, functionalized glass, germanium, silicon, GaAs, GaP, SiO2, SiN4 modified silicon, polytetrafluoroethylene, polyvinylidenedifluoride, polystyrene, polycarbonate, flat glass, or single-crystal silicon, polytetrafluorethylene, polystyrene, gallium arsenide, or combinations thereof. Suitable polymers include, but are not limited to, (poly)tetrafluoroethylene, (poly)vinylidenedifluoride, polystyrene, polycarbonate, and polymerized Langmuir-Blodgett film.

The attachment surface of a subject mirror is in many embodiments functionalized to include one or more attachment sites for attaching to the cell surface, or for attaching an attachment moiety. Suitable functional groups include, but are not limited to, sulfhydryl groups, and the like. The attachment surface may be coated with a material that facilitates attachment of an attachment moiety. Some solid phase surfaces may be used directly to immobilize an attachment moiety, others must be modified to allow such attachments. For example, antibodies and many other proteins will adhere to clean polystyrene surfaces. Polystyrene, either in the form of microtiter plates or beads, have been modified to bind nucleic acids, proteins, and polysaccharides using techniques that are well known. TEFLON surfaces will bind proteins or other macromolecules that have been suitably fluorinated (see, e.g., U.S. Pat. No. 5,270,193) and will also bind fluorinated surfactants, which may render the surface hydrophilic, or positively or negatively charged. Glass, including controlled pore glass, may be modified to allow covalent attachment of antibodies, antigens or nucleic acids. Plastic or glass surfaces may be modified non-specifically using corona plasma discharge or electron beam radiation and may then be coated with a variety of coatings or adhesives to which an attachment moiety may be attached. More specific covalent attachment of proteins, nucleic acids or carbohydrates may be achieved by a variety of modifications which attach reactive groups to polystyrene or acrylic surfaces, which groups, with or without extending linkers, will then couple under mild conditions to the biopolymers.

In addition to methods by which an attachment moiety is immobilized on a solid surface, general methods exist for immobilizing members of a class of attachment moiety. For example, protein A or protein G may be immobilized and used to subsequently bind specific antibodies which in turn will bind specific ligands. A more general approach is built around the strong and specific reaction between other ligands and receptors such as avidin and biotin. Avidin may be immobilized onto the attachment surface, and used to bind antibodies or other biomolecules to which biotin has been covalently linked. This allows the production of surfaces to which a very wide variety of reactants can be readily and quickly attached (see, e.g. Savage et al., Avidin-Biotin Chemistry: A Handbook. Pierce Chemical Company, 1992).

In some embodiments, the attachment moiety is a first member of a specific binding pair, where the second member of the specific binding pair is displayed on the cell surface. Non-limiting examples of specific binding pairs include selectin/selectin ligand; viral antigen/cell surface receptor; antibody/antigen; receptor/ligand; extracellular matrix/integrin; and the like. Thus, e.g., the first member of a specific binding pair is one or more of the following: an antibody (or an epitope-binding fragment thereof) specific for an epitope displayed on a cell surface; a ligand for a cell surface receptor; a portion of an extracellular matrix molecule that is bound by a cell surface receptor; a carbohydrate moiety that is recognized by a cell surface selectin; and the like.

Viral antigens that are suitable for attachment to the attachment surface of a subject mirror include, but are not limited to, any viral attachment protein, e.g., a viral env protein, a viral spike protein, a viral fusion protein, a viral capsid protein, and the like, including, e.g., human immunodeficiency virus (HIV) gp160 and gp120; human rhinovirus 14; tick-borne encephalitis virus E protein; influenza virus hemagglutinin; respiratory syncytial virus fusion protein F; adenovirus fiber protein; reovirus attachment protein .sigma.1; SARS coronavirus S(S1) protein; herpes simplex virus-1 glycoprotein D; poliovirus capsid shell (VP1, VP2, VP3); and the like. Viral entry proteins are well described in the literature. See, e.g., Dimitrov (2004) Nature 2:109-122. In addition, suitable agonists and antagonists that bind a cell surface receptor include, but are not limited to, hormones;

neurotransmitters; cytokines; chemokines; pharmaceutical agents; derivatives of any of the foregoing that have altered properties compared to a naturally-occurring agonist or antagonist; and the like.

In some embodiments, the attachment moiety is specific to a cell type. In other embodiments, the attachment moiety provides attachment to a wide variety of cells. Non-limiting examples of attachment moieties that are specific to particular cell types include L-selectin ligands, where L-selectin ligands include sulfated forms of GlyCAM-1, CD34 and MAdCAM-1, and where L-selectin is displayed on the surface of leukocytes; E-selectin ligands, where E-selectin ligands tetrasaccharides such as Sialyl-Lewis$^x$ and Sialyl-Lewis$^a$, and cutaneous lymphocyte-associated antigen, and where E-selectin is found on the surface of endothelial cells; and antibodies to cell-specific cell surface molecules. Suitable attachment moieties include proteins bound by cell surface integrins, where suitable attachment moieties include laminin, collagen, fibronectin, tenascin, VCAM-1, MAdCAM-1, ICAM-1, ICAM-2, ICAM-3, fibrinogen, vitronectin, and the like. Suitable attachment moieties include integrins such as $\alpha 4\beta 1$, $\alpha 4\beta 7$, and the like. Suitable attachment moieties include antibodies specific for macromolecules on a cell surface, where exemplary cell surface macromolecules include tumor-associated antigens; cell surface receptors; viral proteins (e.g., viral proteins displayed on the surface of a virus-infected cell); and the like.

In some embodiments, the attachment moiety is an antibody specific for a tumor-associated antigen. Tumor-associated antigens (TAA) include, but are not limited to, MAGE-2, MAGE-3, MUC-1, MUC-2, HER-2, high molecular weight melanoma-associated antigen MAA, GD2, carcinoembryonic antigen (CEA), TAG-72, ovarian-associated antigens OV-TL3 and MOV18, TUAN, alpha-feto protein (AFP), OFP, CA-125, CA-50, CA-19-9, renal tumor-associated antigen G250, EGP-40 (also known as EpCAM), S100 (malignant melanoma-associated antigen), p53, and p21ras.

Typically, the attachment surface comprises a plurality of attachment moieties, e.g., the attachment surface of a single micromirror comprises from about 10 to about $10^{10}$ or more attachment moieties, e.g., from about 10 to about 100, from about $10^2$ to about $10^3$, from about $10^3$ to about $10^4$, from about $10^4$ to about $10^5$, from about $10^5$ to about $10^6$, from about $10^6$ to about $10^7$, from about $10^7$ to about $10^8$, from about $10^8$ to about $10^9$, or from about $10^9$ to about $10^{10}$, or more, attachment moieties.

In some embodiments, the attachment surface comprises a plurality of attachment moieties, wherein the plurality of attachment molecules is homogeneous, e.g., all the attachment molecules on the surface of a single mirror are identical. In other embodiments, the attachment surface comprises a plurality of attachment moieties, wherein the plurality of attachment moieties is heterogeneous, e.g., the plurality of attachment moieties comprises at least two, at least 3, at least 4, at least 5, at least 6, at least 7, at least 8, at least 9, or at least 10, or more, different attachment moieties.

In some embodiments, the attachment moiety itself provides an external stimulus to the cell, and the response of the cell to the attachment moiety is monitored by detecting cell membrane movement. In other embodiments, the attachment surface comprises an attachment moiety; and an agent that provides an external stimulus to the cell.

In some embodiments, a single mirror is attached to a single cell. In other embodiments, a plurality (two or more) of mirrors are attached to a single cell. An example of a situation in which use of multiple mirrors is useful is in analyzing cells in which different areas of the cell respond differentially to a given stimulus. Non-limiting examples of such cells are polarized cells (e.g., columnar epithelial cells lining the gastrointestinal tract); and cells that have processes that extend from the cell body (e.g., neurons, axons, dendritic cells, etc.).

In some embodiments, the invention provides arrays of micromirrors. In some embodiments, each member micromirror in a subject micromirror array comprises an attachment surface with a different attachment moiety from other array members. Mirrors can be purchased from commercial sources (see, e.g. Examples 1 and 2) and/or fabricated using any of a variety of methods known in the art. Suitable techniques include silicon micromachining; SiNx micromachining; contact printing; dip pen lithography; lift off techniques; and the like. In embodiments of the invention, the micromirror comprises one of a wide variety of materials known to be suitable for such elements, for example a metallic material such as nickel or a crystal material such as a silicon composition.

Sensors

Suitable sensors for use with embodiments of the invention include any device that is capable of detecting a reflected beam of light. A wide variety of such sensors are known in the art (see, e.g. U.S. Pat. Nos. 5,233,197 and 7,176,459). Suitable sensors include, but are not limited to, still cameras, video cameras, charge coupled devices (CCD) and the like. The CCD camera is typically connected to an image analysis computer system for data storage and analysis. The scanning process establishes a series of spatial mirror coordinates and mirror types of all the mirrors on the sample. Typical sensors used in embodiments of the invention include those used in a wide variety of interferometric studies and include for example those having the ability to observed fluorescently labelled materials (see, e.g. U.S. Pat. Nos. 7,365,858; 6,381,025; 6,563,105; 7,088,458; and 7,298,496).

In some embodiments of the invention, two-dimensional arrays of micromirrors are used. Arrays of source beams of vertical cavity surface emitting laser (VCSEL) is directed at a two-dimensional array of mirrors. VCSELs can provide a source beam having substantial light intensity, without requiring additional lensing or amplification, in a focused area with low-beam divergence. The deflected beams are identified and detected using a second array of micromirrors which defect the beams to an array of detectors (e.g., a two-dimensional array of photodetectors).

Computer Systems and Databases

Embodiments of the invention comprise databases of profiles of cell characteristics. Such databases will typically comprise profiles of cell membrane movement of various cell types; cell membrane movement of cells of various biological states; and cell membrane movement of cells in response to various biochemical events. A cell membrane characteristic profile will contain, in addition to the cell membrane movement profile, one or more of the following cell parameters: cell type; biochemical event that stimulated the cell membrane movement; cellular environment, e.g., culture conditions, such as media composition and conditions, temperature, pH, osmolarity, as well as the physiological status of the cell. Thus, a typical cell characteristic profile can include the cell membrane movement profile and at least one additional cell parameter. In this context, embodiments of the invention include the generation of a reference library of such images and/or comparing a test image to one or more images in a library of reference images.

The cell characteristic profiles and databases thereof may be provided in a variety of media to facilitate their use. "Media" refers to a manufacture that contains the expression profile information of the present invention. The databases of the present invention can be recorded on computer readable media, e.g. any medium that can be read and accessed directly by a computer. Such media include, but are not limited to: magnetic storage media, such as floppy discs, hard disc storage medium, and magnetic tape; optical storage media such as compact disc read only memory (CD-ROM); electrical storage media such as random access memory (RAM) and ROM; and hybrids of these categories such as magnetic/optical storage media. One of skill in the art can readily appreciate how any of the presently known computer readable media can be used to create a manufacture comprising a recording of the present database information. "Recorded" refers to a process for storing information on computer readable medium, using any such methods as known in the art. Any convenient data storage structure may be chosen, based on the means used to access the stored information. A variety of data processor programs and formats can be used for storage, e.g. word processing text file, database format, etc.

As used herein, "a computer-based system" refers to the hardware means, software means, and data storage and processing means used to analyze the information of the present invention. The minimum hardware of the computer-based systems of the present invention comprises a central processing unit (CPU), input means, output means, and data storage means. A skilled artisan can readily appreciate that any one of the currently available computer-based systems are suitable for use in the present invention. The data storage means may comprise any manufacture comprising a recording of the present information as described above, or a memory access means that can access such a manufacture.

A variety of structural formats for the input and output means can be used to input and output the information in the computer-based systems of the present invention. One format for an output means ranks cell characteristic profiles possessing varying degrees of similarity to a reference profile. Such presentation provides a skilled artisan with a ranking of similarities and identifies the degree of similarity contained in the test profile.

A subject database is useful for comparing a test profile to a reference profile that is stored in the database. Thus, the invention provides methods of identifying or determining a characteristic of a cell, involving comparing a test profile of a cell with a database of profiles. For example, a cell profile that is generated in a clinical setting by analyzing a lung or other tissue biopsy sample (the "test profile") is compared to one or more reference profiles stored in the database, where the reference profiles contain characteristics of normal (non-cancerous) lung cells, various types of cancerous lung cells, etc. Based on the comparison to the database, a determination of a characteristic of the test profile is made.

The invention further provides methods of obtaining a cell characteristic profile, and methods of generating a database, or collection, of cell characteristic profiles. The methods generally involve detecting membrane movement of a cell, storing the membrane movement data on a computer readable medium (CRM), and linking the data with at least one additional data about the cell (e.g., cell type, biological state, biological event which resulted in the membrane movement, cell medium conditions, and the like), thereby generating a profile. The cell profile is recorded on a CRM. A database includes a plurality of such profiles. In some embodiments, the cell profile is represented in a visual format. In other embodiments, the cell profile is represented in a sound format. In other embodiments, the cell profile is represented in a graphical format.

Where the data are generated using a micromirror-based analytical system as described above, the data are generated and stored in the form of the degree of deflection of a reflected beam of light compared to a control. The data are obtained by measuring the cell membrane movement of a wide variety of cell types. The membrane movement of each cell type is recorded under various conditions. As one non-limiting example, cell membrane movement of a myocyte or other cell lineage is measured in media of various pH, in media containing various agents (e.g., adrenaline, a calcium ionophore), in media containing various ion concentrations, in media containing agents that induce a conditions that mimics a disease state, under normal physiological conditions, and the like. The cell characteristic is recorded for each condition, and information regarding the condition is entered into the database, such that the two pieces of information are linked. The information in the database is searchable using terms for the cell type, and cell conditions. In another non-limiting example, cell membrane movement of a CD4$^+$T lymphocyte is recorded under normal physiological conditions (e.g., in serum), the cell membrane movement of a CD4$^+$T lymphocyte that is infected with human immunodeficiency virus is recorded, and the cell membrane movement of various T cell leukemias are recorded and stored in the database.

Figure 17:
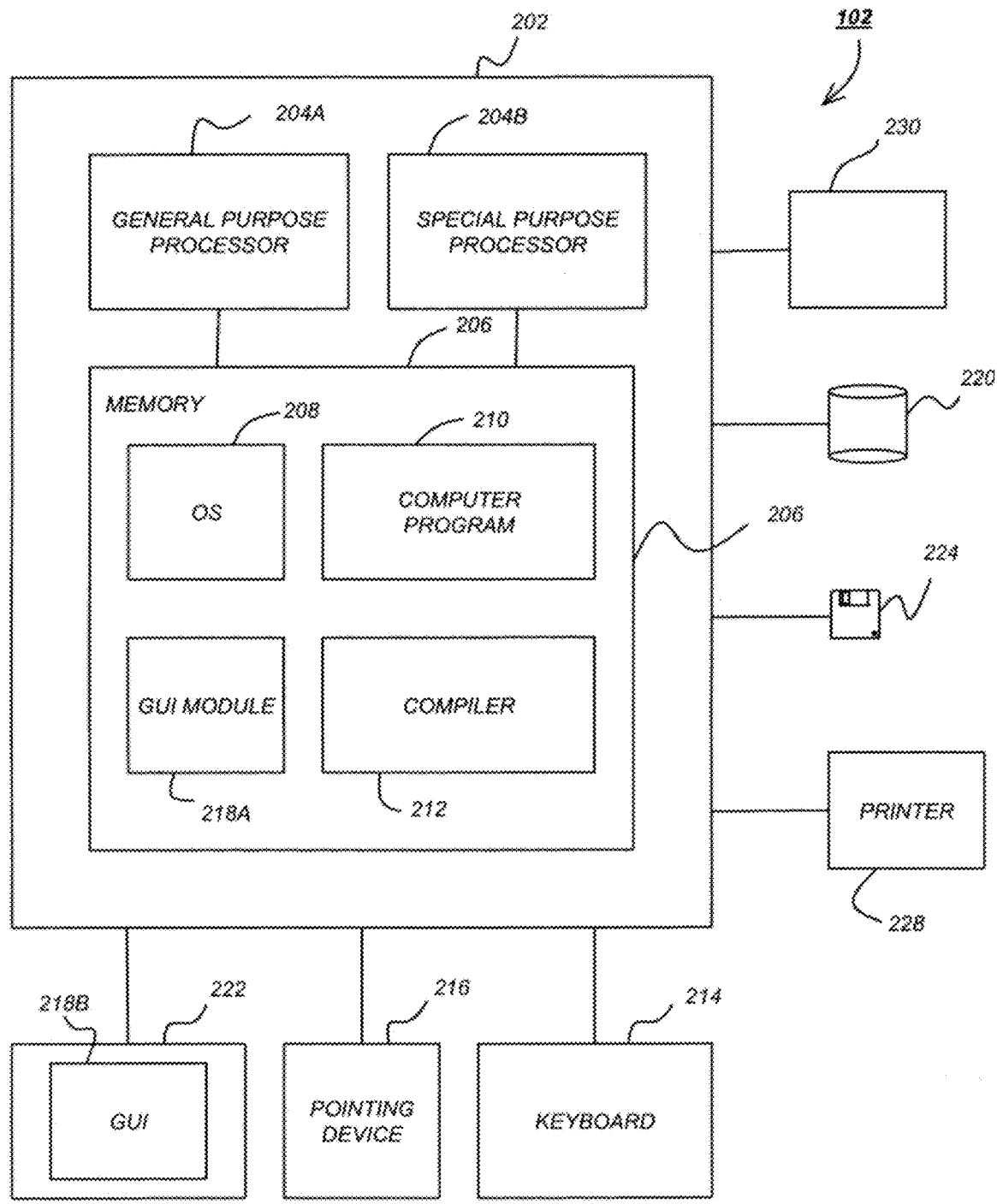
FIG. 17 shows one embodiment of a illustrative computer system that can be used with embodiments of the invention.

Embodiments of the invention disclosed herein can be performed for example, using one of the many computer systems known in the art. For example, embodiments of the invention include a database comprising a plurality of cell characteristic profiles recorded on a computer readable medium, each of said cell characteristic profiles comprising cell membrane movement data and at least one additional cell parameter. Additional cell parameters include, e.g., a cell type, a biological state, a cell environment, and a stimulus. FIG. 17 illustrates an exemplary generalized computer system 202 that can be used to implement elements the present invention, including the user computer 102, servers 112, 122, and 142 and the databases 114, 124, and 144. The computer 202 typically comprises a general purpose hardware processor 204A and/or a special purpose hardware processor 204B (hereinafter alternatively collectively referred to as processor 204) and a memory 206, such as random access memory (RAM). The computer 202 may be coupled to other devices, including input/output (I/O) devices such as a keyboard 214, a mouse device 216 and a printer 228.

In one embodiment, the computer 202 operates by the general purpose processor 204A performing instructions defined by the computer program 210 under control of an operating system 208. The computer program 210 and/or the operating system 208 may be stored in the memory 206 and may interface with the user 132 and/or other devices to accept input and commands and, based on such input and commands and the instructions defined by the computer program 210 and operating system 208 to provide output and results. Output/results may be presented on the display 222 or provided to another device for presentation or further processing or action. In one embodiment, the display 222 comprises a liquid crystal display (LCD) having a plurality of separately addressable liquid crystals. Each liquid crystal of the display 222 changes to an opaque or translucent state to form a part of the image on the display in response to the data or information generated by the processor 204 from the application of the instructions of the computer program 210 and/or operating system 208 to the input and commands. The image may be provided through a graphical user interface (GUI) module 218A. Although the GUI module 218A is depicted as a separate module, the instructions performing the GUI functions can be resident or distributed in the operating system 208, the computer program 210, or implemented with special purpose memory and processors.

Some or all of the operations performed by the computer 202 according to the computer program 110 instructions may be implemented in a special purpose processor 204B. In this embodiment, the some or all of the computer program 210 instructions may be implemented via firmware instructions stored in a read only memory (ROM), a programmable read only memory (PROM) or flash memory in within the special purpose processor 204B or in memory 206. The special purpose processor 204B may also be hardwired through circuit design to perform some or all of the operations to implement the present invention. Further, the special purpose processor 204B may be a hybrid processor, which includes dedicated circuitry for performing a subset of functions, and other circuits for performing more general functions such as responding to computer program instructions. In one embodiment, the special purpose processor is an application specific integrated circuit (ASIC).

The computer 202 may also implement a compiler 212 which allows an application program 210 written in a programming language such as COBOL, C++, FORTRAN, or other language to be translated into processor 204 readable code. After completion, the application or computer program 210 accesses and manipulates data accepted from I/O devices and stored in the memory 206 of the computer 202 using the relationships and logic that was generated using the compiler 212. The computer 202 also optionally comprises an external communication device such as a modem, satellite link, Ethernet card, or other device for accepting input from and providing output to other computers.

In one embodiment, instructions implementing the operating system 208, the computer program 210, and the compiler 212 are tangibly embodied in a computer-readable medium, e.g., data storage device 220, which could include one or more fixed or removable data storage devices, such as a zip drive, floppy disc drive 224, hard drive, CD-ROM drive, tape drive, etc. Further, the operating system 208 and the computer program 210 are comprised of computer program instructions which, when accessed, read and executed by the computer 202, causes the computer 202 to perform the steps necessary to implement and/or use the present invention or to load the program of instructions into a memory, thus creating a special purpose data structure causing the computer to operate as a specially programmed computer executing the method steps described herein. Computer program 210 and/or operating instructions may also be tangibly embodied in memory 206 and/or data communications devices 230, thereby making a computer program product or article of manufacture according to the invention. As such, the terms "article of manufacture," "program storage device" and "computer program product" as used herein are intended to encompass a computer program accessible from any computer readable device or media.

Of course, those skilled in the art will recognize that any combination of the above components, or any number of different components, peripherals, and other devices, may be used with the computer 202. Although the term "user computer" is referred to herein, it is understood that a user computer 102 may include portable devices such as medication infusion pumps, analyte sensing apparatuses, cellphones, notebook computers, pocket computers, or any other device with suitable processing, communication, and input/output capability.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Aspects of the invention disclosed herein can be found in Reed et al., ACS NANO, 2(5): 841-846 (2008) and Reed et al., Nanotechnology 19: 235101 (2008), the contents of which are incorporated by reference.

Example 1: High-Throughput Cell Nano-Mechanics with Mechanical Imaging Interferometry This example provides an illustrative, high-throughput approach to measuring the nano-mechanical properties of a large number of cells in parallel, based on imaging interferometry in combination with reflective, magnetic probes attached to cells. In this example, we measure local elastic properties with applied forces of 20 pN to 20 nN, a spatial resolution of <20 nm, and a mechanical dynamic range of several Pa up to ~200 kPa. This disclosure provides evidence that mechanical imaging interferometry (MII) is a sensitive and scalable technology for measuring the nano-mechanical properties of large arrays live cells in fluid. Illustrative data for NIH 3T3 and HEK 293T fibroblasts as well as the effects of actin depolymerizing drugs are disclosed.

This example demonstrates a nanomechanical probing method, called mechanical imaging interferometry (MII), based on combining vertical scanning interferometry with reflective, magnetic probes attached to cells, that permits axially-oriented mechanical measurements of live cells with picoNewton force resolution over wide fields of view. Mechanical imaging interferometry (MII) has axial position repeatability of <20 nm over a very wide vertical range (millimeters), and can measure materials with elastic moduli over the range of 50 Pa to 100+ kPa. Because the interferometric technique used is relatively insensitive to magnification, we retain excellent positional resolution at fields of view of up to or exceeding 740×570 microns, permitting simultaneous measurement of hundreds of probes. This allows throughput equal to or exceeding existing wide-field optical tracking techniques by several times. Unlike these aforementioned methods, MII directly measures the position of the bead on the cell membrane versus the substrate, and thus determine cell thickness very accurately, which is critical to accurate mechanical modeling of cells in some cases (see, e.g. Dimitriadis et al., (2002) Biophysical Journal 82, 2798-2810). Using soft polyacrylamide gels of known stiffness, we demonstrate an absolute measurement accuracy equal to that of AFM indentation in a similar experimental configuration (6% standard error on a gel with Young's modulus of 4 kPa, n=23)). Using MII we determine the quasi-static mechanical properties of populations of NIH 3T3 and HEK 293T fibroblasts, by probing large arrays of individual cells in parallel. The absolute values of the mechanical constants determined by MII are in excellent agreement with results from a variety of other probing methods.

The results show that MII is an effective, high throughput technique for measuring cellular mechanical properties through indentation normal to the cell surface. This represents a significant throughput advance over AFM, and other optical approaches, such as confocal microscopy or microfluidic optical stretchers (see, e.g. Guck et al., (2005) Biophysical Journal 88, 3689-3698), which cannot accurately measure mechanical properties of large arrays (hundreds) of cells simultaneously, with single-cell specificity (see, e.g. Cheezum, M. K., Walker, W. F. & Guilford, W. H. (2001) Biophysical Journal 81, 2378-2388, Carter et al., (2005) Physical Biology 2, 60-72). The mechanical dynamic range and effective magnification of MII equals or exceeds existing wide-field optical particle tracking techniques (see, e.g. Fabry et al., (2001) Journal of Applied Physiology 91, 986-994), which implies that the two could be used in combination to conduct rapid, fully-3D mechanical probing of large arrays of live cells.

Materials and Methods

Interferometer

The measurement of the microreflectors was performed on the Veeco interference microscope NT 1100 with a green diode (center frequency 535 m) used for illumination and 20× 0.28NA Michelson through transmissive media (TTM) objective (see, e.g. Reed et al., (2006) PROCEEDINGS-SPIE THE INTERNATIONAL SOCIETY FOR OPTICAL ENGINEERING 0277-786X; 2006; VOL 6293, p. 629301). The NT 1100 in principle is an optical microscope with a Michelson interference objective that allows for the observation of not only lateral features with typical optical resolution (1.16 μm for the 20× objective) but also height dimensions below the scale of one nanometer (see, e.g. Olszak et al., (2001) Laser Focus World 37, 93-95). The Michelson interferometer is composed of a beam splitter, reference mirror and compensating fluid cell. The compensation cell is 0.7 mm thick bounded on both sides by 0.5 mm optical windows, thus matching the optical path length of a reflected beam from the test chamber (i.e. matching the optical path difference between the arms). The CCD detector array is 640×480 pixels, which with a 20× objective produces a 315×240 micron field of view and a spatial sampling of 500 nm. Measured positions of the reflectors with respect to the bottom of the sample chamber were corrected for the effect of dispersion in liquid, using a group velocity at 535 nm wavelength and 30 nm bandpass of Ng=1.33 (see, e.g. Millard et al., (1990) Deep-Sea Research Part a-Oceanographic Research Papers 37, 1909-1926).

Cell Chamber

The cell chamber body was constructed from machined non-magnetic stainless steel. Resistive heating elements with internal thermistors, driven by a feedback controlled power supply, were used to regulate the chamber temperature to within 0.5 degrees C. The fluid sample was contained within a 13 mm diameter, 0.7 mm thick sub chamber, having a 1 mm thick optical window on top and a 0.2 mm thick silicon floor. Fluid within the chamber could be exchanged through two peripheral infusion ports, using a micro peristaltic pump capable of flow rates as low as 5 μL min.

Microreflectors

Elemental nickel microspheres were obtained from Duke Scientific as a dry powder with size distribution 2-10 μm in diameter. For each experiment approximately 0.1 mg of powder was mixed with 1 mL of distilled water. Smaller diameter particles were removed by sedimentation, resulting in a dilute suspension with size distribution ~5-10 μm. This suspension was diluted 4:1 with 0.2% poly-L-lysine aqueous solution (SIGMA) to inhibit aggregation and improve adhesion to the cell bodies. The microreflector solution was shaken vigorously before application to suspend any sedimented particles and reduce aggregates. 200 μL of the suspension was pipetted onto the sample (gel or cells) and the microreflectors allowed to settle for minute.

Magnetic Force Control

Magnetic force was applied to the microreflectors using a cylindrical rare earth magnet 7 mm in diameter by 21 mm long, oriented axially along the vertical direction below the test chamber. The magnet was positioned with a feedback controlled motorized micrometer, capable of <10 μm accuracy. The magnitude of magnetic flux perpendicular to the vertical axis, as a function of axial distance, was measured with a miniature Hall probe. In the "off" position, the magnet was lowered to >4 cm below the sample, resulting in negligible field at the sample point. The magnet was positioned coaxially with the optical path to ensure a uniform magnetic flux across the viewing area (~300 μm×300 μm with the 20× objective). The force applied to the nickel microreflectors as a function of magnet position was determined using microcantilever arrays tipped with elemental nickel or several uniformly magnetic microspheres (Compel 8 um carboxylated microspheres, BANGS LABS). Each microcantilever is 500 microns long by 100 microns wide and 0.9 microns thick, with a nominal spring constant of 0.01 N/m. These commercially available arrays were produced by the IBM ZURICH RESEARCH LABORATORIES using a proprietary dry etch, silicon-on-insulator (SOI) process. Using the optical profiler, the deflection of the reference cantilever could be determined to better that 1 nm. The volume magnetic moment for pure nickel (55 emu/g) was assumed for both the microreflectors and the nickel film deposited on the cantilever tips. Pure nickel is completely magnetically polarized at field strengths of 200 G and higher, while the lowest field strength used in measurements was 500 G. Preceding measurements, the magnet was raised to with 1.5 mm of the sample, corresponding to a ~2 kG flux at the sample point, to ensure that the microreflectors' magnetic moments were oriented axially.

Polyacrylamide Gel Tests

5% acylamide/0.15% bis-acrylamide and 5% acrylamide/0.05% bis-acrylamide gels were cast between a microscope slide and cover slip, using 40 μm tape as a spacer, using standard conditions (see, e.g. Engler et al., (2004) Surface Science 570, 142-154). A 5×5 mm section of each gel was removed with a scalpel and placed inside the fluid test chamber for measurement. Sample in the test chamber were allowed to equilibrate overnight in 1× TBE buffer, pH 7.5, the same buffer used to prepare the gels. All measurements were conducted under buffer.

Cell Viscoelastic Measurements

The population measurements of the NIH 3T3 fibroblasts and the HEK 293T fibroblasts were conducted over several consecutive days. Both cell types were cultured at the same time on a series of poly-L-lysine coated 0.20×10 mm round glass coverslips, in 1×DMEM with 10% fetal bovine serum in a laboratory incubator under standard cell culture conditions. Preceding measurement, a single round coverslip containing cells would be removed from the culture dish and quickly placed in the microscope test chamber. Microreflectors would be added to media from the original culture dish, which would then be pipetted slowly onto the cells and the sample chamber sealed. Cells were allowed to equilibrate in the test chamber for 30 minutes before measurement. The average radius of the measured microreflectors was 3.79 µm, and the average applied force was 190 pN. The average cell height was 8.1 µm and the average maximum indentation depth per cell was 660 nm. The following factors showed no significant difference between the two populations on the basis of ANOVA analysis: Cell height, applied force, reflector radius and maximum indentation depth/radius.

The three constants for a viscoelastic solid were determined for each measurement by fitting the time-dependent force-displacement curves of the microreflectors to the following equation (see, e.g. Cheng et al., (2005) Mechanics of Materials 37, 213-226):

$$\delta(t) = \frac{3}{4}\sqrt[3]{3F^2/4RE_1^2}\left\{\left(-\frac{E_1}{E_2}e^{-(E_2 t/3\eta)}\right) + \left(\frac{E_1 + E_2}{E_2}\right)\right\}^{2/3}$$

Our measurements assumed Poisson's ratio for the cell, $v=0.5$. Curves were fitted using the Levenberg-Marquardt non-linear least squares procedure (Origin Labs). The z-statistic was used to compare the log-transformed sample means and determine p values. The Bartlett test was used to confirm homogeneity of the compared sample variances.

To remain within the semi-infinite layer assumptions of this model, we present fits only for observations where the minimum cell thickness at the location of the microreflector was 3 µm or greater. A majority of the measurements fit the model elastic constants $E_1$ and $E_2$ well, having a relative standard error of fit <25%. There was larger uncertainty in the viscosity factor, $\eta$, with only 30% of the fits having a relative standard error <25%. The error in $\eta$ is mainly due to the temporal sampling rate of 0.1 Hz, which did not adequately resolve the rapid indentation of the microreflectors on the softest cells.

Cytochalasin B Measurements

Cells were prepared for measurement as described above. A continuous infusion of fresh media into the sample chamber, warmed to 37 C and pre-saturated with 5%$CO_2$, was maintained at all times. The rate of infusion was 5 µL/min, equivalent to exchanging the entire volume of the test chamber in 20 minutes. Cells were equilibrated under flow for 45 minutes before measurement. Flow was halted during each measurement cycle, which lasted approximately 200 seconds. The first, a media-only measurement was conducted at 1 hour, immediately followed by introduction of cytochalasin B into the infusing media. Initially, the cytochalasin B was dissolved in DMSO and diluted in DMEM to produce a stock concentration 1000× the working concentration (1 µM or 10 µM). At the appropriate time, the stock solution was introduced into the infusion media reservoir to produce the desired final concentration.

Mechanical Dynamic Range and Throughput

The range of force achievable on an 8 micron diameter nickel microreflector was approximately 20 pN up to 20 nN. We could obtain axial measurement precision of the microreflector versus the sample substrate of <20 nm, which is sufficient to compute the elastic modulus of soft materials with less than 5% error, using the linear Hertz model for a spherical indenter (see, e.g. Lim et al., (2006) Journal of Biomechanics 39, 195-216). For the purpose of this analysis, it was assumed that the bead diameter and magnetic force can be determined to arbitrary precision.

In both MII and standard wide field bead tracking experiments, for a given bead diameter and measurement time, throughput is limited by the number of probes in the field of view. We were able to obtain measurement precision of <20 nm using a 20× 0.28NA objective and a 0.5× demagnifier, with a CCD detector array having 640×480 pixels, which produced a 600×440 micron field of view and a spatial sampling of 952 nm. In comparison, wide-field optical magnetic twisting cytometry (OMTC) uses a 10×0.2NA objective and a camera with 780×600 pixels, which produces a 450×350 micron field of view and a spatial sampling of 570 nm per pixel. Therefore, if we used a CCD with 780×600 pixels and the same 952 nm spatial sampling, we would obtain a field of view of 742×571 microns, which equates to roughly 3× the measurement area vs. OMTC.

Results and Discussion

Mechanical imaging interferometry (MII) makes use of spherical microreflectors fixed to the cell membrane, that act as nanoscopic displacement probes. We developed a special liquid force cell for these measurements using a Michelson interferometer (FIG. 1A). Measuring live cells in culture required the placement of a liquid-filled compensation cell in the reference arm of the interferometer. Dimensions of the compensation cell were adjusted to exactly match the optical path length between the test and reference arms. Cells are evaluated in a sealed environmental chamber maintained at 5% $CO_2$, 37° C., with infusion ports for exchanging media and the introduction of drugs and other chemicals. The microreflectors were pure nickel, ranging from 6 to 10 microns in diameter.

During each measurement, the objective head is scanned vertically from the surface to a height 40 microns above the surface, such that each point in the volume passes through focus. The interferometer is aligned so that the interference intensity distribution along the vertical scanning direction has its peak (best fringe contrast) at approximately the best focus position. The vertical-axis position of each microreflector is determined as the location of the coherence peak within the scan. By measuring microreflectors of known height fixed to a solid substrate in liquid, we determined that the z-axis measurement repeatability was <20 nm. Magnetic forces applied to the nickel microspheres were calibrated with a ferromagnetic-tipped microcantilever array, having a known spring constant (k=0.01 N/m) and magnetic moment. The range of force achievable on an 8 micron diameter nickel microreflector was approximately 20 pN up to 20 nN. A critical consideration for cell nanomechanical measurements is the dynamic range of the measurement technique. Mammalian cells exhibit a wide range of Young's moduli, from as soft as 10 Pa to as stiff as 100 kPa (see, e.g. Balland et al., (2006) Physical Review E 74). We estimate that MII can effectively measure samples with elastic moduli that vary from several Pa up ~200 kPa, as currently configured.

To validate our approach, we first tested the microreflectors on 40 micron thick, soft polyacrylamide (PA) gels under liquid, which simulated the cell body (FIGS. 2A-2D). We recorded the vertical displacement of the microspheres in response to a series of increasing forces. The resulting force-displacement curves fit the Hertz contact model (see, e.g. (Lim et al., (2006) Journal of Biomechanics 39, 195-

216) for a spherical indenter well. For the 40 micron-thick polyacrylamide gels, the measured values for Young's modulus were linearly proportional to the crosslinker concentration, as expected, and the range of absolute values and measurement precision (1,530 S.E.+/−128 Pa (n=22) and 4,020 S.E.+/−270 Pa (n=23)) agree well with similar measurements by others using AFM and bulk techniques (see, e.g. Mahaffy et al., (2004) Biophysical Journal 86, 1777-1793; Mahaffy et al., (2000) Physical Review Letters 85, 880-883; Engler et al., (2004) Biophysical Journal 86, 617-6).

Figure 3A:
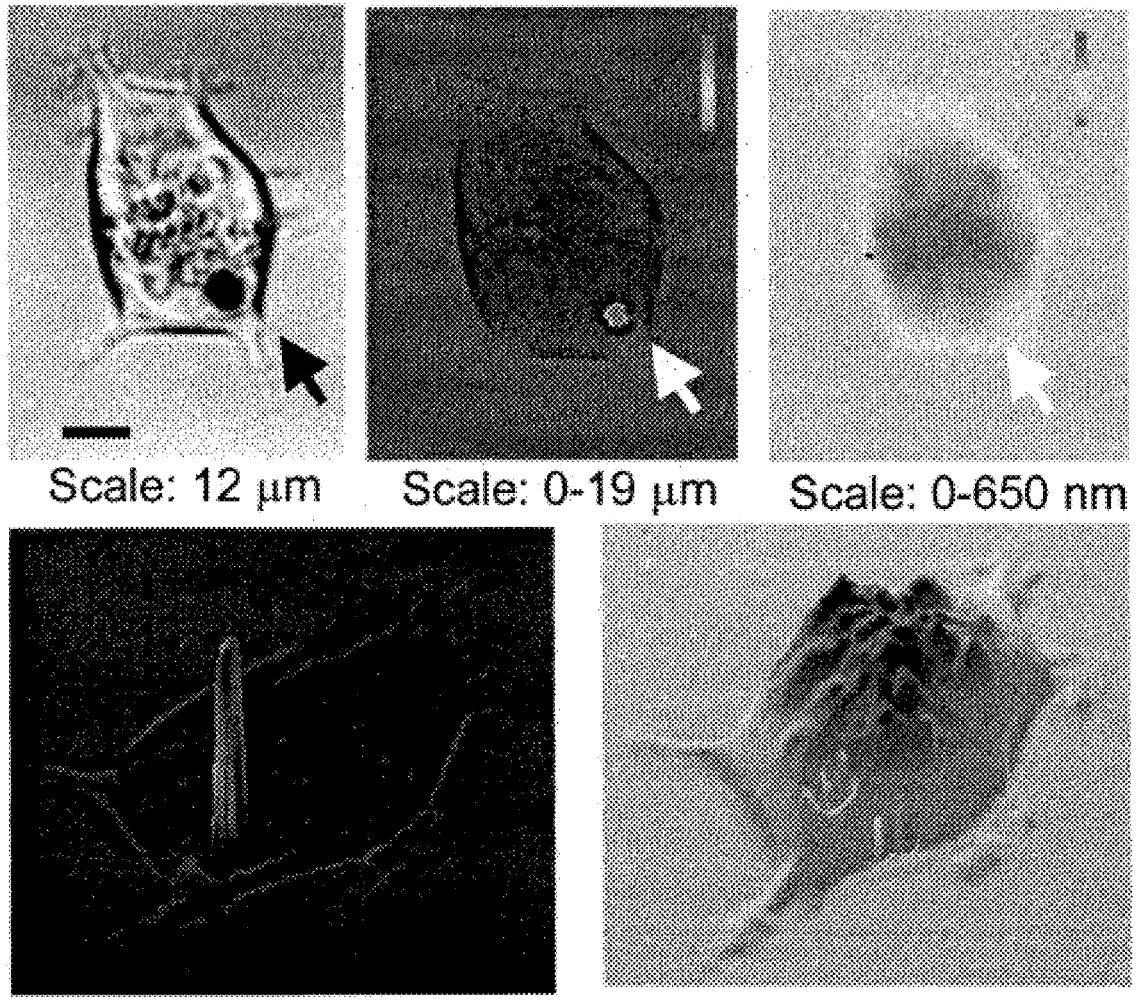
FIG. 3A shows the intensity image of an NIH 3T3 fibroblast (Top left) with a microreflector positioned on the cell membrane (arrow). The corresponding vertical scanning interferometry (VSI) height profile (middle) includes only the microreflector since the cell body is minimally reflective and can be seen and/or calculated out in embodiments of the invention. The phase-shifting (PSI) interferometric image (right), shows the cell body, where apparent height corresponds to increased optical path length due to the higher index of refraction of the cytoplasm versus the surrounding media. The use of PSI measurements with this apparatus is detailed in (see, e.g. Reed et al., (2006) Proc. SPIE Int. Soc. Optical Eng., 6293: 629301). The microreflector is opaque and does not appear in the PSI image because it is not the focus in the optical field being examined. Below: The VSI and PSI height profiles are rendered in 3D for clarity.
Figure 3B:
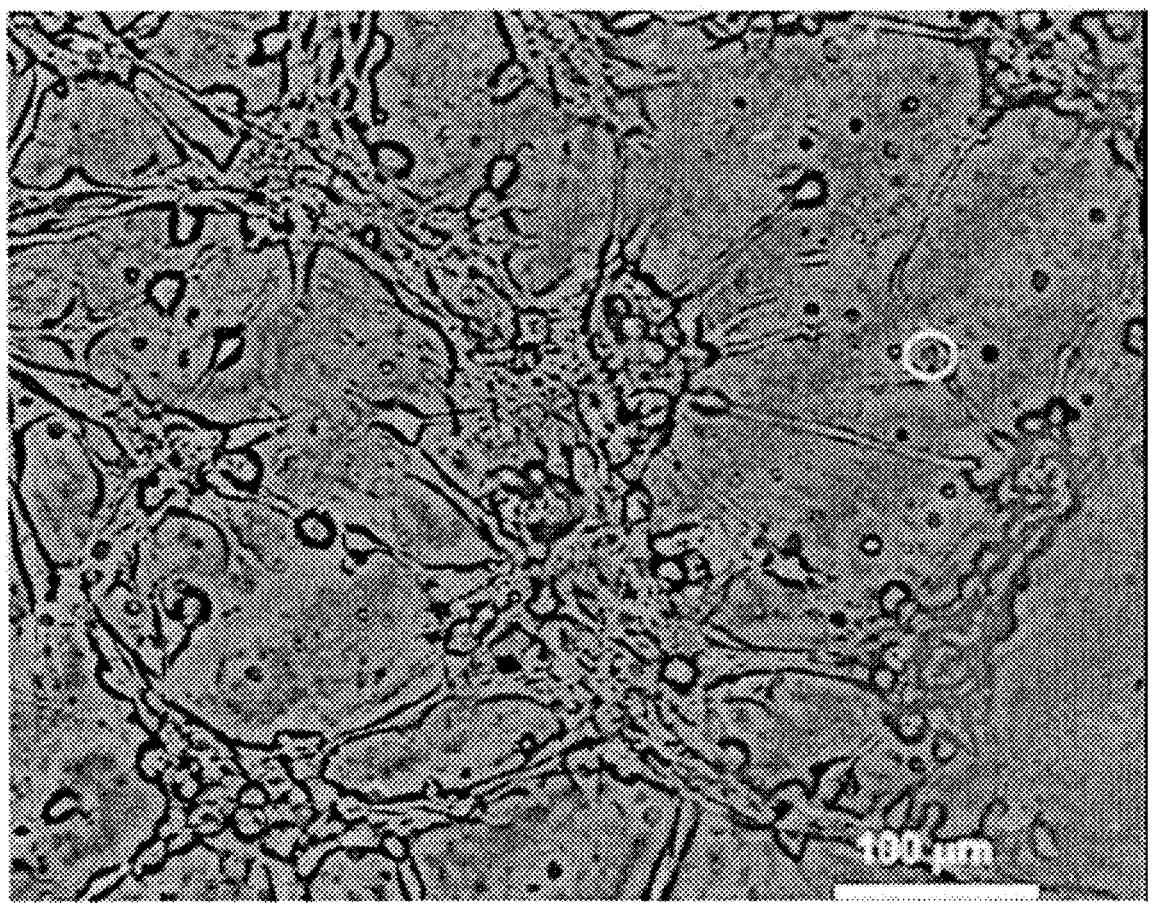
FIG. 3B shows an intensity image of NIH 3T3 fibroblasts coated with nickel micromirror beads in the cell chamber, taken at 10× magnification. The field of view is 600×460 μm. The VSI interferometric image is overlaid in blue, showing the detection of 103 microreflectors (example indicated with white circle).
Figure 4:
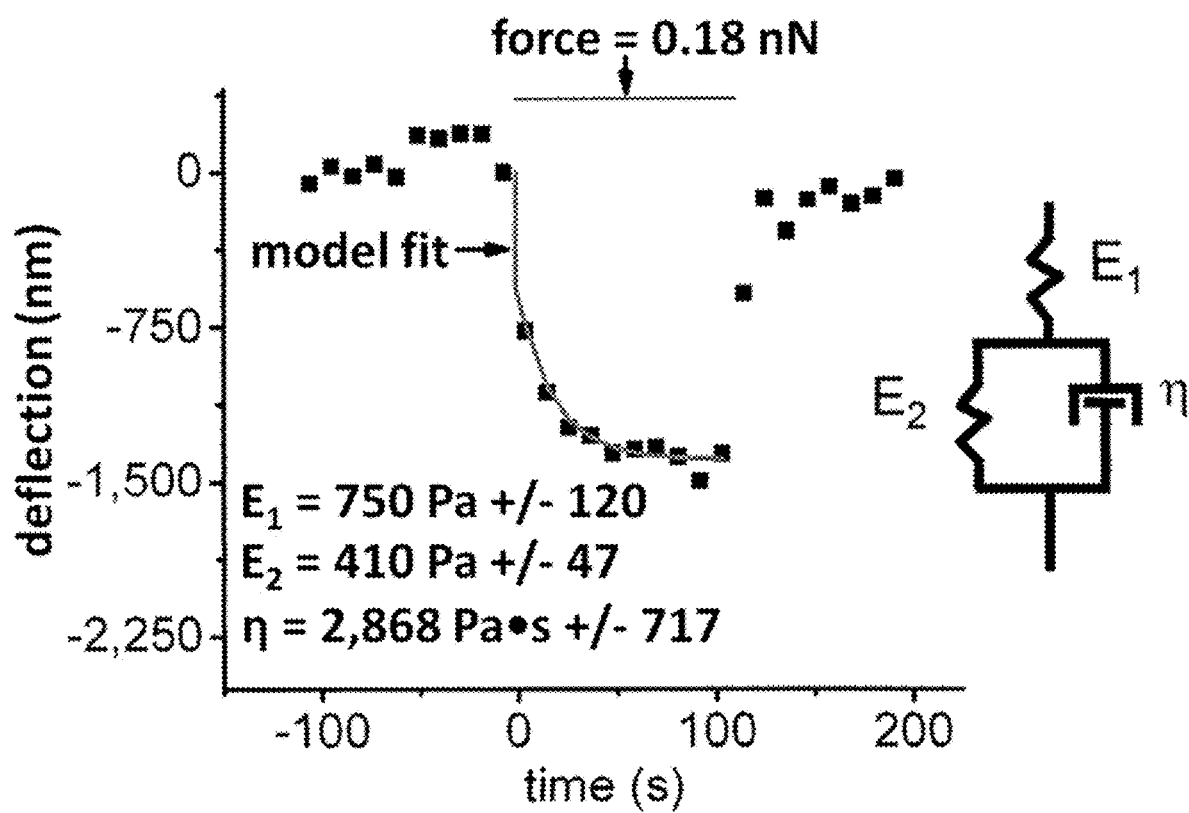
FIG. 4 shows a force-distance curve showing the deflection of a 10 μm nickel microreflector into a single HEK293T cell. The viscoelastic nature of the cell body is apparent from the delay between the onset of force change and the time required to reach an equilibrium deflection (creep). This creep phenomenon is not captured by the time-invariant Hertz contact model. A simple three-factor viscoelastic solid model, represented by the mechanical spring and dashpot model (inset), describes the observed behavior more completely. This model contains an instantaneous elastic constant, $E_1$, and a time-delayed elastic constant, $E_2$. The time delay is governed by the magnitude of $E_2$ and the viscosity, η. The three viscoelastic constants can be calculated by fitting the observed force-deflection curve to a version of the three-factor model applicable to spherical indenter geometry (see, e.g. Cheng et al., (2005) Mechanics of Materials 37, 213-226). Curves are fitted using the Levenberg-Marquardt non-linear least squares procedure.

Next, we measured the mechanical properties of live mouse NIH3T3 and human HEK293T fibroblasts. In the perfusion chamber, the microreflectors on top of individual cells or cell layers appeared as distinct objects in the interferometer image (FIGS. 3A and 3B). Similar to the PA gel tests, we applied a series of step forces and recorded vertical reflector displacements. The indentation and recoil was proportional to the applied force, as expected, but the cell bodies showed a distinct viscoelastic response, versus the purely elastic behavior of the PA gels. This is most clearly seen as 'creep behavior' of the microreflectors in response to a step change in force (FIG. 4).

Figure 5:
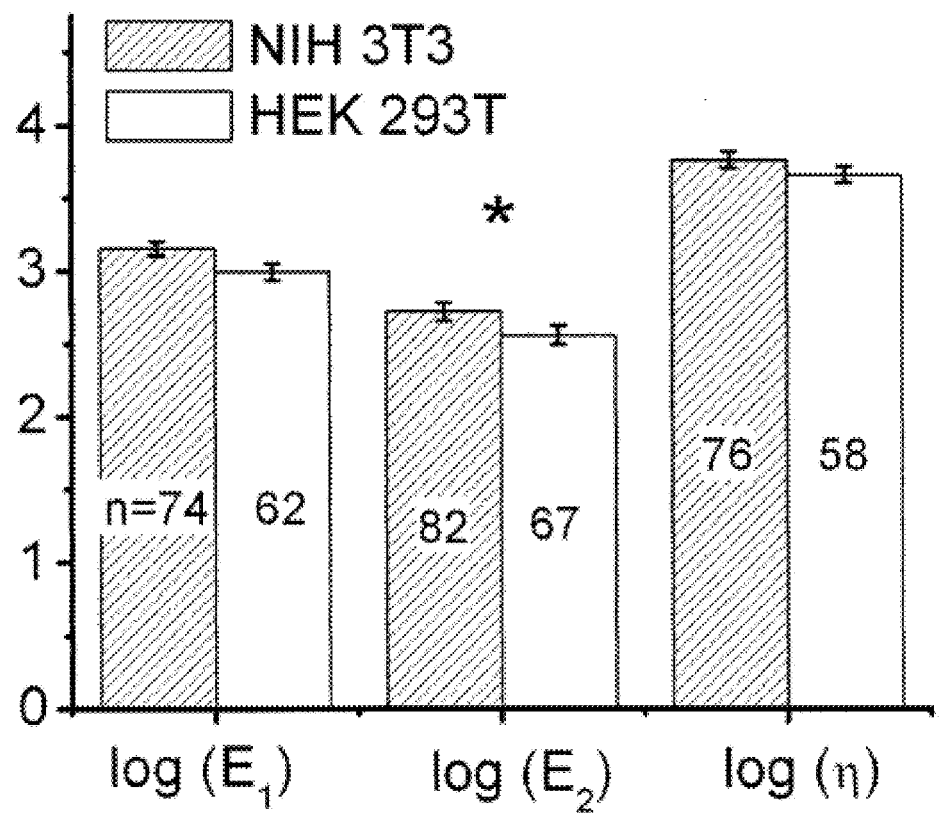
FIG. 5 shows the population distribution of the three viscoelastic constants determined for populations of NIH 3T3 and HEK 293T fibroblasts. The error bars indicate standard error of the mean, and * indicates statistical significance at the >95% level. The mean of the log-transformed distribution of $E_1$ was 3.45 for NIH3T3 and 3.33 for HEK293T fibroblasts (p=0.10). The means of the log-transformed distributions of $E_2$ were 3.06 and 2.90 (p=0.03), and the means of the log-transformed viscous constants η were 4.11 and 4.00 (p=0.17), respectively.

Live cells are known to exhibit complex frequency-dependent viscoelastic properties (see, e.g. Trepat et al., (2007) Nature 447, 592-U7; Lenormand et al., (2004) Journal of the Royal Society Interface 1, 91-97; Desprat et al., (2005) Biophysical Journal 88, 2224-223328). For the purpose of this study were primarily interested in determining the equilibrium elastic modulus of the cells. To this end, we used a 3-factor linear viscoelastic solid model to parameterize the cell's response (see, e.g. Cheng et al., (2005) Mechanics of Materials 37, 213-226). This type of model has been used to characterize the viscoelastic properties of cells and soft polymers (see, e.g. Lim et al., (2006) Journal of Biomechanics 39, 195-216). It consists of two springs and a dashpot, specified by two elastic constants (E1, E2) and one viscous constant ($\eta$). The stress-bearing capacity of the cytoskeleton is represented by a short term-response, E1, and a slower response, E2. The response of the spring element $E_2$ is delayed by viscous drag. Our ability to resolve the viscous constant is limited by the 0.1 Hz temporal sampling rate, but this does not impact our ability to measure the equilibrium elasticity, which is given by $E_1$ and $E_2$. A full temporal characterization of the cellular viscoelastic response is beyond the scope of this study, however, as we discuss below, MII is fully compatible with the cyclic probing methods commonly used to determine frequency-dependent mechanical moduli. For both cell types, the population distributions of the viscoelastic constants were log-normally distributed, with geometric standard deviations of ~1.5 logs. This result is in agreement with recent reports (see, e.g. Fabry et al., (2001) Journal of Applied Physiology 91, 986-994; Balland et al., (2006) Physical Review E 74; Maksym et al., (1999) American Journal of Respiratory and Critical Care Medicine 159, A470-A470). The means and standard errors of the log-transformed pooled measurements for both cell types are shown in FIG. 5. The mechanical constants for the HEK293T cells are consistently lower than for the NIH3T3 cells, although the difference was statistically significant at the >95% level only for the delayed elastic constant E2.

Figure 6A:
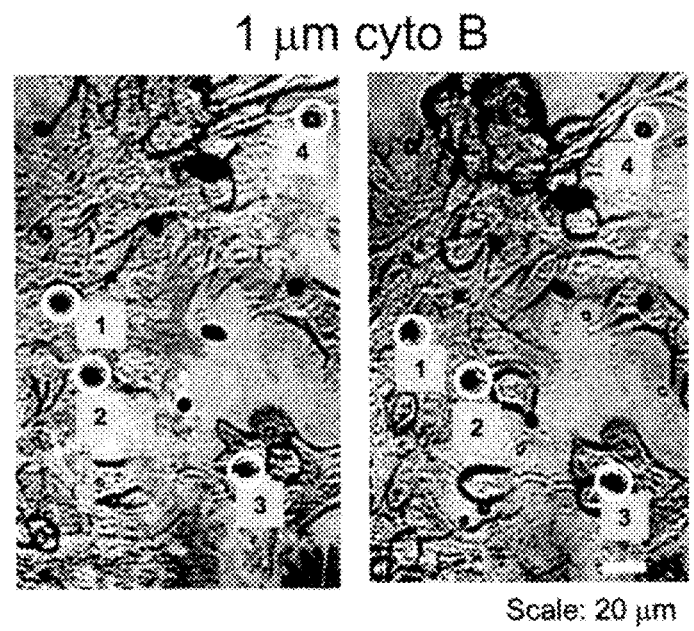
FIG. 6A shows the intensity image (left) of NIH3T3 cells with microreflectors in place, before and after treatment with 1 μm cytochalasin B.
Figure 6B:
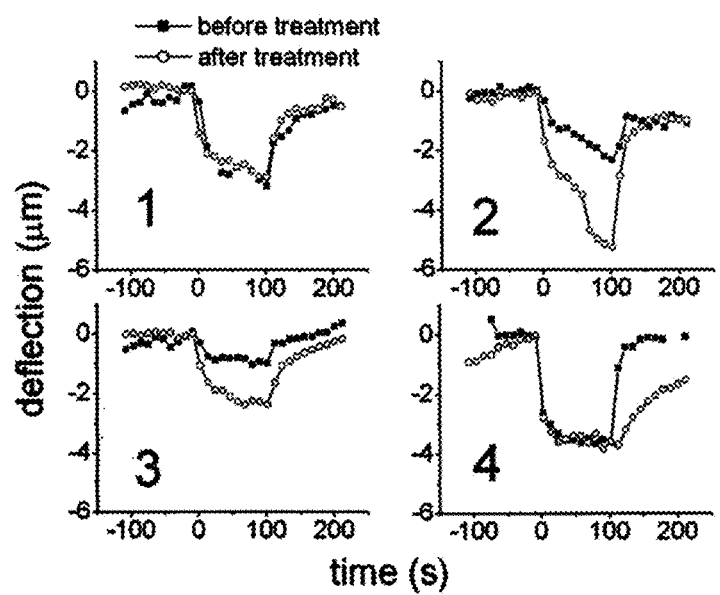
FIG. 6B shows the force-displacement curves of four individual microreflectors before and after treatment shows the change in viscoelastic behavior in response to normal force applied for 100 seconds (t=0-100 on the graphs). Probes 2 and 3 show a clear decrease in stiffness, while probe 4 shows a change in elastic rebound behavior, and probe 1 appears to be unchanged. The force generated on the cell by each microreflector is a function of the probe's total mass: (1) radius+3.85 µm, force=180 pN; (2) radius=3.90 µm, force=190 pN; (3) radius=3.40 µm, force=130 pN; (4) radius=4.75 µm, force=340 pN.

We evaluated the behavior of NIH3T3 cells (n=30) exposed to a low dose (1 µM) of cytochalasin B, which inhibits actin polymerization. At low doses (0.1-1 µM), cytochalasin B does not produce large changes in the morphology of fibroblasts, although it does inhibit cell migration (see, e.g. Rotsch et al., (2000) Biophysical Journal 78, 520-535; Yahara et al., (1982) Journal of Cell Biology 92, 69-78), and AFM indentation studies have reported minimal, if any, measurable change in Young's modulus (see, e.g. Rotsch et al., (2000) Biophysical Journal 78, 520-535). In contrast, we determined that treated cells were less elastic. For the population, the mean of the log-transformed distribution of E1 was 3.19 before treatment and 2.92 after (p=0.10). Similarly, the means of E2 were 2.30 before and 2.02 after (p=0.04), and the means of the viscous constants $\eta$ were 3.39 before and 3.36 after (p=0.47) (FIG. 6A). While the population difference was statistically significant only for E2, on a matched, individual cell basis, the elasticity was consistently lower after treatment (E1 10/13 lower, E2 7/10 lower), while viscosity was not ($\eta$ 6/11 lower). Qualitatively, 1 µM cytochalasin produced only a slight change in cell morphology up to 45 minutes, as expected, while the indentation profiles show a clear change in some cells and not in others (cells 2 and 3 in FIG. 6B).

Measurements of live fibroblast cells provide a direct comparison of MII to AFM and other nano-indentation methods. The magnitude of the elastic constants and the response to cytochalasin B determined by MII were in excellent agreement with reported results for fibroblasts, determined by AFM, bead-tracking microrheology and microplate traction (see, e.g. Lim et al., (2006) Journal of Biomechanics 39, 195-216). The temporal sampling rate in our experiments was 0.1 Hz, effectively limiting our mechanical measurements to quasi-static. Therefore, while the average viscous constant we determined for both fibroblast cell types is similar to that reported by other methods (see, e.g. Lim et al., (2006) Journal of Biomechanics 39, 195-216; Koay, E. J., Shieh, A. C. & Athanasiou, K. A. (2003) Journal of Biomechanical Engineering-Transactions of the Asme 125, 334-341), we cannot effectively determine $\eta$ for cells with a very low viscosity (<~1 kPa s). This resulted in the relatively larger error in fitting the viscous constant versus the elastic constants in our three factor mechanical model.

On the other hand, MII is very well suited to investigate longer timescale mechanical responses, including "active" behavior such as cytoskeletal remodeling and cell motility, because unlike most competing technologies, it does not require the filtering out of low frequency motions to achieve accuracy, and the absolute height of the probe over the substrate is measured with high precision (<0.2%) every measurement cycle. In fact, a subset of the creep curves we recorded showed time-varying behavior consistent with an active mechanical response, such as the cell lifting the microreflector several hundred nanometers while under load. The duration of the force cycle, 100 s, was within the time-scale of active mechanical responses by the cell, such as lamellepodial extension/retraction, and cytoskeletal tensioning by molecular motors (see, e.g. Tamada et al., (2004) Developmental Cell 7, 709-718; Giannone et al., (2004) Cell 116, 431-443).

Optical magnetic twisting cytometry (OMTC) developed by Fredberg and colleagues (see, e.g. Smith et al., (2003) American Journal of Physiology-Lung Cellular and Molecular Physiology 285, L456-L463; Fabry et al., (2001) Journal of Applied Physiology 91, 986-994; Mijailovich et al., (2002) Journal of Applied Physiology 93, 1429-1436; Maksym et al., (2000) Journal of Applied Physiology 89, 1619-1632) is the only other technique capable of measuring the mechanical properties of individual live cells with a throughput and sensitivity comparable to MII. We do not include in this discussion the OMTC-related studies that utilize very high optical magnifications (see, e.g. Hu, S. H., Eberhard, L., Chen, J. X., Love, J. C., Butler, J. P., Fredberg, J. J., Whitesides, G. M. & Wang, N. (2004) American Journal of Physiology-Cell Physiology 287, C1184-C1191).

The primary difference between the two methods is that with MII the mechanical properties of the cell are measured by indentation perpendicular to the cell surface, whereas OMTC measures mechanical shear in the x-y plane of the cell membrane. Aside from the orientation-specific mechanical information obtained, z-axis indentation vs. surface twisting (shearing) has several advantages. It does not require that the probe be tethered to cell surface receptors as in the case of twisting measurements (see, e.g. Mijailovich et al., (2002) Journal of Applied Physiology 93, 1429-1436), and because the magnetizing force and the indenting force are aligned in MII, there is no limit to the maximum magnetic field which can be applied. In OMTC the actuating (twisting) field is perpendicular to the probe's magnetic moment, and thus is limited to less than ~100 Gauss in order to avoid demagnetizing the probe. In both methods, the measurement of absolute mechanical constants using surface-bound probes requires assumptions about the probe-cell contact area which are difficult to validate in situ; this is a concern common to magnetic/optical bead twisting and pulling methods, as well as AFM in some cases.

We estimate that both methods have a similar dynamic range of measurable elastic moduli, from tens of Pascals to 100+ kiloPascals. The effective throughput, which is limited by the field of view, is similar and perhaps several times larger for MII vs. OMTC, we believe. OMTC claims positioning accuracy of 5-10 nm versus 10-20 nm for VEII, although in OMTC this is achieved using phase-locked detection, not a requirement but easily implemented in MII. Unlike OMTC, AFM, and some other optical techniques, MII determines absolute cell height every measurement, to ~0.3% accuracy, and has a vertical range of millimeters. This allows MII to capture dynamic changes in cell shape and multi-cell structures, without compromising sensitivity. Also, knowing the thickness of the cell below the probe is critical to accurate mechanical modeling of cells in some cases (see, e.g. Dimitriadis et al., (2002) Biophysical Journal 82, 2798-2810).

OMTC utilizing phase-locked detection has a wide temporal dynamic range, from 0.01 Hz to 100+Hz. Our study utilized a temporal sampling rate of 0.1 Hz. However, this is not a fundamental limitation of MII. We have used phase-locked detection to measure nanometer motion of MEMS structures up to 1 MHz with the MII optical system (see, e.g. Reed et al., (2006) Nanotechnology 17, 3873-3879), and we expect that this could easily be translated to live cell measurements.

Finally, MII may prove to be more scaleable than OMTC, which has been optimized over several years to achieve spatial sensitivity of 5-10 nm, or 0.008 fractional pixels, which studies suggest is at or near the practical limit of non-interferometric particle tracking (see, e.g. Cheezum, M. K., Walker, W. F. & Guilford, W. H. (2001) Biophysical Journal 81, 2378-2388; Carter et al., (2005) Physical Biology 2, 60-72). On the other hand, the accuracy of measurement in the z-axis using vertical scanning interferometry is theoretically insensitive to magnification, for surfaces with low curvature (see, e.g. Olszak et al., (2001) Laser Focus World 37, 93-95; Olszak et al., (2003) Optical Engineering 42, 54-59). At its limit, interferometric microscopy can operate with magnifications as low as 1×, or approximately 5 mm×5 mm field of view. If this level of resolution could be achieved with microreflectors, spherically-shaped or otherwise, it would translate to the ability to perform cell mechanical measurements simultaneously over an area in excess of 600× conventional methods. This would enable longitudinal time studies of mechanical properties, where not only single-cell, but simultaneous cell-cell interaction and the effect of long-scale (hundreds of microns) physical or chemical gradients can be observed.

The primary conclusions of this study are as follows: MII is capable of axially tracking magnetic microreflectors, with <20 nm spatial precision, in the optically complex environment of live cell culture. Combined with a 20 pN-to-20 nN range of achievable forces on a typical microreflector, MII can determine the elastic moduli of live cells, through nano-indentation, over a wide dynamic range, from several Pa up to ~200 kPa. MII attained excellent positional resolution at low effective magnification (spatial sampling ~500-900 nm per pixel), permitting simultaneous measurement of up to 100 probes.

Using soft polyacrylamide gels of known stiffness, we demonstrate an absolute measurement accuracy slightly exceeding that of AFM indentation in a similar experimental configuration (6% standard error on a gel with Young's modulus of 4 kPa, n=23). Using MII we determine the quasi-static mechanical properties of populations of NIH 3T3 and HEK 293T fibroblasts, we determined the absolute values of the mechanical constants which are in excellent agreement with results from other nanomechanical probing methods.

Our results show that MII is an effective, high throughput technique for measuring cellular mechanical properties through indentation normal to the cell surface. This represents a significant throughput advance over AFM, and other optical approaches, such as confocal microscopy or microfluidic optical stretchers, which cannot accurately measure mechanical properties of large arrays (hundreds) of cells simultaneously, with single-cell specificity (see, e.g. Cheezum, M. K., Walker, W. F. & Guilford, W. H. (2001) Biophysical Journal 81, 2378-2388; Carter et al., (2005) Physical Biology 2, 60-72). The mechanical dynamic range and effective magnification of MII equals or exceeds existing wide-field optical particle tracking techniques (see, e.g. Fabry et al., (2001) Journal of Applied Physiology 91, 986-994), which implies that the two could be used in combination to conduct rapid, fully-3D mechanical probing of large arrays of live cells.

Example 2: Live Cell Interferometry Reveals Cellular Dynamism During Force Propagation This example provides an illustration of how to employ live-cell-interferometry (LCI) to visualize the rapid response of a whole cell to mechanical stimulation, on a time scale of seconds, and we detect cytoskeletal remodeling behavior within 200 seconds. This behavior involved small, rapid changes in cell content and miniscule changes in shape; it would be difficult to detect with conventional or phase contrast microscopy alone, and is beyond the dynamic capability of AFM. We demonstrate that LCI provides a rapid, quantitative reconstruction of the cell body with no labeling, which is highly complementary to traditional microscopy and flow cytometry, which require cell surface marker detection and/or destructive cell fixation for labeling.

Briefly, mammalian cells exhibit continuous regional motion and shape changes controlled by a dynamic cytoskeleton. The movements of a cell are orchestrated by a dynamic cytoskeleton that extends from the fluid lipid bilayer and underlying actin cortex to deep within a cell. The mechanical scaffold of each cell is composed of relatively stiff components including actin microfilaments, intermediate filaments, microtubules and a myriad of crosslinking, motor and regulatory proteins that maintain structure and control dynamism. Numerous studies link these cytoskeletal structures to biochemical signal transduction pathways to regulate cellular processes including adhesion, motility, gene expression and differentiation (see, e.g. Kumar et al., Biophysical Journal 2006, 90, 3762-3773; Matthews et al., Journal of Cell Science 2006, 119, 508-518; Felsenfeld et al., Nature Cell Biology 1999, 1, 200-206; Lee et al., Nature 1999, 400, 382-386; Yauch et al., Journal of Experimental Medicine 1997, 186, 1347-1355; Felsenfeld et al., Nature 1996, 383, 438-440; Chicurel et al., Nature 1998, 392, 730-733). A key challenge that remains is connecting specific structures and signaling to the changing biophysical properties of the cell and vice-versa. A critical issue in probe-based measurements of cell mechanics, such as AFM and optical/magnetic tweezers, is the speed and degree to which a mechanical force exerted by a probe propagates across the cell body (see, e.g. Van Vliet et al., ACTA MATERIALIA 2003, 51, 5881-5905). This is seldom documented because observing deformation of the entire cell body with required speed and accuracy (~1% local deformation) is experimentally complex, for a variety of reasons. For example, in most cases AFM cannot accurately image the membrane of an entire mammalian cell at the rate of 1-2 Hz, due to the softness of the cell membrane. Bead-based approaches, such as magnetic and optical traps, track the motion of the bead itself and not the surrounding cellular material which is unlabeled. Labels can be introduced but this adds considerable complexity. With phase contrast methods organelles themselves can serve as displacement probes, but they are not uniformly distributed, which is a major constraint when investigating dynamic structure is the cell periphery such a filopodia.

These problems are addressed by the imaging technique disclosed herein, called live cell interferometry (LCI), to directly assess the propagation of strain throughout a single cell in response to locally applied force. By measuring changes in optical path length distribution across many points within the cell simultaneously, we could determine the corresponding redistribution of cellular constituents, and thus could quantify responses of the cell body distal to the point of applied force in real time and without labeling. The imaging system (FIG. 1A) consists of an optical microscope with a Michelson interference objective, a fluid-filled live-cell observation chamber with a reflective floor, and a matched reference chamber containing only fluid. It operates as follows: The illumination wavefront incident on the observation chamber travels through the transparent fluid (culture media) and the transparent cell body, and is returned to the interferometer by the reflective substrate. The index of refraction of the culture media and the cell body are so close in value that there is very little reflection of the light from the cell-fluid interface. However, the difference in the index of refraction of the fluid and cell is sufficiently large for the detection of changes in optical path length introduced by the cell as the light travels through it and is reflected back from the substrate. The optical path length is the geometrical path the wavefront travels times the index of refraction distribution $n(z)$ of the media at a given point. Because the light reflects from the substrate and returns to the objective, it travels twice the same geometric distance z, the optical path length can be expressed as:

$$\text{Sample Optical Path Length} = 2\int zn(z)dz \quad (1)$$

While for the light traveling through the reference chamber fluid, having a uniform distribution of index of refraction, the optical path length it is simply:

$$\text{Reference Optical Path Length} = 2zn_{fluid} \quad (2)$$

Figure 7:
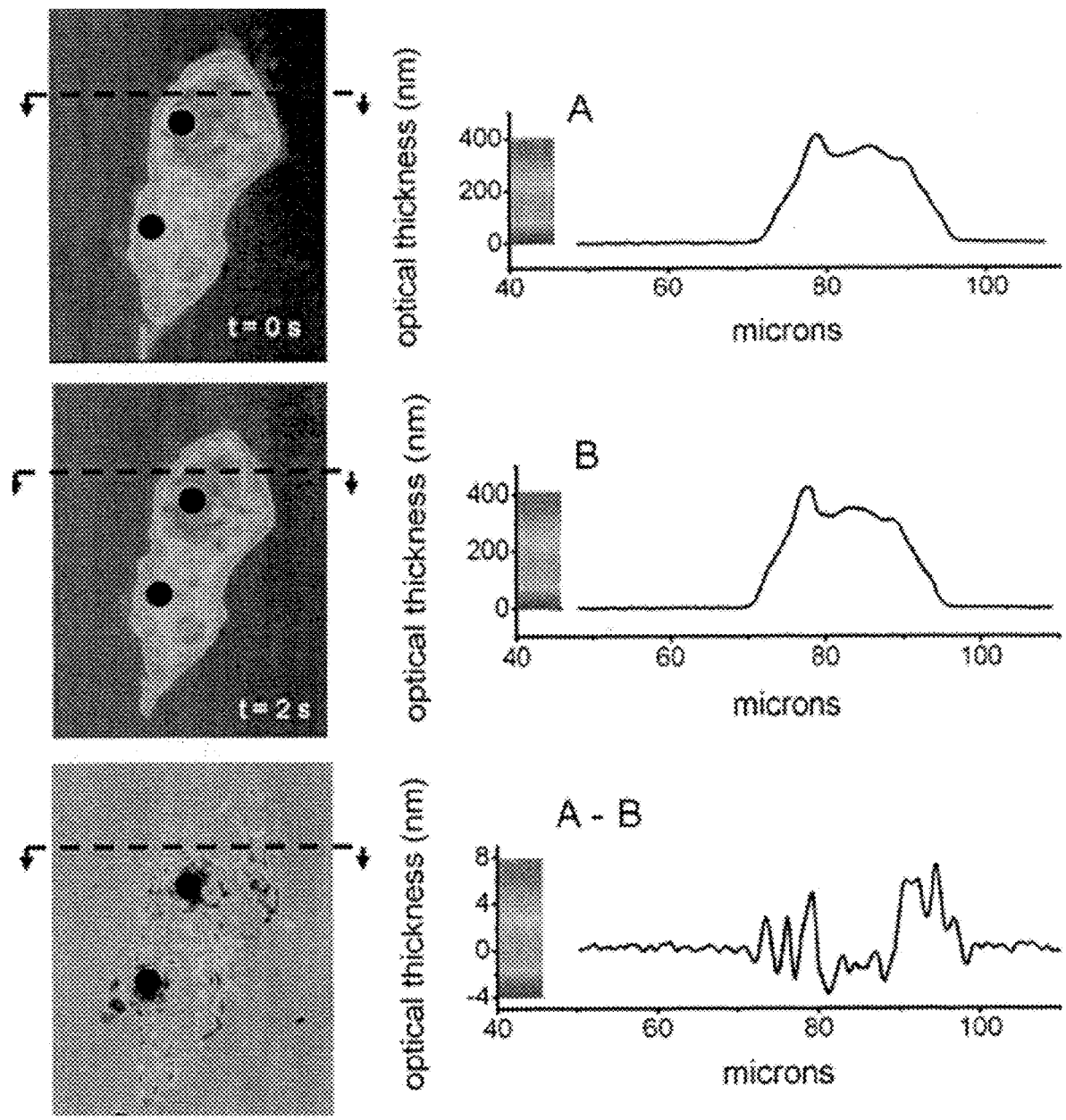
FIG. 7 Upper left panels show LCI interferometric images of a live NIH3T3 fibroblast taken two seconds apart, before and after the application of force by two magnetic microspheres on their surface (indicated by black disks). The optical thickness cross-sections are displayed to the right. The change in optical thickness between the two images is readily apparent in the differential LCI image, below, created by subtracting the bottom from the top LCI image. As shown by the associated panels on the right, the optical thickness of the cell body ranges from 0-400 nm and the change in optical thickness detectable in the differential LCI image ranges from −6 to +8 nm.

In the LCI technique, this difference in optical path is recorded as a shift in phase between the sample observation and reference beams (see, e.g. Creath K; Schmit J. Phase shifting interferometry. In: Guenther B, editor. Encyclopedia of Modern Optics. Boston: Elsevier Academic Press; 2005. p. 364-374). The resulting LCI phase image shows a distribution of the optical path lengths in the field of view of the objective. Obtained in this way the signature of the cell shows that the optical path length is longer through the cell versus fluid by about 0-400 nm (FIG. 7). This data agrees with the assumption that the index of refraction of the fluid is about 1.33, the index of refraction for the cell body is 1.4-1.5 and the maximum thickness of the cell is about 5-8 microns. Thus, the measured optical path length represents the distribution of cells thickness and material index of refraction together.

By comparing optical path length images taken at two consecutive time points, we determined very precisely local shifts of material within the cell. This is illustrated in FIG. 7. We were able to reliably detect changes in optical path length as small as ~1 nanometer. Since the cell body appears to be between 0 to 400 nm in optical thickness, this corresponds to the ability to detect <1% changes in optical path length over large portions of the cell.

We recorded shifts in optical thickness in regions adjacent to magnetic microspheres undergoing cyclical indentations at 0.05 Hz for 200 s or 10 cycles (FIGS. 8A-8F). Two 5 μm diameter microspheres were evaluated simultaneously on an elongated NIH 3T3 fibroblast. The maximum applied force was ~200 pN for each microsphere. The mechanical linkage between the force-driven and undriven regions of the cell was measured as the change in the optical thickness profiles over each indentation cycle. A shift in cell content was not readily apparent in either the intensity image or the LCI image itself, but was detected by comparing the difference between two LCI images. This differential LCI image provided a quantitative measure of the redistribution of material in the cell in response to the indenting body for any two time points. In these experiments two features became apparent: first, the strain field due to the indenting sphere extends across the entire cell, in a pattern that suggests displacement of core underlying, rigid structures (FIG. 9); and second, the indentation produces an immediate, synchronized and laterally continuous increase in material at the cell periphery, consistent with pressure-driven flow. Detecting these rapid rearrangements in the local material density would be difficult with non-interference-based optical methods, and is beyond the dynamic capability of AFM. Optical waveguides have been used to observe the nanometer-scale deformation of a metallic substrate surface caused by a plant fungus. This method is confined to reflective surfaces however, whereas LCI measures subtle index of refraction changes of a volume of transparent material (the cell body).

Figures 8A, 8B, 8C:
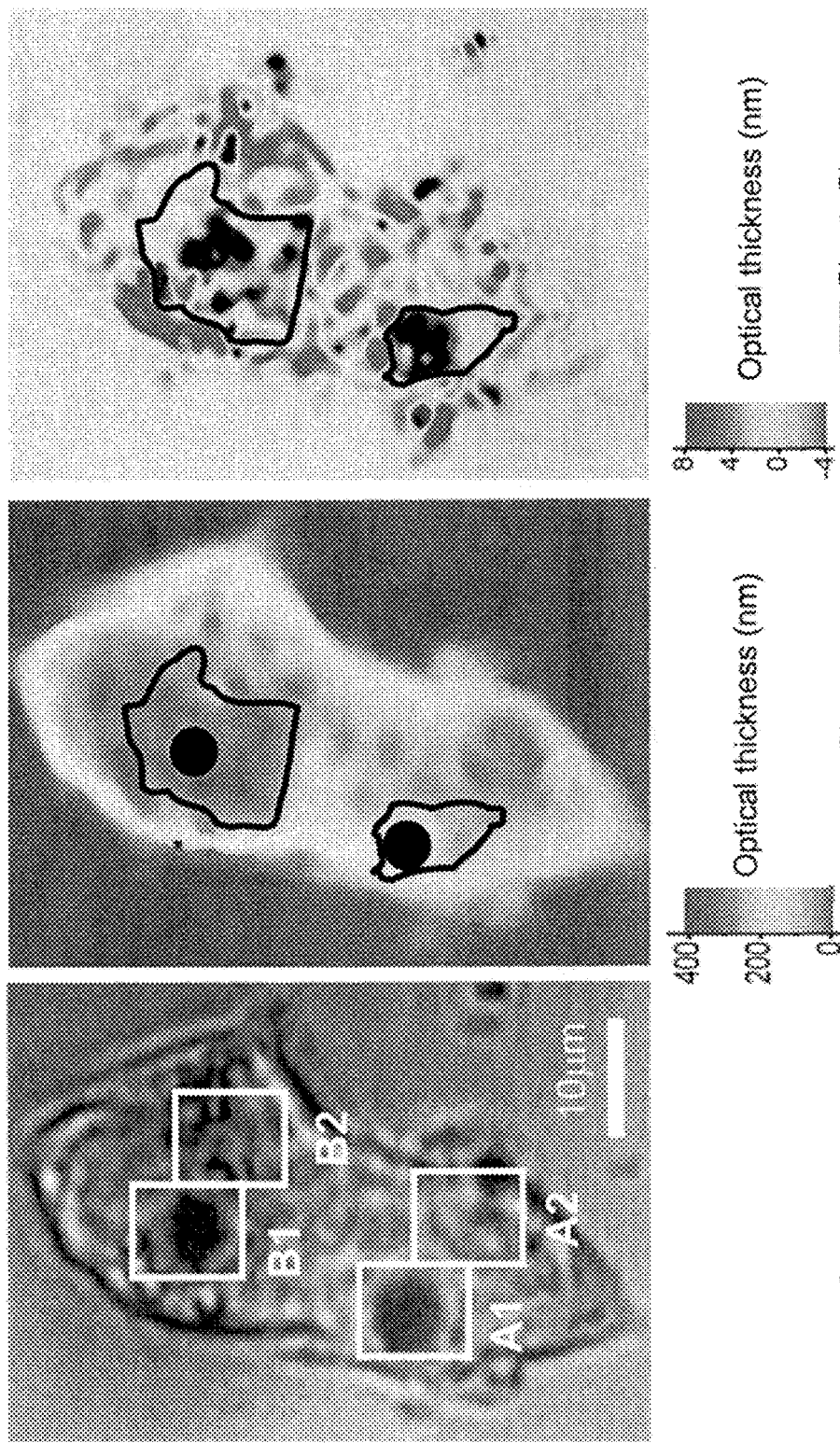
FIGS. 8A-8C show intensity (left) and LCI interferometric (right) images of a single NIH3T3 cell with two magnetic microspheres on the cell surface. As force was applied to the probes, the change in optical path length in the regions directly surrounding each probe (A1 and B1), and the adjacent regions (A2 and B2) was tracked. A 200 pN peak-to-trough, 0.05 Hz cyclical force was applied to the microspheres for 200 s.
Figure 8D:
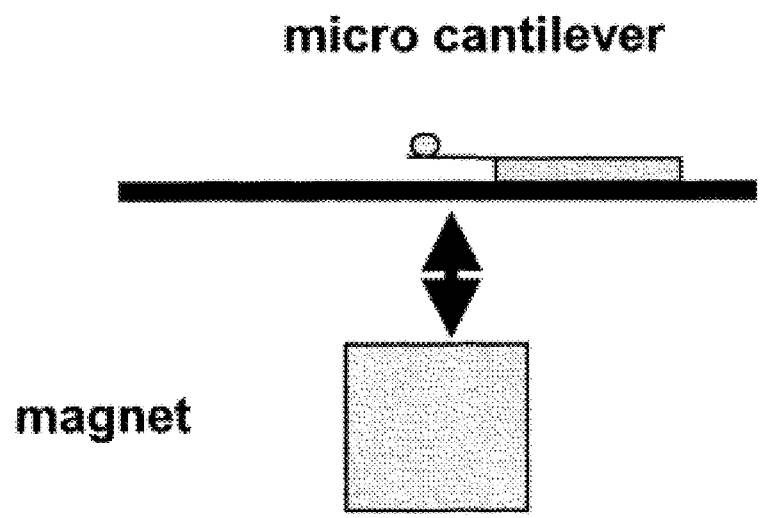
FIG. 8D shows a schematic of the geometry used for calibrating the magnetic force applied to each microreflector.
Figure 8E:
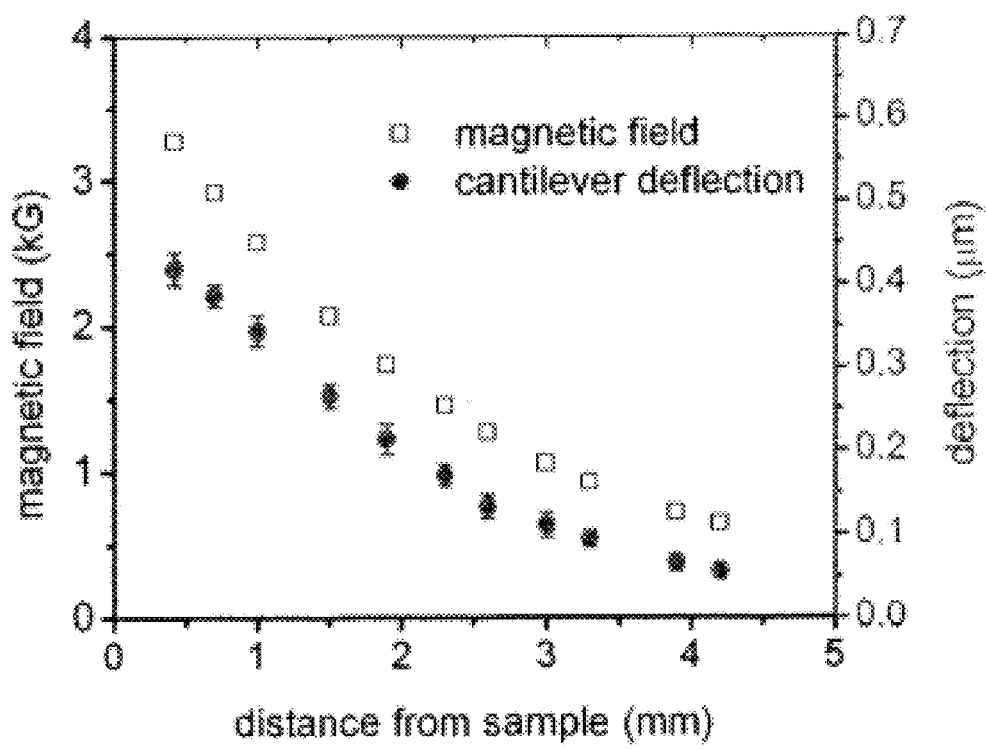
FIG. 8E shows a force calibration curve and associated magnetic field, as a function of distance between the magnet face and the sample.
Figure 8F:
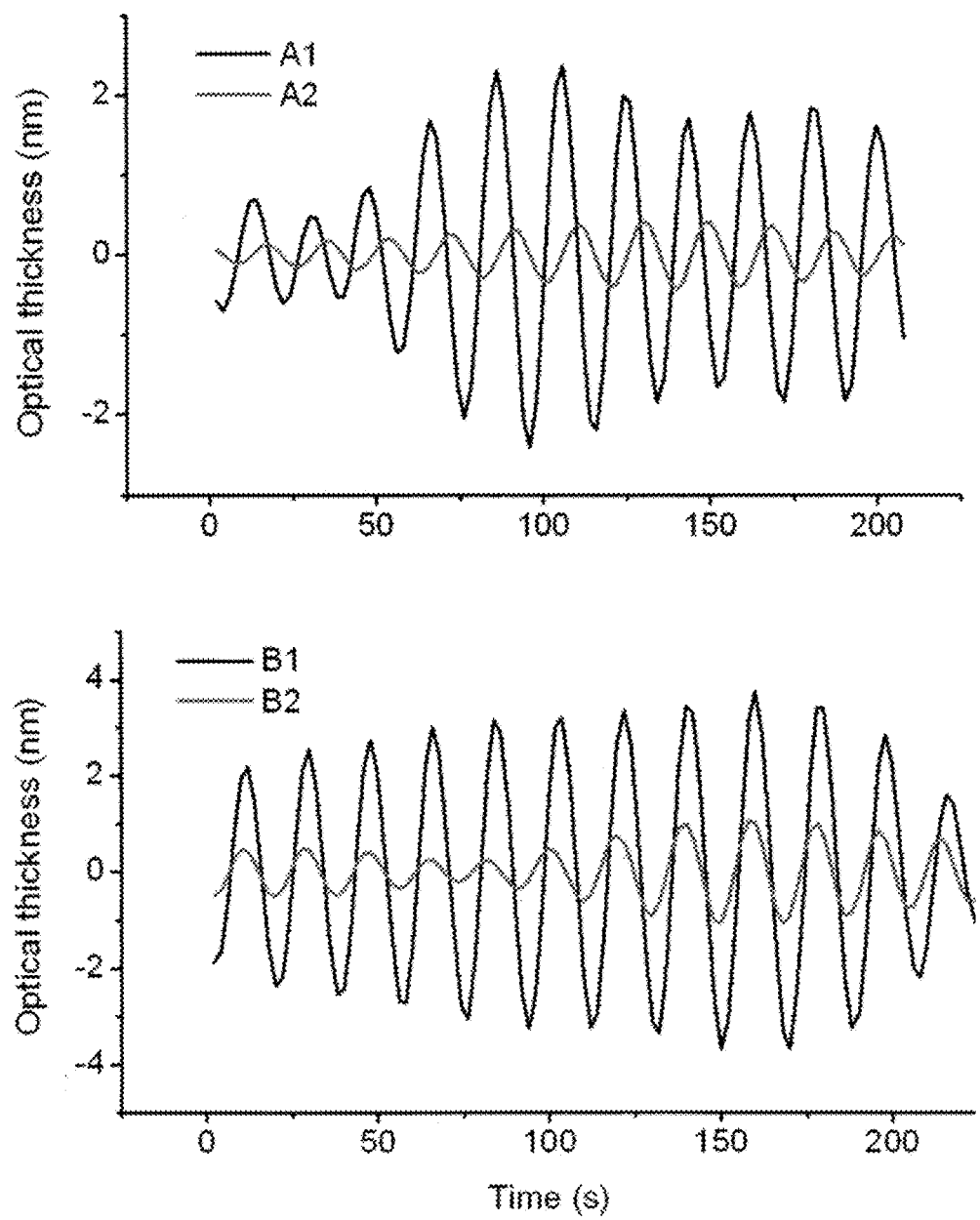
FIG. 8F shows the average time-varying optical thickness measurements for four regions within the cell depicted in FIG. 8A. Individual data points are collected at two second intervals, for a 0.5 Hz sampling frequency. For clarity, the data have been band pass filtered with a 0.05 Hz center frequency.
Figure 9:
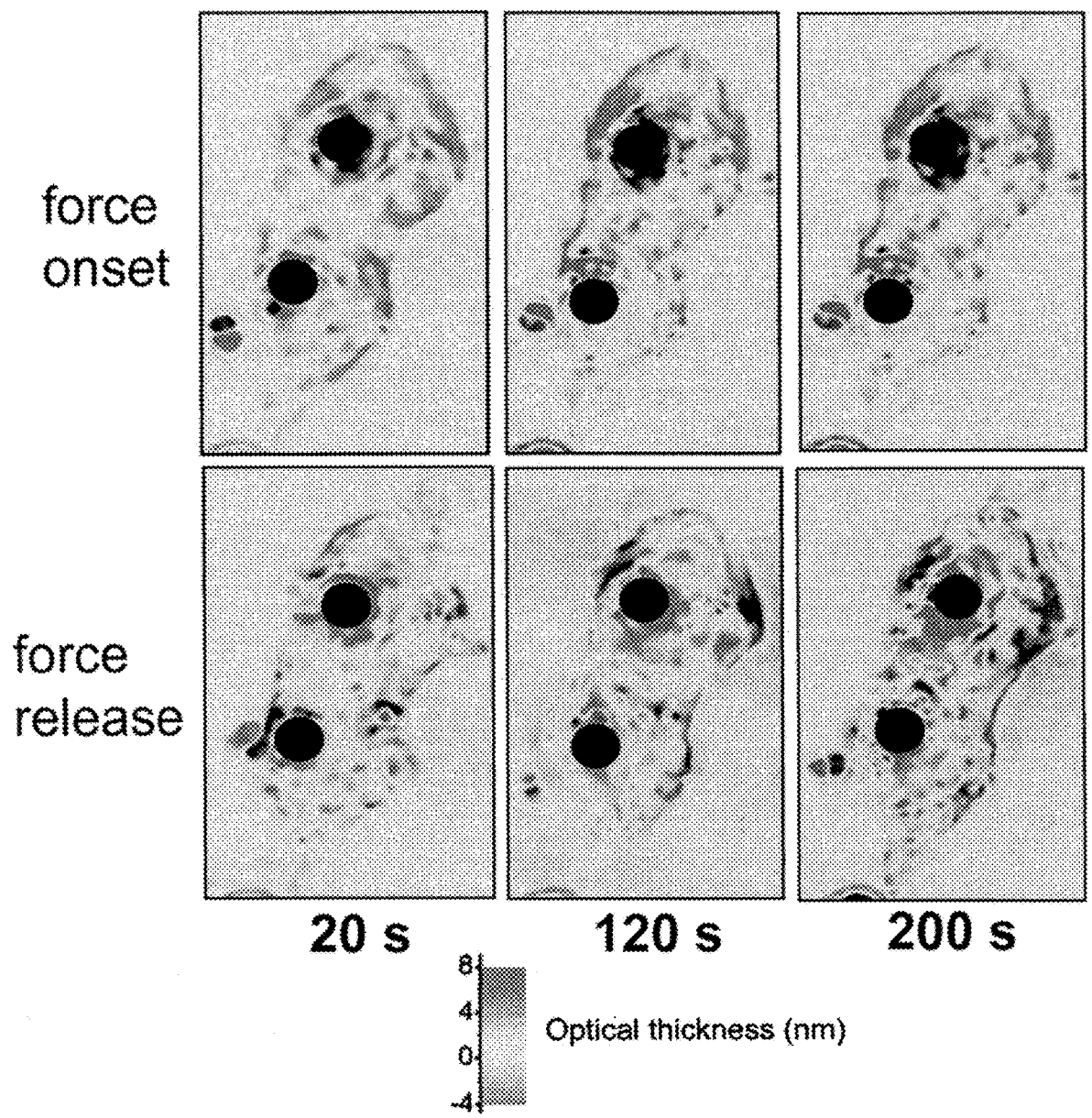
FIG. 9 shows differential LCI images of three indentation cycles at 20, 120 and 200 s. The top panel of images shows the effect of probe indentation immediately after force is applied, and the bottom panel shows the corresponding rebound after force is removed. The pattern and magnitude of material redistribution appears to change with time.
Figure 10A:
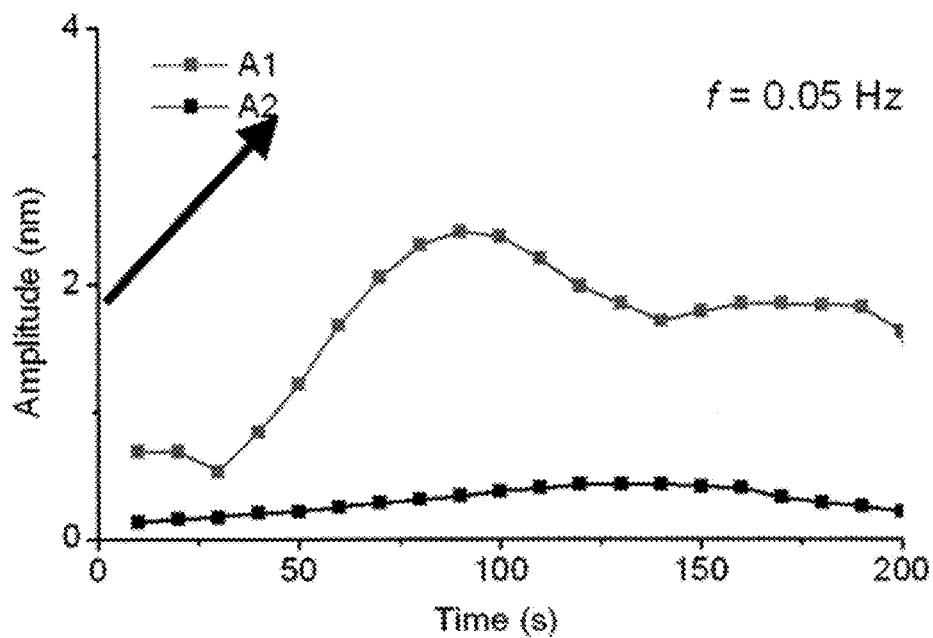
FIGS. 10A and 10b show the effect of 0.05 Hz cyclical loading on the adjacent cellular regions is seen as a change in average optical thickness. The cyclic amplitude of the time-varying change optical thickness of regions A1 and A2 (FIG. 10A) evaluated at frequency=0.05 Hz show the relationship between the driven and undriven portions of the cell body (top). Similar behavior is seen in regions B1 and B2 (FIG. 10B). The regions adjacent to the probes show a clear response, indicating that the strain field within the cell body extends several probe diameters laterally. Individual data points are collected at two second intervals, for a 0.5 Hz sampling frequency. For clarity, the data have been band pass filtered with a 0.05 Hz center frequency.
Figure 10B:
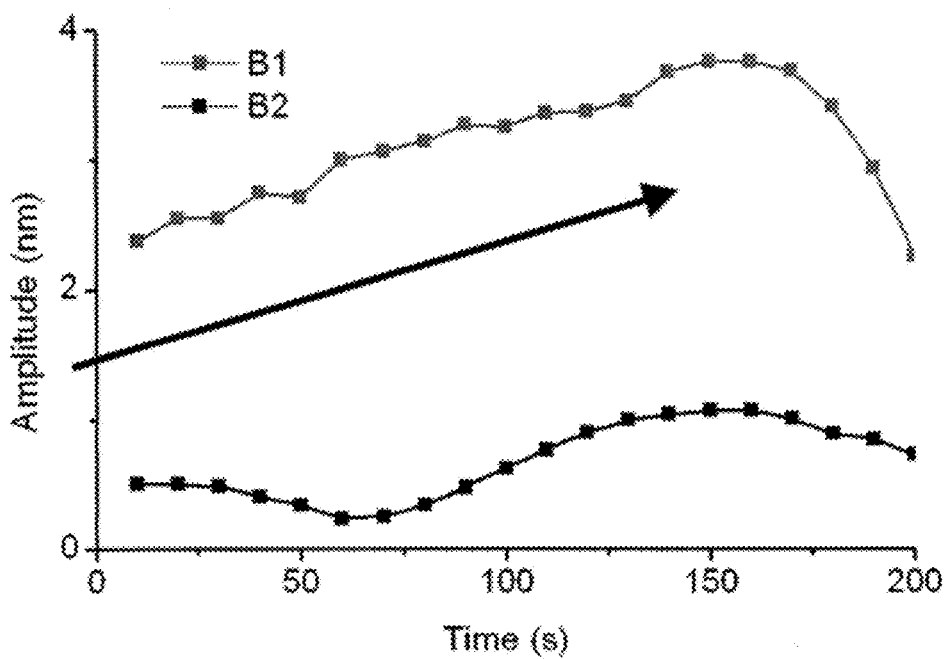

We analyzed the time-dependence of the content shift between specific regions of the cell by measuring the change in average optical thickness within four sub-regions of the cell body (FIG. 8A left). The undriven regions responded at the same frequency as the driven regions, but with a temporal delay, as would be expected from a viscoelastic material (FIG. 8A). The amplitudes of motion of both the driven and undriven regions increased with time (FIGS. 10A and 10B). In the driven region A1 the amplitude peaked at ~100 sec and leveled off, while the amplitude of the other region, B1, peaked later (~150 sec), and then began to decline. This behavior suggests that the local compliance of the cell changed with time, and that this change was distributed heterogeneously within the cell.

Figure 11:
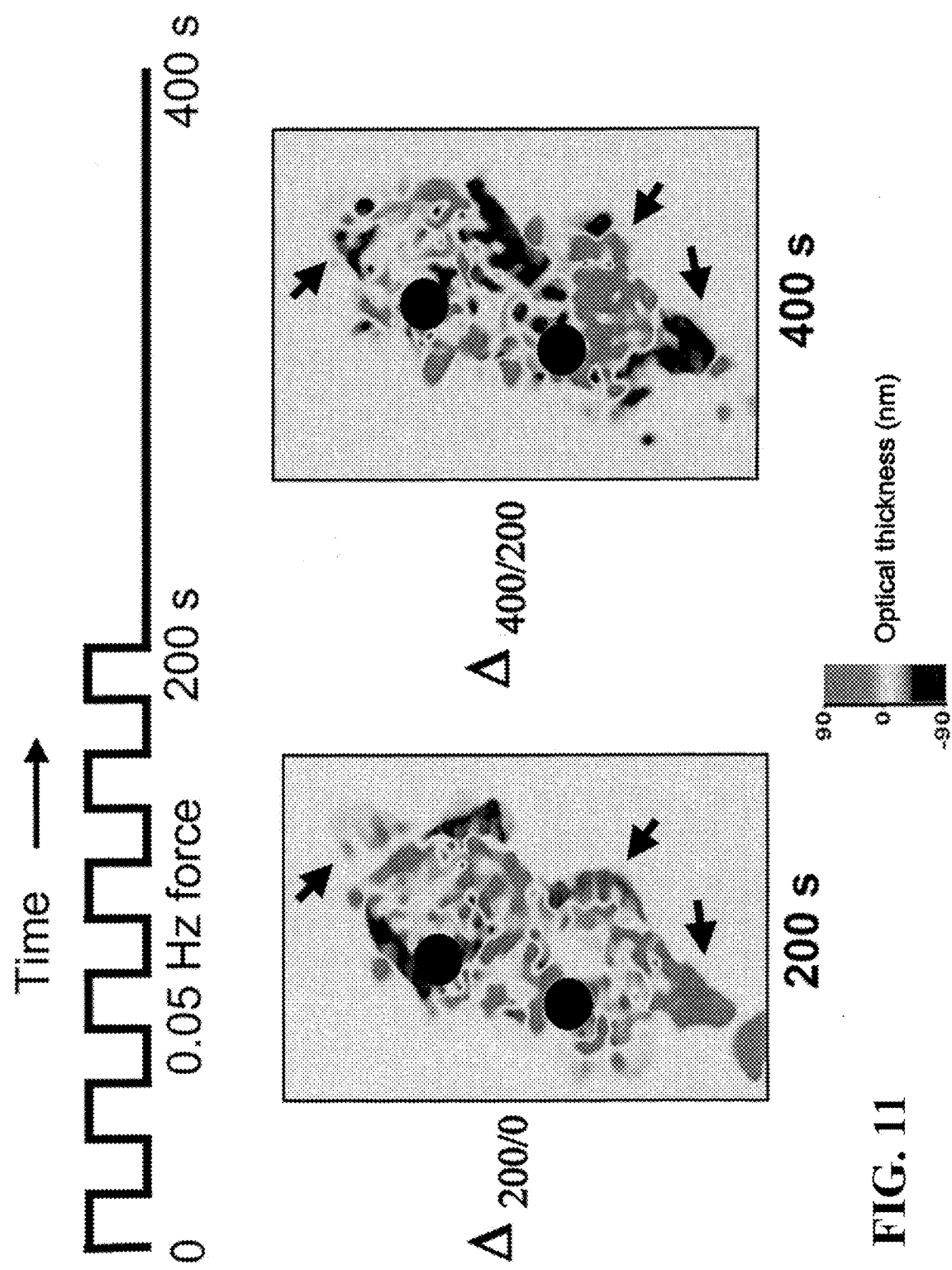
FIG. 11 shows the Differential LCI comparison of material distributions after t=200s of cyclically-applied force Δ200/0 (left panel) and at 200s after cessation of force t=400s; Δ400/200 (right panel). The positions of the microspheres are indicated by black circles. Arrows denote regions of material redistribution within the cell.
Figure 12A:
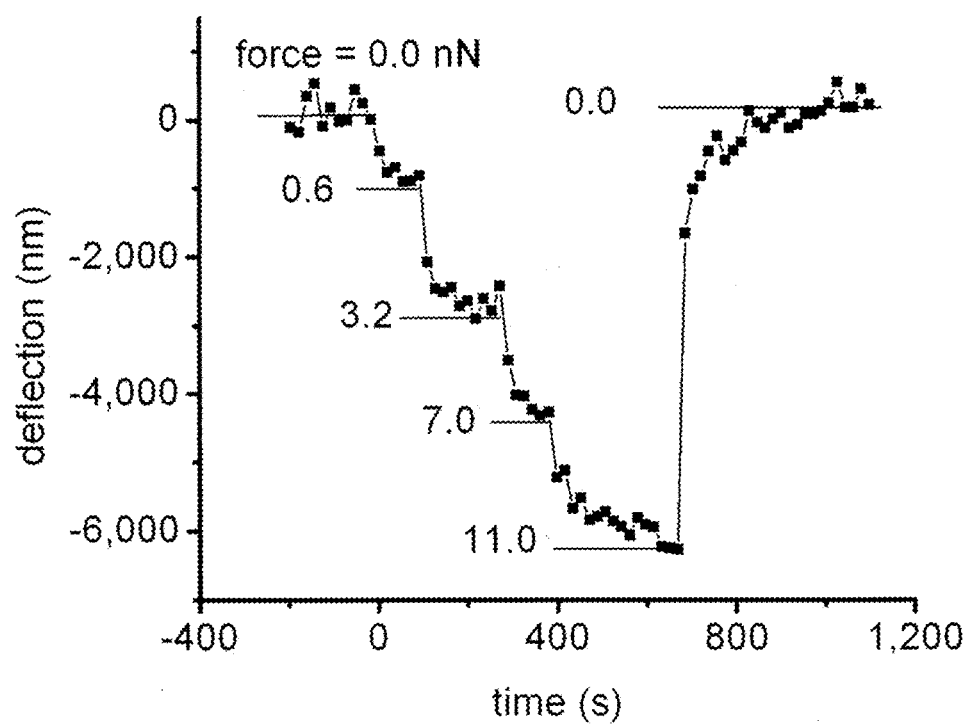
FIG. 12A shows a graph of a range of a typical range of forces applied to a 5-10 micron reflector on a cell over time and the associated deflection.
Figure 12B:
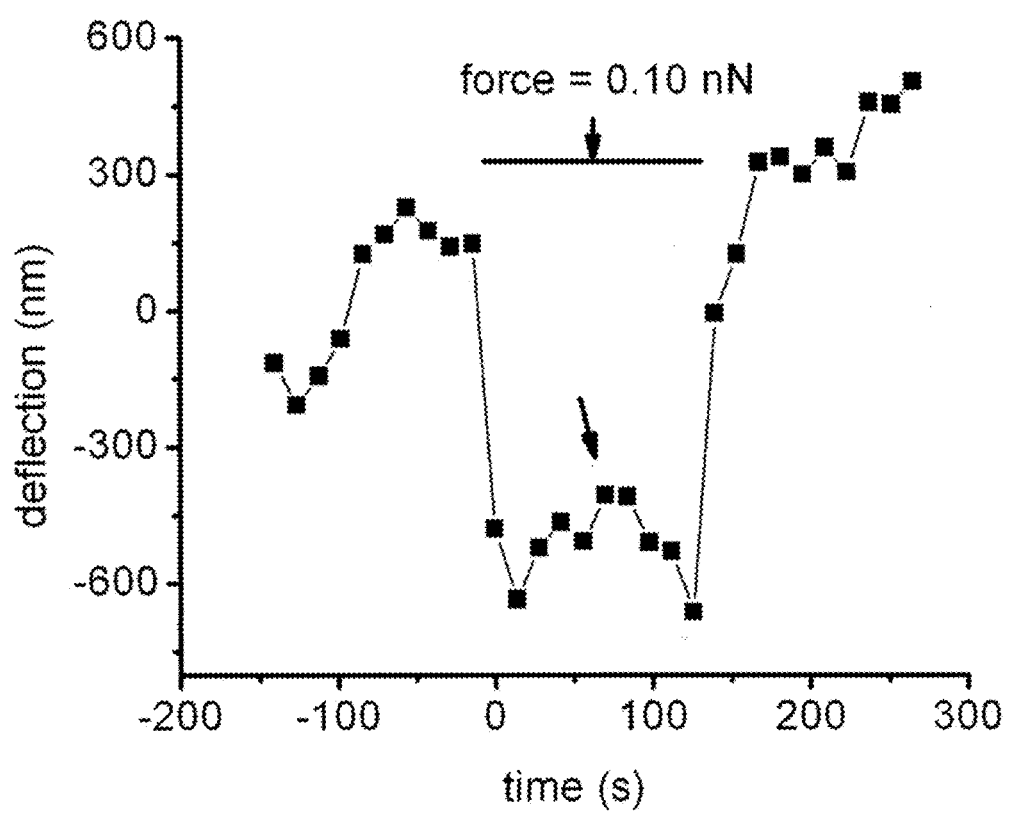
FIG. 12B shows a graph of forces applied to a cell over time and the associated active responses from the cell.

After 200 s of cyclically applied force, there was a noticeable, non-transient redistribution of material within the cell body. The magnitude of this shift was larger than the transient response, with maximum local changes in content of 10-15%, but was still observable only in the differential LCI images (FIG. 11). Material accumulated in the center of the cell, preferentially along the "backbone" of the long axis. Lamellepodia also formed at either end of the cell parallel to the long axis. There was an opposing loss of material at the edges of the cell adjacent to the two microspheres, parallel with the short axis of the cell. Notably, the regions with the largest decrease in material over 200 s corresponded to the regions of the cell which saw the most transient change in content during each earlier force cycle. The forced motion was ended at t=200 s and the cell was imaged again at t=400 s. By this time, the pattern of material accumulation within the cell had largely reversed, the lamellepodia parallel to the long axis retracted and material accumulated adjacent to each microsphere, parallel to the short axis of the cell. This behavior suggests an active remodelling of the cytoskeleton in response to cyclic loading (see, e.g. Matthews et al., Journal of Cell Science 2006, 119, 508-518). Local force-induced remodeling is known to begin within tens of seconds following a mechanical stimulus (see, e.g. Hayakawa et al., Experimental Cell Research 2001, 268, 104-114). The edges of the cell retracted and then re-extended at a linear velocity of approximately 180 nm per second, which is consistent with active, actinomyosin-driven motion. The accumulation of material along the cell 'backbone' is also consistent with enhanced cytoskeletal contractility, known to occur in some cells following forced stretching or similar mechanical deformations (see, e.g. Hayakawa et al., Experimental Cell Research 2001, 268, 104-114; Deng et al., American Journal of Physiology-Cell Physiology 2004, 287, C440-C448; Smith et al., American Journal of Physiology-Lung Cellular and Molecular Physiology 2003, 285, L456-L463). There was a considerable transient change in content near the cell periphery during each force cycle, the same areas that showed the greatest non-transient shift in material accumulation. Overall, this behavior demonstrates a global coordination and reorientation of the cell structure in response to a local, cyclically-applied stress. The mechanisms triggering this content rearrangement could include both phosphatase-integrin complex activation (see, e.g. Matthews et al., Journal of Cell Science 2006, 119, 508-518; Felsenfeld et al., Nature Cell Biology 1999, 1, 200-206; Yauch et al., Journal of Experimental Medicine 1997, 186, 1347-1355) and membrane stretch-activated ion channel function (see, e.g. Matthews et al., Journal of Cell Science 2006, 119, 508-518; Felsenfeld et al., Nature Cell Biology 1999, 1, 200-206; Yauch et al., Journal of Experimental Medicine 1997, 186, 1347-1355). The latter have been shown induce tail retraction in migrating keratocytes, and are known to trigger a calcium-dependant signaling cascade that results in the phosphorylation of myosin, leading to retraction of filipodia (see, e.g. Matthews et al., Journal of Cell Science 2006, 119, 508-518; Felsenfeld et al., Nature Cell Biology 1999, 1, 200-206; Yauch et al., Journal of Experimental Medicine 1997, 186, 1347-1355). The synchronized and laterally continuous increase in material at the periphery of the cell in response to indentation seems likely to have disturbed the cell membrane in these areas, and suggests that membrane stretch mechanisms need to be considered (see, e.g. Matthews et al., Journal of Cell Science 2006, 119, 508-518; Sheetz et al., Annual Review of Biophysics and Biomolecular Structure 2006, 35, 417-434).

In many magnetic/optical tweezer experiments, and some AFM experiments, the probe is coated with a peptide ligand to promote specific attachment to cell surface receptors. In theory, this allows a direct mechanical link to the cytoskeleton, which could propagate an applied force to other regions of the cell and a vehicle for studying whole cell mechanical dynamics. However, in practice the degree of attachment to the cytoskeleton is seldom confirmed, and conflicting results have been reported regarding the degree of force propagation (see, e.g. Matthews et al., Journal of Cell Science 2006, 119, 508-518; Bausch et al., Biophysical Journal 1999, 76, 573-579). In some cases experimenters have observed the displacement of organelles or injected particles to infer the strain field, though this produces only a sampling and not a global measurement (see, e.g. Hu et al., American Journal of Physiology-Cell Physiology 2003, 285, C1082-C1090; Bausch et al., Biophysical Journal 1998, 75, 2038-2049). Various labeling schemes can make this sort of measurement more comprehensive, but often require engineered cell lines or tedious labeling procedures that limit their use. LCI is compatible with these existing approaches, and addresses one of their significant weaknesses by globally capturing the redistribution of cell material in response to force. This spatially—and temporally—detailed tracking of cell material also may have utility in improving computational models of cell mechanics, which are now largely phenomenological (see, e.g. Lim et al., Journal of Biomechanics 2006, 39, 195-216; Stamenovic et al., Journal of Theoretical Biology 1996, 181, 125-136; Wang et al., Proceedings of the National Academy of Sciences of the United States of America 2001, 98, 7765-7770; Canadas et al., Journal of Biomechanical Engineering-Transactions of the Asme 2006, 128, 487-495), and have difficulty assigning specific model parameters to discrete mechanical structures within the cell.

Exameplary Methods and Materials

Interferometer.

The measurement of the microspheres was performed on the Veeco interference microscope NT 1100 with a green diode (center wavelength 535 m) used for illumination and 20× 0.28NA Michelson through transmissive media (TTM) interference objective (see, e.g. Reed et al., PROCEEDINGS-SPIE THE INTERNATIONAL SOCIETY FOR OPTICAL ENGINEERING 0277-786X; 2006; VOL 6293 2006, 6293, p. 629301). The NT 1100 in principle is an optical microscope with a Michelson interference objective that allows for the observation of not only lateral features with typical optical resolution (1.16 μm for the 20× objective) but also height dimensions below the scale of one nanometer (see, e.g. Olszak et al., Laser Focus World 2001,37, 93-95). The Michelson interferometer is composed of a beam splitter, reference mirror and compensating fluid cell. The compensation cell is 0.7 mm thick bounded on both sides by 0.5 mm optical windows, thus matching the optical path length of a reflected beam from the test chamber (i.e. matching the optical path difference between the arms). The CCD detector array is 640×480 pixels, which with a 20× objective produces a 315×240 micron field of view and a spatial sampling of 500 nm. The phase shifting interferometry (PSI) method was used to capture phase images of the cell bodies in situ. During measurement, a piezoelectric translator decreases the light path a small amount causing a phase shift between the test and reference beams. The system records the irradiance of the resulting interference pattern at many different phase shifts and then converts the irradiance to phase wavefront data by integrating the irradiance data using a PSI algorithm. The phase data are processed to remove phase ambiguities between adjacent pixels. Average optical thickness measurements for the regions of interest A1-A2 and B1-B2 were calculated by averaging the optical thickness across all pixels within the region, followed by subtracting the average thickness value from a similarly-sized region adjacent to the cell containing no material. The external region served as a local reference for zero optical thickness. To determine the response to the cyclicly-applied force (f=0.05 Hz), the time varying data, sampled at 2 second intervals, was bandpass filtered around a center frequency f=0.05 Hz.

Cell Chamber.

The cell chamber body was constructed from machined non-magnetic stainless steel. Resistive heating elements with internal thermistors, driven by a feedback controlled power supply, were used to regulate the chamber temperature to within 0.5 degrees of 37 C. The fluid sample was contained within a 13 mm diameter, 0.7 mm thick sub chamber, having a 1 mm thick optical window on top and a 0.2 mm thick silicon floor.

Microspheres.

Micron-sized elemental nickel microspheres were obtained from Duke Scientific as a dry powder. An aqueous suspension of microspheres was diluted 4:1 with 0.2% poly-L-lysine aqueous solution (Sigma) to inhibit aggregation and improve adhesion to the cell body. This microreflector solution was shaken vigorously before application to suspend any sedimented particles and reduce aggregates. 200 µL of the suspension was pipetted onto the sample and the microspheres allowed to settle for 1 minute.

Magnetic Force Control.

Magnetic force was applied to the microspheres using a cylindrical rare earth magnet 7 mm in diameter by 21 mm long, oriented axially along the vertical direction below the test chamber. The magnet was positioned with a feedback controlled motorized micrometer, capable of <10 µm accuracy. The magnitude of magnetic flux perpendicular to the vertical axis, as a function of axial distance, was measured with a miniature Hall probe (2×2 mm) and a F. W. Bell 5180 gaussmeter accurate to 0.1 G. In the "off" position, the magnet was lowered to >4 cm below the sample, resulting in negligible field at the sample point. The magnet was positioned coaxially with the optical axis to ensure a uniform magnetic flux across the viewing area (~300×300 µm with the 20× objective). The force applied to the nickel microspheres as a function of magnet position was determined using microcantilever arrays tipped with elemental nickel or several uniformly magnetic microspheres (Compel 8 um carboxylated microspheres, Bangs Labs). Each microcantilever is 500 microns long by 100 microns wide and 0.9 microns thick, with a nominal spring constant of 0.01 N/m. These commercially available arrays were produced by the IBM Zurich Research Laboratories using a proprietary dry etch, silicon-on-insulator (SOI) process. Using the optical profiler, the deflection of the reference cantilever could be determined to better that 1 nm. The volume magnetic moment for pure nickel (55 emu/g) was assumed for both the microspheres and the nickel film deposited on the cantilever tips. Pure nickel is completely magnetically polarized at field strengths of 200 G and higher, while the lowest field strength used in measurements was 500 G. Preceding measurements, the magnet was raised to with 1.5 mm of the sample, corresponding to a ~2 kG flux at the sample point, to ensure that the microspheres' magnetic moments were oriented axially.

Discussion of the Effect of Microsphere Size on Cell Dynamics

In general, micron-sized magnetic microspheres (~5 microns) of are a well tested method used to apply mechanical stimulation to mammalian cells in culture (see, e.g. Trepat et al., Nature 2007, 447, 592-U7; Fernandez et al., Biophys. J. 2006, 90, 3796-3805; Trepat et al., Journal of Applied Physiology 2005, 98, 1567-1574; Fisher et al., Rev. Sci. Instrum. 2005, 76; de Vries et al., Biophys. J. 2005, 88, 2137-2144; Lenormand et al., J. R. Soc. Interface 2004, 1, 91-97; Hu et al., American Journal of Physiology-Cell Physiology 2004, 287, C1184-C1191; Deng et al., American Journal of Physiology-Cell Physiology 2004, 287, C440-C448; Hu et al., American Journal of Physiology-Cell Physiology 2003, 285, C1082-C1090; Mijailovich et al., Journal of Applied Physiology 2002, 93, 1429-1436; Fabry et al., Journal of Applied Physiology 2001, 91, 986-994; Bausch et al., Biophys J 2001, 80, 2649-57; Fabry et al., Journal of Magnetism and Magnetic Materials 1999, 194, 120-125; Bausch et al., Biophys. J. 1999, 76, 573-579; and Bausch et al., Biophys. J. 1998, 75, 2038-2049, the contents of which are incorporated by reference).

Other methods with larger physical footprints and/or larger forces have also been used successfully. These include whole cell aspiration into micropipettes (see, e.g. Hochmuth et al., J. Biomech. 2000, 33, 15-22) glass micro-needles and punch indentation (see, e.g. Desprat et al., Biophys. J. 2005, 88, 2224-2233; Engler et al., Surf. Sci. 2004, 570, 142-154; Koay et al., J. Biomech. Eng.-Trans. ASME 2003, 125, 334-341; Shin et al., J. Orthop. Res. 1999, 17, 880-890; and Thoumine et al., J. Cell Sci. 1997, 110, 2109-2116), substrate pulling (see, e.g. Hayakawa et al., Experimental Cell Research 2001, 268, 104-114; Wang et al., Annals of Biomedical Engineering 2005, 33, 337-342; and Schaffer et al., J. Orthop. Res. 1994, 12, 709-719), fluid shear (see, e.g. Li et al., Journal of Biological Chemistry 1997, 272, 30455-30462; and Tseng et al., Circulation Research 1995, 77, 869-878. and AFM cantilevers (see, e.g., Mahaffy et al., Biophys. J. 2004, 86, 1777-1793; Radmacher M. Measuring the elastic properties of living cells by the atomic force microscope. In: Jena B, Horber J K H, editors. atomic force microscopy in cell biology; 2002. p. 67-87; and Rotsch C et al., Biophys. J. 2000, 78, 520-535). In fact standard (sharp) AFM tips generate the largest local strains among all these methods. Dimitriadas et al (see, e.g. Dimitriadis et al., Biophys. J. 2002, 82, 2798-2810) have studied this issue and concluded that cell indentation studies with AFM should be conducted with blunted tips or micron-sized microspheres glued to the cantilever. Despite this issue, regular sharpened AFM tips have been widely and successfully used in mechanical studies of cell physiology. In the case of our study, we are interested in stimulating the core cytoskeleton of the cell, and this requires an indenter with micron-sized dimensions, and forces of 100 pN to 1 nN.

In this case, we are intentionally perturbing the cell mechanically in order to observe the response of the cell body in regions adjacent to the site of applied force. We are using two 5 micron diameter nickel microspheres, but the actual mode of perturbation is not critical nor is it the focus of our study. Rather it is the response of the cell following perturbation. Alternatively, we could have used an AFM probe, optical tweezers or a micropipette to stimulate the cell. Were it required, the nickel microsphere could be removed from the cell surface magnetically, after stimulation, thought we do not believe this is necessary.

Regarding the force levels applied here in comparison to other techniques: Optical tweezers typically operate in the 100 fN to 100 pN range. Magnetic bead-based tweezers operate in the pN to nN range. AFM typically operates in the 100 pN and larger force range. In our case, we are applying ~200 pN of force on a 5 micron diameter bead. At small indentations (~500 nm) this amounts to less than 1 pN applied for per square nanometer. For comparison, the typical force generated by a single molecular motor is in the range of several pN, while the contractile force generated through the cytoskeleton of a whole cell may range from nN to mN. Antibody-antigen binding forces are on the order of nN.

This subject is summarized in an excellent review article by K. Van Vliet, G. Bao and Suresh: "The biomechanics toolbox: experimental approaches for living cells and biomolecules," Acta Materialia 51 (2003) 5881-5905.

Example 3: Grin Spherical Mirror: A General Optical Probe Useful with Embodiments of the Invention A wide variety of micromirrors can be used with embodiments of the invention, including for example commercially available micron-sized elemental nickel microspheres and the like. In addition, one can use a gradient index (GRIN) retro reflector device with very wide viewing angle and high reflectivity. While not confined to uses with interferometry, these micromirror embodiments can make an ideal probe for very accurate interferometric measurements. In addition, while typically a micromirror, the GRIN mirror can be of any size, down to nanometers in diameter.

Such GRIN mirrors can be manufactured to have a variety of properties which allow them to be used in a variety of contexts. For example, these optical probes can be sensitive to magnetic, electric and gravitational fields. Such probes can be used for example: (1) to sense seismic waves or gravity waves; (2) as a metrology device for manufacturing and the like; (3) in combination with other apparatuses such as a microcantilever sensor; (4) as a component in optical communications devices; (4) as an optical switch; (5) to modify the force generated by optical tweezers; and (6) as an atomic force microscope-like probe.

Descriptions of a number of typical embodiments of this invention are provided below.
Background and Details
Nano Mirror.
Nano mirrors described herein can have a range of diameters and may be smaller than the spot size of the LED beam used for the readout (usually >5 microns). Typically they could be a micrometer or larger, although even smaller mirrors could be used. The nano mirror can be fabricated using a variety of techniques including Silicon or SiNx micromachining. Other methods include the deposition of gold or other metals through shadow masks combined with lift off techniques where the back of the substrate is dissolved away. In a batch process, millions of mirrors may be readily created on one substrate. Contact printing, dip pen lithography etc, all provide possible routes for mirror fabrication. The mirrors can be spherical, circular, square or may have a complex 3-dimensional form as determined by the experiment and manufacturing processes.

The mirrors themselves are readily functionalized using thiol- or silane-based chemistries. Such embodiments of the invention allow the mirrors to be able to be bio-functionalized so that, for example, they selectively attach themselves to a particular cell or cell type.

FIGS. 14A-14E provide schematics of illustrative processes useful to make micro/nano mirror embodiments of the invention.
Design.
Embodiments of these nano mirrors can have strong reflective properties from a wide range of angles to the incident beam. Both of these attributes can be crucial for a robust, easy to use measurement system. A large reflected signal enables a wide range of detector lens geometries to be used and greatly simplifies the procedures needed to control unwanted environmental backscatter. A wide viewing angle is critical because the nano mirror orientation, when bound to a cell membrane, cannot be controlled precisely. Such nano mirror embodiments can use a gradient index (GRIN) spherical lens design, with one hemisphere partially coated with gold to provide a reflective surface. This design is known as a Lunberg lens, and is used commonly for radar reflectors and antennas but not for a nano-scale optical reflectora.

Figure 15A:
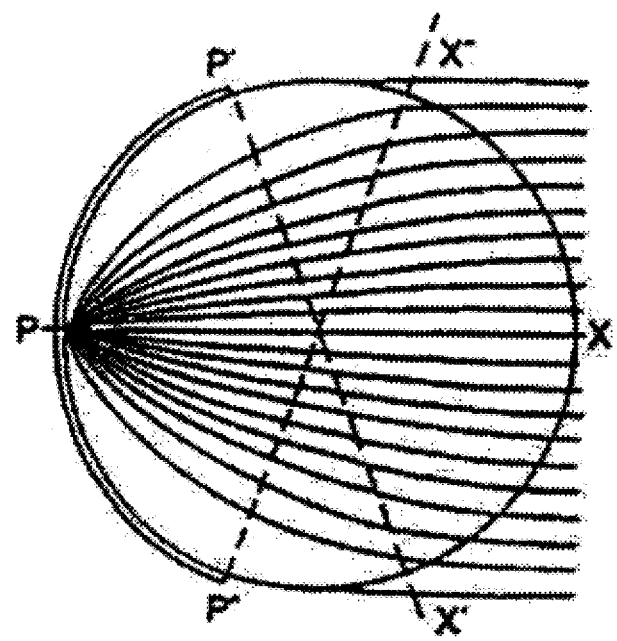
FIG. 15A shows a schematic of a Luneberg lens with a radially varying index of refraction (N), such that an entering signal will be refracted into a nearly elliptical path to a point on the opposite surface of the sphere.

A Luneberg lens is spherical, with a radially varying index of refraction (N), such that an entering signal will be refracted into a nearly elliptical path to a point on the opposite surface of the sphere (FIG. 15A). A reflective material located at the opposition point causes a return of the signal, again refracted elliptically through the sphere and out again in the direction it came. The radial index of refraction is given by the Equation below, where $N_{surface}$=that of the surrounding medium.

$$N(r)=[2-(r/r')^2]^{1/2}$$

A Luneberg lens performs much as a parabolic reflector, except that whereas a parabolic reflector is effective along its central axis (X), the Luneberg lens is an effective retro reflector over a wide range of entry angels (such as P'X' to P"X" in FIG. 15A).

The Luneberg lens reflector has close to a 55-degree viewing angle from center, compared to about ~5 degrees for a flat plate and ~25 degrees for corner reflectors. Its reflectivity approaches that of a flat surface, about three times more reflective than a square trihedral corner reflector and more than 200 times that of a metal sphere with the same radius. These properties assume that the reflector is above the Rayleigh wavelength limit. Using incident light of wavelength 450 nm, the lower limit for the mirror's diameter is approximately 900 nanometers. In this regime, the reflectivity increases as a function of $r^2$. For diameters smaller than about 200 nm, the reflectance drops rapidly, proportional to $r^6$. In typical embodiments of the invention, the spheres are in the range of 2-5 microns in diameter, similar to the size of marker beads used in other 'magnetic tweezer' cellular studies.

Figure 15B:
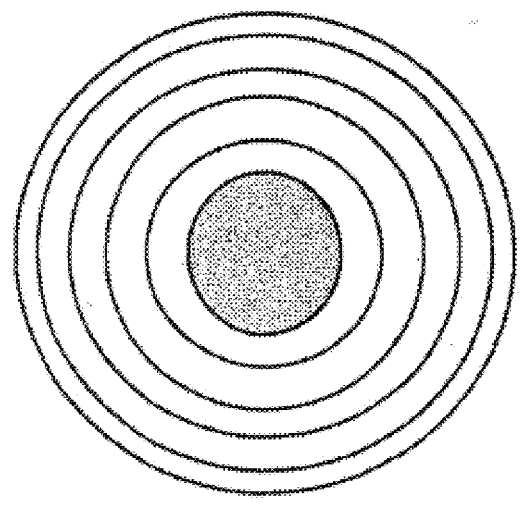
FIG. 15B shows a schematic of a 6-shell sphere, with refractive index decreasing with each layer from center, one which approximates the ideal Luneberg lens.

A 6-shell sphere, with refractive index decreasing with each layer from center, approximates the ideal Luneberg lens (see, e.g., FIG. 15B). Sanford and Sakurai calculated and subsequently demonstrated experimentally, that this design, when the diameter is roughly five wavelengths or larger, produces a close to ideal retro reflector when capped with a conducting layer (see, e.g. Sakurai, H., M. Ohki, et at. (2000) International Journal of Infrared and Millimeter Waves 21(70): 16341652). In fact, this multi-shell design is common in Luneberg lens reflectors used at microwave frequencies. Translating these parameters to optical frequencies (450 nm), a 2.5-micron diameter sphere, in water, produces the dimensions given Table 1 below.

TABLE 1

| Nano-structured Six-shell Luneberg lens | | | | | | |
|---|---|---|---|---|---|---|
| Lambda (nm) | | | | 450 | | |
| Diameter limit (nm) | | | | 2,580 | | |
| Particle Diameter (nm) | | | | 2,500 | | |
| Medium index of refraction | | | | 1.33 | | |
| Layer | 1 | 2 | 3 | 4 | 5 | 6 |
| Radius (nm) | 658 | 790 | 921 | 1,053 | 1,184 | 1,250 |
| Shell thickness (nm) | 658 | 133 | 131 | 131 | 131 | 66 |
| Index of refraction | 2.47 | 2.21 | 2.04 | 1.84 | 1.60 | 1.40 |

Layer-by-Layer Fabrication.

Embodiments of the invention can be made by a variety of processes known in the art, such as the layer-by-layer multishell nanoparticle methods used to fabricate Luneberg lens reflectors (see, e.g. Caruso, et al. (1998) Science 282 (5391): 1111-1114). Such layer-by-layer techniques typically involve the consecutive adsorption of material on a spherical core to produce a nano-structured particle. Such methods have been used with a wide variety of materials and combinations, including organic and inorganic polymers, semiconductors, metals, and biomolecules of different types. The techniques have progressed to such a degree that the thickness, composition and uniformity of each layer is highly controllable. Studies to date have largely focused on the use of multi-shell particles in optoelectronics and in drug delivery. Particles can be selected by simple filtering at each coating stage to assure uniformity.

In a typical nanomirror embodiment, each layer can be composed of a mixed polymer material with the desired index of refraction. The nano mirror will be working in a liquid (cell culture medium) with an index of refraction similar to water, which is 1.3333, making surface index matching a non-issue. Ideally, a center index should be 2.5. One option for obtaining this is to nucleate the sphere with a very small (o 50 nm), high index polysilicon particle, which at 450 nm has an index of refraction around five and an extinction coefficient close to zero. Fortunately, very high index polymers, with N up to about 2.2, are now available commercially (e.g. BREWER SCIENCE'S Specialty Materials Division). These transparent polymer-coating materials usually consist of multiple polymers species, with one component conjugated to a high refractive index metal oxide. The refractive index of the coating is then variable, depending on the ratio of the different components.

A next typical fabrication step is to vapor deposit reflective gold cap on the nanostructured polymer sphere. Artisans can assemble a monolayer of the spheres, using standard techniques, on silicon or some other surface. In this configuration, using latex micro beads, we have shown that the gold coating is confined to the hemisphere opposite the solid surface. If further control over the gold deposition is required, we can block the lower part of the sphere with a soluble, inert filler layer in the interstices between the spheres. In the final step, we will vapor deposit a layer of ferromagnetic material on top of the gold cap, followed by another thin layer of gold. The final gold layer will allow, via thiol linker chemistry, functionalization with fibronectin or some other cell adhesive substance.

A variety of methods and materials known in the art can be adapted to make and/or use embodiments of the invention, for example those disclosed in Abdelsalam, et al. (2004): Advanced Materials 16(1): 90-+; Alenohat et al. (2000): Biochem Biophys Res Commun 277(1): 93-9; Allersma et al. (1998): Biophysical Journal 74(2): 1074-1085; Bartlett, et al. (2004): Faraday Discussions 125: 11 7-1 32; Bausch et al. (2001): Biophys J 80(6): 2649-57; Caruso et al. (1998): Science 282(5391): 1111-1114; Caruso et al., (1999): Langmuir 15(23): 8276-8281; Caruso et al. (1999): Chemistry of Materials 11(11): 3394-3399; Caruso et al. (2001): Chemistry of Materials 13(2): 400-409; Coyle et al. (2003): Applied Physics Letters 83(4): 767-769; Gallet, F. (2004): Annales De Biologie Clinique 62(1): 85-86; Gittins et al., (2001): Journal of Physical Chemistry B 105(29): 6846-6852; Goldschmidt et al. (2001): Circ Res 88(7): 674-80; Guck et al. (2001): Biophys J 81(2): 767-84; Hannay et al., (1993): Journal of Modern Optics 40(8): 1437-1442; Hardaker et al., (1994): Journal of Electromagnetic Waves and Applications 8(3): 391-405; Kato et al. (2002): Macromolecules 35(26): 9780-9787; Koike et al. (1986): Applied Optics 25(19): 3356-3363; Liang et al. (2003): Chemistry of Materials 15(16): 3176-3183; Pommerenke et al. (1996): Eur J Cell Biol 70(2): 157-64; Schuetz et al., (2003): Advanced Functional Materials 13(12): 929-937; Seward et al., (1999): Optical Engineering 38(1): 164-169; and Wang et al. (2002): Nano Letters 2(8): 857-861, the contents of each of which is incorporated by reference.

Magnetically Driven Optical Bead Probe for In Situ Diagnosis of Cancer

Figure 16:
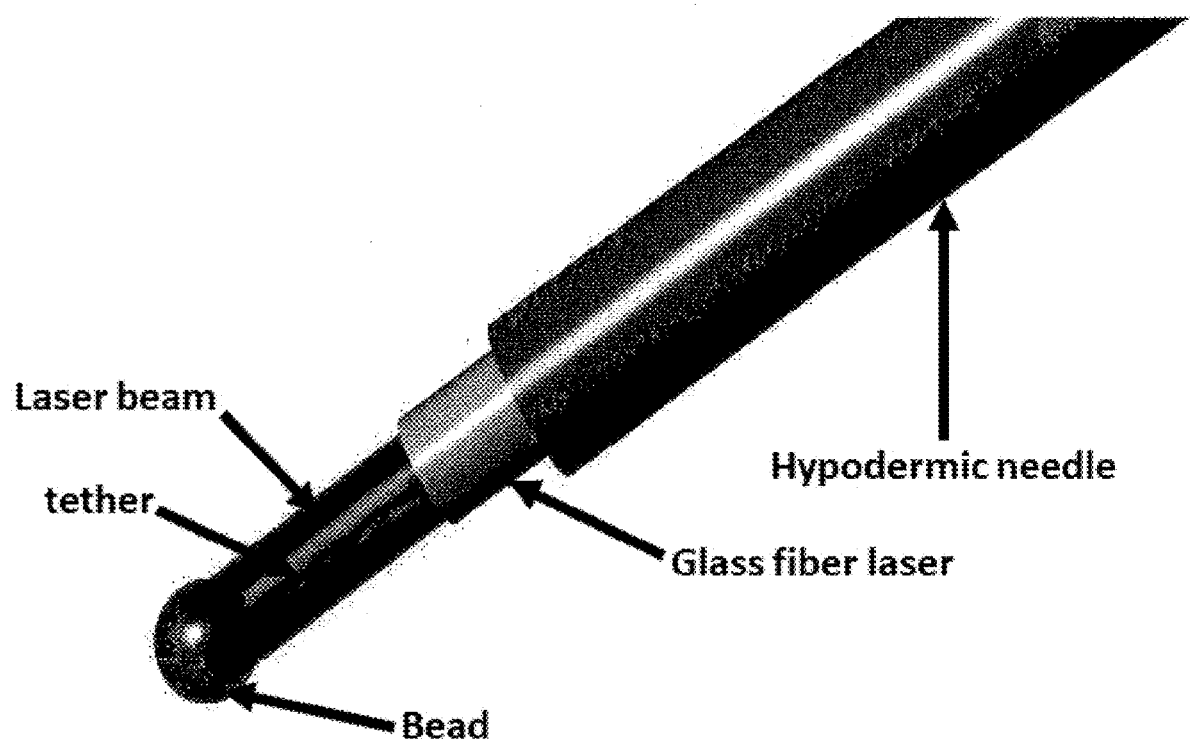
FIG. 16 shows one embodiment of a illustrative magnetically driven optical bead probe and elements typically associated with such probes.

One embodiment of the invention as shown in FIG. 16 combines the use of an external magnetic field to exert a force on a small optical bead with magnetic properties which uses specially graded index glass and a reflector to detect the mechanical response of the bead. This provides an in vivo measuring of the local mechanical properties and motility of cellular motion with a spatial resolution determined by the diameter of the bead. The bead can be tethered to a thin connecting wire which is flexible and connects to a rod on the end of a hypodermic needle. The magnetic drive and the needle assembly fit easily into even the smallest endoscope devices.

The rod connecting the optical sphere is fabricated from a single optical fiber which transmits and detects light in an interferometer mode of operation. In this embodiment of the invention, the local motion of the cell with respect to the fiber end is measured. Specifically, on the relative motion of the bead with the end of the fiber is detected which makes the device capable of removing background signals from organ motion possible. The length of the attachment cable between bead and fiber them determines also the spatial resolution of the device.

In the operational mode a surgeon or doctor probes local tissue with the needle directed by endoscope of other means such as ultrasound or X-ray imaging. The device constantly measures the local mechanical properties of the tissue. Cancerous cells are much softer and they are detected by the device using a computer technique programmed through neural learning a logarithms for different tissues (e.g. breast cancer etc.). Once the cancerous tissue is mapped and located, the position of the bead can be detected by having a fluorescent component of by external imaging methods or by position interpolation routines. This mapping can be combined by a variety of in vivo treatments which could involve removal of the probing sphere and fiber assembly and injection of chemotherapy agents or laser ablation for example.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

The invention claimed is:

1. A method for observing changes in mammalian cell mass in response to a change in environment using an interference microscope, the method comprising:
   (a) placing one or more mammalian cells in an observation chamber of the interference microscope, wherein the observation chamber is adapted to form an aqueous first environment and to contain said one or more mammalian cells and wherein reflecting microparticles are disposed on said one or more cells;
   (b) using phase shifting interferometry with said interference microscope to observe phase images of the mammalian cell in said first environment and determining the axial position of one or more of said reflective microparticles disposed on said one or more cells;
   (c) altering the first environment to form a second environment;
   (d) using phase shifting interferometry with said interference microscope to observe phase images of the mammalian cell in said second environment and determining the axial position of one or more of said reflective microparticles disposed on said one or more cells;
   (e) comparing the phase images observed in (b) with the phase images observed in (d); and
   (f) determining changes in the optical thickness of the cell from changes in the axial position of said one or more reflective microparticles and thereby determining the cell mass of the mammalian cell(s) resulting from said second environment.

2. The method of claim 1, wherein said altering the first environment to form a second environment comprises placing a biologically active agent in said second environment.

3. The method of claim 1, wherein the method is used to observe changes in optical thickness of the mammalian cell(s) in response to stimuli in a plurality of mammalian cells.

4. The method of claim 1, wherein the method is used to observe changes in optical thickness of the mammalian cell(s) at multiple time points.

5. The method of claim 1, wherein the microscope is a Michaelson interference microscope capable of observing interference fringes.

6. The method of claim 1, wherein the method is performed using a system comprising:
   (a) a detector operatively coupled to the microscope;
   (b) a sample assembly comprising the observation chamber;
   (c) a reference assembly comprising a reference chamber adapted to contain a fluid;
   (d) a memory storage element adapted to store one or more images of the cell(s; and
   (e) a processor element adapted to process one or more images of the cell(s).

7. The method of claim 6, wherein the microscope includes a reference assembly comprising:
   a first optical window;
   a first housing element adapted to hold the first optical window;
   a second optical window;
   a second housing element adapted to hold the second optical window; and
   a plurality of spacer elements disposable between the first optical window and the second optical window and adapted to separate the first and second optical windows to a defined distance.

8. The method of claim 7, wherein the method comprises determining changes in the optical thickness and thereby the cell mass of the mammalian cell(s) resulting from said second environment and storing this information in the memory storage element.

9. The method of claim 1, further comprising removing the cell(s) from the observation chamber and manipulating the cell(s) for further analysis.

* * * * *